United States Patent
Tan et al.

(10) Patent No.: US 9,580,736 B2
(45) Date of Patent: Feb. 28, 2017

(54) ANALYSIS OF NUCLEIC ACIDS ASSOCIATED WITH SINGLE CELLS USING NUCLEIC ACID BARCODES

(71) Applicant: Atreca, Inc., San Carlos, CA (US)

(72) Inventors: Yann Chong Tan, Palo Alto, CA (US); Gary Withey, San Francisco, CA (US)

(73) Assignee: Atreca, Inc., Redwood City, CA (US)

( * ) Notice: Subject to any disclaimer, the term of this patent is extended or adjusted under 35 U.S.C. 154(b) by 0 days.

(21) Appl. No.: 14/586,857

(22) Filed: Dec. 30, 2014

(65) Prior Publication Data
US 2015/0329891 A1    Nov. 19, 2015

Related U.S. Application Data

(60) Provisional application No. 61/922,012, filed on Dec. 30, 2013.

(51) Int. Cl.
| | |
|---|---|
| *C12P 19/34* | (2006.01) |
| *C12N 15/113* | (2010.01) |
| *C12Q 1/68* | (2006.01) |
| *B01L 3/00* | (2006.01) |

(52) U.S. Cl.
CPC .............. *C12P 19/34* (2013.01); *C12Q 1/6804* (2013.01); *C12Q 1/6806* (2013.01); *B01L 3/502784* (2013.01); *C12N 15/113* (2013.01)

(58) Field of Classification Search
None
See application file for complete search history.

(56) References Cited

U.S. PATENT DOCUMENTS

| | | | |
|---|---|---|---|
| 7,749,697 B2 | 7/2010 | Oleksiewicz et al. | |
| 2006/0193748 A1* | 8/2006 | Tai ........................ | G01N 30/34 422/70 |
| 2013/0225418 A1 | 8/2013 | Watson et al. | |

FOREIGN PATENT DOCUMENTS

| | | |
|---|---|---|
| EP | 2036989 A1 | 3/2009 |
| WO | 2012048341 A1 | 4/2012 |
| WO | 2012148497 A1 | 11/2012 |
| WO | 2013134261 A1 | 9/2013 |

OTHER PUBLICATIONS

PCT/US2014/072898, "International Search Report and Written Opinion", mailed Jun. 24, 2015, 19 pages.
PCT/US2014/072898, "Invitation to Pay Add'l Fees and Partial Search Report", mailed Mar. 27, 2015, 7 pages.

* cited by examiner

*Primary Examiner* — Jim Ketter
(74) *Attorney, Agent, or Firm* — Kilpatrick Townsend & Stockton LLP

(57) ABSTRACT

Provided herein are methods and compositions for analyzing nucleic acids associated with single cells using nucleic acid barcodes. According to some embodiments, a method for producing one or more polynucleotides of interest comprises: obtaining a plurality of RNAs associated with one or more samples, wherein the samples are obtained from one or more subjects, each RNA is associated with a single sample, and the RNAs associated with each sample are present in a separate reaction volume; adding an adapter molecule to the RNAs associated with each sample, wherein the adapter molecule is generated using an enzymatic reaction and comprises a universal priming sequence, a barcode sequence, and a binding site; and incorporating the barcode sequence into one or more polynucleotides associated with each sample, thereby producing the one or more polynucleotides of interest.

24 Claims, 25 Drawing Sheets

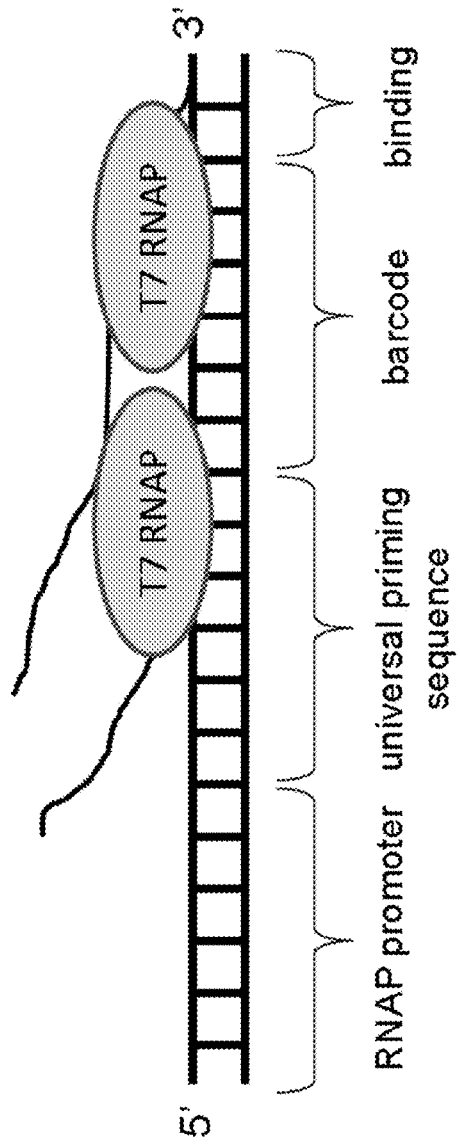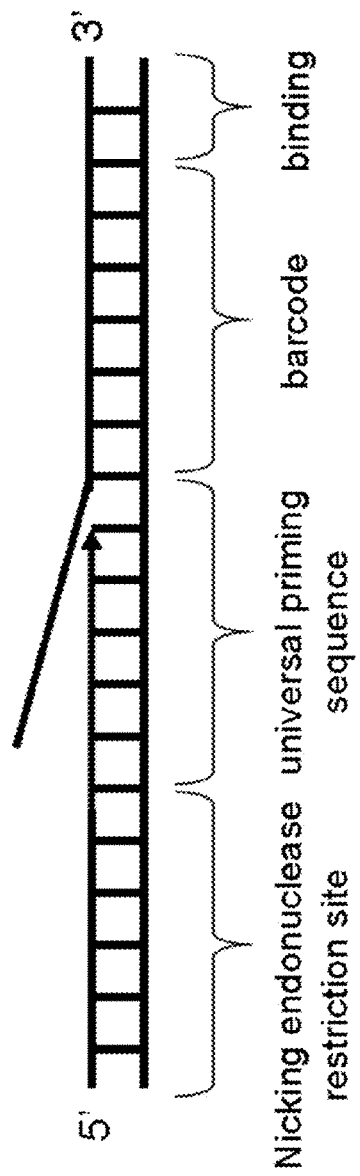
FIG. 2A
FIG. 2B

ANALYSIS OF NUCLEIC ACIDS ASSOCIATED WITH SINGLE CELLS USING NUCLEIC ACID BARCODES

CROSS-REFERENCES TO RELATED APPLICATIONS

This application claims the benefit of U.S. Provisional Application No. 61/922,012, entitled "Analysis of Nucleic Acids Associated with Single Cells using Nucleic Acid Barcodes" and filed Dec. 30, 2013, the entire contents of which are incorporated herein by reference for all purposes.

REFERENCE TO A "SEQUENCE LISTING," A TABLE, OR A COMPUTER PROGRAM LISTING APPENDIX SUBMITTED AS AN ASCII TEXT FILE

The Sequence Listing written in file 97519-920777.txt, created on Dec. 30, 2014, Ser. No. 18/227,200 bytes, machine format IBM-PC, MS-Windows operating system, is hereby incorporated by reference in its entirety for all purposes. Table 18. [barcode_part1] written in file Table 18. [barcode_part1].txt, 2,039,808 bytes; Table 18. [barcode_part2] written in file Table 18. [barcode_part2].txt, 90,112 bytes; Table 22. [i5 index primers] written in file Table 22. [i5 index primers].txt, 4,096 bytes; Table 32. [well-barcode] written in file Table 32. [well-barcode].txt, 4,096 bytes; Table 32. [plate-barcode] written in file Table 32. [plate-barcode].txt, 4,096 bytes, all created on Dec. 24, 2014, machine format IBM-PC, MS-Windows operating system, are hereby incorporated by reference in their entirety for all purposes.

BACKGROUND OF THE INVENTION

Variable genes such as immunoglobulin (Ig) and T cell receptor (TCR) genes are formed from rearrangement of V(D)J gene segments with P/N nucleotide additions between the junctions. A fully functional Ig or TCR protein is formed by association of two genes—heavy and light chain genes for Ig, alpha and beta genes for an αβTCR and gamma and delta genes for a γδTCR. This combinatorial approach results in an extremely large variety of different possible sequences.

This repertoire allows the immune system to be able to respond to novel immunological insults that have not yet been encountered by the organism. Immunoglobulin genes also undergo somatic hypermutation which further increases the repertoire size.

Correspondingly, any nucleic acid analysis of variable genes that allows for expression of the native Ig or TCR protein to investigate its functional properties requires not just sequencing individual B (for Ig genes) or T cells (for TCR genes), but also requires native pairing of the two genes that make up the protein. This can be done by single cell cloning and Sanger sequencing, but is slow and laborious (see, e.g., Wrammert et al., Nature, 2008, 453:667-671).

High-throughput methods have been developed for high-throughput sequencing of natively paired genes, and fall into two approaches. The first approach is to attach a unique nucleic acid barcode identifier to nucleic acids from a cell, and pairing is achieved via bioinformatically linking together genes if they share the same barcode and therefore originate from the same cell (PCT/US2012/000221). The second approach is to physically link nucleic acids from the two genes together (see, e.g., U.S. Pat. No. 7,749,697).

The first approach is superior as it allows pairing for multiple genes (such as B or T cell co-expressed genes that identify specific T cell or B cell subsets), while the second approach is limited to physically linking a few nucleic acids. To date, experimental data exists only for cases in which no more than two nucleic acids have been physically linked.

Associating nucleic acids unambiguously to a single cell (the first approach) rather than associating them with each other via linking (the second approach) has advantages. When nucleic acids are associated with each other, it can be difficult to distinguish PCR and sequencing errors from true biological variation. Assumptions have to be made about the accuracy of the sequencing platform and reads arbitrarily assigned to different sequences based on a percentage similarity cutoff, i.e. all reads with >95% similarity are assigned to a sequence and any differences between them are assumed to be due to sequencing errors. This is unable to distinguish between sequences that are very similar to one another (see Zhu et al., Frontiers in Microbiology, 2012, 3:315).

Furthermore, assumptions about how many cells share an identical sequence are made using the relative frequency of reads assigned to the sequence. This is an approximate measure and is affected by PCR amplification biases, as is well known in the field. Therefore, associating Ig or TCR nucleic acids with each other can only give an approximate, but not true representation of the repertoire sequenced (see Zhu et al., Frontiers in Microbiology, 2012, 3:315).

However, associating nucleic acids to single cells using nucleic acid barcodes allows for unambiguous differentiation between similar or even identical sequences from single B or T cells as each read can be assigned to a cell.

Furthermore, by building a consensus sequence with all reads associated with a cell, very accurate and almost completely error-free sequences can be obtained and an accurate representation of the repertoire sequenced can be obtained. This is also generalizable to analysis of all nucleic acids in a cell.

Still, technical difficulties in delivering unique barcodes to each single cell remain. The current best technology to attach nucleic acid barcodes to variable genes has unique barcodes in aqueous solution and each barcode exists in a separate storage container even before the reaction to attach barcodes to variable gene nucleic acids (PCT/US2012/000221), otherwise the nucleic acid barcodes will be mixed before use. This creates a logistical difficulty of barcoding many thousands of cells, due to the large number of containers required to contain the individual barcodes.

The requirement for a large number of storage containers also makes this approach incompatible with any sort of approach where a unique barcode cannot be individually pipetted into each individual reaction container (which will also contain a single cell). An example is nanoliter-sized reaction containers such as a nanowell approach, where it is impractical to pipette a unique barcode individually to each nanowell as there are thousands to hundreds of thousands of nanowells.

This is also infeasible in a nanodroplet approach, in which droplets are made using a water-in-oil emulsion, as hundreds of thousands of nanodroplets are generated with only a few aqueous streams (see for e.g., products by Dolomite Microfluidics or Raindance Technologies), and it is not possible to have unique barcodes in individual storage containers before delivering to the nanodroplet.

One method to deliver unique barcodes to individual reaction containers is by using limiting dilution to deposit a unique barcode into the majority of reaction containers. One may perform limiting dilution of barcodes attached to manipulable objects, such as beads, each of which has multiple copies of one particular barcode attached, or one may perform limiting dilution of barcodes in solution. Upon diluting such beads, multiple copies of one particular nucleic acid barcode are present in a reaction container, whereas upon diluting barcodes in solution, only a single copy of a particular nucleic acid barcode is present in a reaction container.

Moreover, addition of a nucleic acid barcode to the sample-derived nucleic acids of interest present in a reaction container will be more complete if the introduced barcode is amplified, to ensure that it is present in a sufficient quantity in the reaction chamber. For example, a typical mammalian cell contains roughly 400,000 copies of mRNA. To maximize the efficiency of the overall single-cell analysis, as many of these mRNA copies as possible should be barcoded. Therefore, at a minimum, roughly the same number of copies of a particular nucleic acid barcode as there are mRNA copies need to be present in the reaction container. Limiting dilution of barcodes in solution leads to just a single copy of a particular barcode in the reaction container, while dilution of small (e.g. 1-2 µm in diameter) beads bearing barcodes would be expected to provide maximally tens of thousands of copies. Thus, amplification of the barcode in either case is important to generate sufficient quantities of a particular nucleic acid barcode in a reaction container such that successful addition of the barcode to the greatest number of sample-derived nucleic acids occurs. However, beads are expected to provide significantly more starting material for and therefore significantly better barcode amplification. Also, a sufficiently large bead may contain hundreds of thousands of nucleic acid barcode molecules. In this case, cleavage of nucleic acid barcodes from the bead may be sufficient to generate sufficient quantities of a particular nucleic acid barcode in a reaction container.

Furthermore, if the nucleic acids are attached to a solid surface, they will not be as free to move about in comparison to nucleic acids in solution. Solid phase kinetics are much slower than aqueous phase kinetics for nucleic acid complementary base pairing, and may result in much less efficient addition of barcodes to nucleic acids of interest. Preferably, nucleic acid barcodes should exist in the aqueous phase before participating in the barcoding reaction.

This current invention improves upon a previous invention (PCT/US2012/000221) to attach unique barcodes to each sample, where each sample is usually a single cell, but is generalizable to any type of sample. The current invention enables delivery of unique barcodes to any type of reaction container, and is also suitable for nanoliter-sized reaction containers and does not require keeping unique nucleic acid barcodes in separate storage containers. It is amendable to but does not require manually pipetting a unique barcode into each reaction container. It delivers one or more copies of a unique barcode or unique barcode set into each reaction container and the barcode is attached to nucleic acids of interest in a reaction that occurs in the aqueous phase with rapid aqueous phase kinetics. As the reaction attaches barcodes to all nucleic acids of interest in a cell, i.e. all reverse transcribed RNA in a cell, the current invention enables single cell transcriptomics analysis, and is not limited to associating immunoglobulin variable genes to specific samples. Furthermore, the amplification reaction can occur at a sufficiently low temperature that it is compatible with mesophilic enzymes (that are otherwise inactivated at high temperatures) to add barcodes to nucleic acids of interest.

SUMMARY OF THE INVENTION

Disclosed herein are methods and compositions for analyzing nucleic acids associated with single cells using nucleic acid barcodes. One method disclosed herein for producing one or more polynucleotides of interest comprises obtaining a plurality of nucleic acids associated with one or more samples, wherein the samples are obtained from one or more subjects, and the nucleic acids associated with a sample are present in a separate reaction volume. The nucleic acids can be RNA or DNA molecules (for example, cDNA molecules). In some embodiments, an adapter molecule is added to the nucleic acids associated with the sample. In some embodiments, the adapter molecule is generated using an enzymatic reaction and comprises a universal priming sequence, a barcode sequence, and a binding site. In some embodiments, the barcode sequence is incorporated into one or more polynucleotides associated with the sample, thereby producing the one or more polynucleotides of interest. In some embodiments, the method comprises adding an adapter molecule to the nucleic acids associated with the sample, wherein the adapter molecule is generated using an enzymatic reaction and comprises a universal priming sequence, a barcode sequence, and a binding site; and incorporating the barcode sequence into one or more polynucleotides associated with the sample, thereby producing the one or more polynucleotides of interest.

Disclosed herein is a method for producing one or more polynucleotides of interest. The method comprises obtaining a plurality of RNAs associated with one or more samples, wherein the samples are obtained from one or more subjects, and the RNAs associated with the sample are present in a separate reaction volume; adding an adapter molecule to the RNAs associated with the sample, wherein the adapter molecule is generated using an enzymatic reaction and comprises a universal priming sequence, a barcode sequence, and a binding site; and incorporating the barcode sequence into one or more polynucleotides associated with the sample, thereby producing the one or more polynucleotides of interest. In some embodiments, each RNA, or at least one of the plurality of RNAs, is associated with a single sample from the one or more samples. Some embodiments of the method further comprise generating the adapter molecule using the enzymatic reaction.

In some embodiments, the adapter molecule is generated by contacting a template molecule with one or more enzymes. In some embodiments, the template molecule is a DNA molecule comprising an RNA polymerase (RNAP) promoter, and the one or more enzymes include an RNA polymerase. The RNAP promoter can be selected from the group consisting of T7, T3, and SP6. In some embodiments, the template molecule is a DNA molecule comprising a nicking endonuclease restriction site, and the one or more enzymes include a nicking endonuclease and a strand-displacing DNA polymerase. The nicking endonuclease restriction site can be selected from the group consisting of Nt.BbvCI, Nt.BspQI, Nt.BsmAI, Nt.BstNBI, Nt.AlwI, and Nt.BsmAI. The strand-displacing DNA polymerase can be selected from the group consisting of Klenow exo-, Bst Large Fragment and engineered variants of Bst Large Fragment. The DNA molecule can be a double-stranded molecule or a single-stranded molecule that is useful as a template for generating a double-stranded molecule.

In some embodiments, the template molecule is bound to a solid support, the solid support is contacted with an aqueous solution, and the adapter molecule is released into the aqueous solution as it is generated. In some embodiments, adding the adapter molecule to the RNAs associated with one sample comprises combining the aqueous solution with the reaction volume in which the RNAs are present. In some embodiments, the aqueous solution is present in the same reaction volume as the RNAs associated with one sample. In some embodiments, the template molecule comprises an endonuclease restriction site, the one or more enzymes comprise a restriction endonuclease, and the adapter molecule comprises a portion of the template molecule, said portion being generated and released into the aqueous solution upon contacting the template molecule with the restriction endonuclease. In some embodiments, the solid support is a bead or a surface (e.g., the surface of a microtitre well or tube).

In some embodiments of the method, the adapter molecule is free in solution prior to adding the adapter molecule to the RNAs associated with one sample. In some embodiments, the adapter molecule is generated in a compartment, and adding the adapter molecule to the RNAs associated with one sample comprises combining the compartment with the reaction volume in which the RNAs are present. In some embodiments, the adapter molecule is generated in the reaction volume in which the RNAs to which the adapter molecule is added are present. In some embodiments, the adapter molecule is not generated in the reaction volume in which the RNAs to which the adapter molecule is added are present. In some embodiments, the enzymatic reaction is an isothermal reaction. In some embodiments, the adapter molecule further comprises a unique molecular identifier (UMI) sequence. In some embodiments, the adapter molecule is an RNA molecule. The adapter molecule can be generated using RNAP.

In some embodiments of the method, the adapter molecule is a DNA molecule. The adapter molecule can be generated using DNAP.

In some embodiments, producing the one or more polynucleotides of interest comprises reverse-transcribing the RNAs associated with the sample, thereby synthesizing a plurality of first-strand cDNAs, at least some of the RNAs associated with the sample comprise a sequence region complementary to the binding site of the adapter molecule, and the adapter molecule is used as a primer for reverse transcription, such that the barcode sequence is incorporated into first-strand cDNAs associated with the sample. In these embodiments, the binding site can comprise a poly-T tract or a random tract. The binding site can occur at the 3' end of the adapter molecule. The adapter molecule can be generated in a compartment, and reverse-transcribing the RNAs associated with the sample can occur upon combining the compartment with the reaction volume in which the RNAs are present. Reverse-transcribing the RNAs associated with the sample can occur in the same reaction volume where the adapter molecule added to the RNAs is generated.

Some embodiments of the method further comprise reverse-transcribing the RNAs associated with the sample to obtain a plurality of cDNAs, wherein reverse-transcribing an RNA comprises synthesizing a first strand of cDNA using a reverse transcriptase and a first-strand primer. In these embodiments, the reverse transcriptase can be MMLV H-reverse transcriptase. The adapter molecule can be generated in a compartment, and adding the adapter molecule to the RNAs associated with one sample can comprise combining the compartment with the reaction volume in which the RNAs are present. First stands of cDNA can be synthesized prior to or subsequent to combining the compartment with the reaction volume.

In some embodiments, reverse-transcribing the RNAs associated with the sample occurs in the same reaction volume where the adapter molecule added to the RNAs is generated. In these embodiments, a buffer in the reaction volume can comprise at least one of Tris, potassium ions, chloride ions, sulphate ions, ammonium ions, acetic acid ions, or magnesium ions at a pH range from pH 8.0 to pH 8.8.

In some embodiments, the reverse transcriptase has template switching activity, at least some first strands of cDNA associated with the sample comprise a 3' overhang, the binding site of the adapter molecule comprises a 3' portion complementary to the 3' overhang, and the adapter molecule serves as a template for the reverse transcriptase, such that the barcode sequence is incorporated into first strands of cDNAs associated with the sample. In these embodiments, the 3' overhang can comprises one or more C nucleotides and the 3' portion of the binding site can comprise one or more G nucleotides. The first-strand primer can comprise a poly-T tract or a random sequence.

In some embodiments, producing polynucleotides of interest comprises amplifying the first strands of cDNA for each sample using a first (e.g., forward) primer and a second (e.g., reverse) primer, the second primer having the same sequence as at least a portion of the first-strand primer, wherein the first primer or the second primer is the adapter molecule. In these embodiments, the first primer or the second primer can be the adapter molecule. The first-strand primer can comprise a poly-T tract or a random sequence.

In some embodiments of the method, each sample comprises a cell. The cell can be a blood cell, an immune cell, a tissue cell, or a tumor cell. In some embodiments, the cell is a B cell or T cell. The B cell can be a plasmablast, a memory B cell, or a plasma cell. In some embodiments, the RNAs associated with each sample comprise mRNAs, for example at least 1, 3, 10, 30, 100, 300, 1,000, 3,000, 10,000, 30,000, 100,000, 300,000, or 1,000,000 mRNAs. In some embodiments, the RNAs associated with each sample comprise the transcriptome of a cell or the total RNA of a cell. In some embodiments, at least 10, 30, 100, 300, 1,000, 3,000, 10,000, 30,000, 100,000, 300,000, or 1,000,000 polynucleotides of interest are produced per sample. In some embodiments, the one or more samples comprise at least 10, 30, 100, 300, 1,000, 3,000, 10,000, 30,000, 100,000, 300, 000, or 1,000,000 cells. In some embodiments, the one or more samples are obtained from the same subject. Some embodiments further comprise contacting the samples with a lysis buffer.

Some embodiments further comprise contacting the samples with a nucleic acid marker, thereby allowing the nucleic acid marker to bind to a subset of the samples; and washing the samples, thereby removing the nucleic acid marker from samples to which the nucleic acid marker does not bind, wherein, for samples within the subset, the adapter molecule added to the RNAs associated with the sample is also added to the nucleic acid marker, and one or more polynucleotides of interest are produced using the labeled nucleic acid marker. In these embodiments, the nucleic acid marker can comprise a nucleic acid coupled to a molecular label. The molecular label can be an antibody, antigen, or protein. The molecular label can have affinity for one or more cell surface moieties. In some embodiments, the nucleic acid is an RNA. In some embodiments, the nucleic acid is a DNA and can comprise an RNAP promoter. In some embodiments, the sample is contacted with a first nucleic acid marker and a second nucleic acid marker, wherein the first nucleic acid marker comprises a first nucleic acid coupled to a first molecular label, and the second nucleic acid marker comprises a second nucleic acid coupled to a second molecular label. The first nucleic acid and second nucleic acid can comprise different sequence regions. In some embodiments, the first and second molecular labels are different (e.g., two different antibodies to different cell surface antigens). Thus, the method allows multiplex labeling of samples, such as single cells, with nucleic acid markers comprising adapter molecules, and producing one or more polynucleotides of interest that are associated with the sample.

In some embodiments of the method the one or more samples are obtained from the same subject. In some embodiments, the one or more samples are obtained from at least 3, 10, 30, or 100 different subjects.

Also disclosed herein are barcode adapter constructs. Some such barcode adapter constructs comprise an RNAP promoter, a universal priming sequence, a barcode sequence, and a binding site. The RNAP promoter can be selected from the group consisting of T7, T3, and SP6. Other barcode adapter constructs comprise a nicking endonuclease restriction site, a universal priming sequence, a barcode sequence, and a binding site. The nicking endonuclease restriction site can be selected from the group consisting of Nt.BbvCI, Nt.BspQI, Nt.BsmAI, Nt.BstNBI, Nt.AlwI, and Nt.BsmAI.

Further disclosed herein is a solid support comprising a barcode adapter construct as described above. In some embodiments, the barcode adapter construct is bound to the solid support via a covalent bond. In some embodiments, multiple copies of the barcode adapter construct are bound to the solid support. For example, at least 10, 30, 100, 300, 1,000, 3,000, 10,000, 30,000, 100,000, 300,000, or 1,000, 000 copies of the barcode adapter construct can be bound to the solid support. In some embodiments, each copy of the barcode adapter construct comprises the same barcode sequence. An adapter template library comprising a plurality of solid supports coupled to multiple copies of the adapter construct is also disclosed herein. In some embodiments, the plurality of solid supports comprises at least 10, 30, 100, 300, 1,000, 3,000, 10,000, 30,000, 100,000, 300,000, or 1,000,000 solid supports. In some embodiments, at least two of the solid supports comprise adapter constructs with different barcode sequences or UMI sequences. In some embodiments, every solid support of the plurality of solid supports comprises an adapter construct with a different barcode sequence or a different UMI sequence.

Also disclosed herein is a nucleic acid marker comprising a nucleic acid coupled to a molecular label. In some embodiments, the molecular label is an antibody, antigen, or protein. In some embodiments, the molecular label has an affinity for one or more cell surface moieties. In some embodiments, the nucleic acid is an RNA. In some embodiments, the nucleic acid is a DNA. The DNA can comprise an RNAP promoter sequence. In some embodiments, a plurality of nucleic acid markers are described, where at least one of the plurality comprises a first molecular label (i.e., a first antibody) and at least one of the plurality comprises a second molecular label (i.e., a second antibody). In some embodiments, the first and second molecular labels are different, thus providing compositions useful for multiplex labeling of different cell surface moieties (e.g., different cell surface antigens) with nucleic acid markers described herein.

Further disclosed herein are kits comprising adapter constructs described herein. The kit can comprise a plurality of solid supports coupled to adapter constructs described herein. In some embodiments, the kit comprises an adapter template library comprising a plurality of adapter constructs. In some embodiments, the kit comprises an adapter template library comprising a plurality of adapter constructs coupled to a plurality of solid supports. The kit can further comprise enzymes for generating an adapter molecule described herein from the adapter construct by an enzymatic reaction. In some embodiments, the kit comprises a cell suspension buffer described herein.

Further disclosed herein is a cell suspension buffer comprising an osmoprotectant. In some embodiments, the osmoprotectant is a betaine or a close structural analog thereof. For example, the osmoprotectant can be a glycine betaine. In some embodiments, the osmoprotectant is a sugar or polyol. For example, the osmoprotectant can be trehalose. In some embodiments, the osmoprotectant is an amino acid. For example, the osmoprotectant can be proline. In some embodiments of the cell suspension buffer, the osmolarity of the buffer is about 250-350 mOsm/L. In some embodiments, the osmoprotectant contributes up to 10%, 20%, 30%, 40%, 50%, 60%, 70%, 80%, 90%, or 100% of the osmolarity of the buffer. In some embodiments, the buffer comprises about 230-330 mM betaine and about 10 mM NaCl.

Also disclosed herein is a method of attaching a polynucleotide to a solid support, wherein the polynucleotide contains a barcode sequence. The method comprises the steps of: a) generating a hydrophilic compartment of an inverse emulsion, the hydrophilic compartment containing: a solid support, a barcode oligonucleotide comprising a barcode sequence, and an oligonucleotide bound to a surface of the solid support via a capture moiety, wherein the bound oligonucleotide comprises a 3' sequence complementary to a 3' sequence of the barcode oligonucleotide; and b) performing a polymerase extension reaction to incorporate the barcode sequence into the bound oligonucleotide on the solid support. In some embodiments, the barcode oligonucleotide further comprises a 5' sequence identical or complementary to a PCR reverse primer sequence. These embodiments can further comprise performing a PCR reaction using a fluorophore-labeled reverse primer. In some embodiments, the solid support is a bead. In some embodiments, the capture moiety is streptavidin. In some embodiments, the capture moiety comprises a carboxyl group, epoxy group, or hydroxyl group. In some embodiments, the capture moiety comprises gold to capture thiolyated oligonucleotides.

In some embodiments, the barcode oligonucleotide further comprises a universal priming sequence and a binding site. The barcode oligonucleotide can further comprise an RNAP promoter selected from the group consisting of T7, T3, and SP6. Alternatively or in addition, the barcode oligonucleotide can further comprise a nicking endonuclease restriction site selected from the group consisting of Nt.BbvCI, Nt.BspQI, Nt.BsmAI, Nt.BstNBI, Nt.AlwI, and Nt.BsmAI. The binding site can be one or more G nucleotides.

Another method of attaching a polynucleotide to a solid support, wherein the polynucleotide contains a barcode sequence, is also disclosed. The method comprises the steps of: a) providing: a solid support, a first barcode oligonucleotide comprising a W sequence, and an oligonucleotide bound to a surface of the solid support via a capture moiety, wherein the bound oligonucleotide comprises (i) an S1x sequence and (ii) a sequence complementary to a 3' sequence of the first barcode oligonucleotide; b) performing a polymerase extension reaction or a ligation reaction to incorporate the W sequence into the bound oligonucleotide; c) providing a second barcode oligonucleotide comprising an (i) S2y sequence and (ii) a 3' sequence complementary to the 3' end of the bound oligonucleotide resulting from step b); and d) performing a polymerase extension reaction or ligation reaction to incorporate the S2y sequence into the bound oligonucleotide, thereby attaching a polynucleotide to the solid support, wherein the polynucleotide contains a barcode sequence, and the barcode sequence comprises the S1x, W, and S2y sequences.

In some embodiments of this method, the solid support is a bead. In some embodiments, the capture moiety is streptavidin. In some embodiments, the capture moiety comprises a carboxyl group, epoxy group, or hydroxyl group. In some embodiments, the capture moiety comprises gold to capture thiolyated oligonucleotides. In some embodiments, a chosen barcode oligonucleotide, the chosen barcode oligonucleotide being either the first barcode oligonucleotide or the second barcode oligonucleotide, further comprises a universal priming sequence and a binding site. The chosen barcode oligonucleotide can further comprise an RNAP promoter selected from the group consisting of T7, T3, and SP6. Alternatively or in addition, the chosen barcode oligonucleotide can further comprise a nicking endonuclease restriction site selected from the group consisting of Nt.BbvCI, Nt.BspQI, Nt.BsmAI, Nt.BstNBI, Nt.AlwI, and Nt.BsmAI. The binding site can be one or more G nucleotides.

Further disclosed herein is a solid support prepared by any embodiment of the foregoing methods, wherein the solid support is attached to a polynucleotide and the polynucleotide contains a barcode sequence. Also disclosed is a barcode library comprising a plurality of these solid supports.

In addition, a microfluidic droplet device is disclosed herein for encapsulating cells, barcode adapter templates, and reagents for producing polynucleotides of interest. The device comprises (a) three independently controlled pressure sources, (b) three microfluidic pathways, (c) three flow sensors, (d) two sample loops, (e) a microfluidic droplet chip, and (f) a sample collection container, wherein: each pressure source is coupled to and drives fluid through one of the microfluidic pathways, one of the flow sensors is disposed along each microfluidic pathway downstream of the respective pressure source, a first microfluidic pathway passes through a first sample loop, a second microfluidic pathway passes through a second sample loop, the first and second sample loops being in contact with a thermal cooling unit, the first and second microfluidic pathways merge at a first junction to form a combined pathway, the combined pathway and third microfluidic pathway merge at a second junction to form a sample pathway, the second junction occurring within the microfluidic droplet chip and downstream of the first junction, and the sample pathway passes into the sample collection container downstream of the second junction, such that (a)-(f) are fluidly connected.

In some embodiments of the device, each pressure source comprises a pressure pump. In some embodiments, each pressure source comprises a syringe pump. In some embodiments, the first sample loop is configured to meter the flow of an aqueous solution toward the microfluidic droplet chip, wherein the aqueous solution comprises cells and barcode adapter templates. In some embodiments, the second sample loop is configured to meter the flow of a reaction mixture toward the microfluidic droplet chip, wherein the reaction mixture comprises reagents for cell lysis and reagents for producing polynucleotides of interest. In some embodiments, the third microfluidic pathway is configured to deliver an oil/surfactant mix to the microfluidic droplet chip. In some embodiments, the thermal cooling unit comprises a Peltier device. In some embodiments, the thermal cooling unit comprises an ice bin. In some embodiments, the first junction occurs within the droplet chip. In some embodiments, the third microfluidic pathway is split into two subpathways upstream of the microfluidic droplet chip, the two subpathways merge with the combined pathway at the second junction, and the second junction has flow-focusing geometry. In some embodiments, the second junction has a t-junction geometry. In some embodiments, the first microfluidic pathway is configured to accommodate cells, and the second microfluidic pathway is configured to accommodate barcode adapter templates bound to solid supports.

Disclosed herein is a method for producing one or more polynucleotides of interest, comprising obtaining a cDNA library comprising a plurality of cDNAs associated with one or more samples obtained from one or more subjects, wherein each cDNA is associated with a single sample in the one or more samples, and wherein the cDNAs associated with each sample are present in a separate container or compartment. In some embodiments, an adapter molecule is added to the cDNAs associated with each sample to produce the one or more polynucleotides of interest. In some embodiments, the adapter molecule is generated from an adapter construct comprising a universal priming sequence, a barcode, and a cDNA binding site.

In some aspects, the adapter molecules are generated using an isothermal reaction. In some aspects, the adapter construct further comprises an RNA polymerase (RNAP) promoter. In some aspects, the RNAP promoter is selected from the group consisting of T7, T3, and SP6. In some aspects, the adapter construct further comprises a nicking endonuclease restriction site. In some aspects, the nicking endonuclease restriction site is selected from the group consisting of Nt.BbvCI, Nt.BspQI, Nt.BsmAI, Nt.BstNBI, Nt.AlwI, and Nt.BsmAI. In some aspects, the adapter is an RNA adapter generated by RNAP. In some aspects, the adapter is a DNA adapter generated by a nicking endonuclease and strand displacing DNA polymerase. In some aspects, the strand displacing DNA polymerase is selected from the group consisting of Klenow exo- and Bst Large Fragment and its engineered variants, such as Bst 2.0.

In some aspects, the method further comprises allowing the 3' end of the adapter molecule to attach to the 3' end of each cDNA in the library to produce the one or more polynucleotides of interest.

In some aspects, the adapter is added by annealing the adapter to the '3 tail of a cDNA generated during a reverse transcription reaction. In some aspects, each cDNA comprises at least one C nucleotide, wherein C is located at the 3' end of each cDNA, wherein the adapter region comprises at least one G nucleotide, wherein G is located at the 3' end of the adapter region, and wherein the adapter region is attached to each cDNA via binding between the G and C. In some aspects, the adapter molecule is single-stranded, and further comprising incorporating the complementary of the adapter molecule into each cDNA by allowing an enzyme to make the adapter molecule double-stranded. In some aspects, the complementary of the adapter molecule is incorporated into each cDNA to produce the polynucleotide of interest by an MMLV H-reverse transcriptase.

In some aspects, each sample comprises a cell. In some aspects, the cell is a blood cell, an immune cell, a tissue cell, or a tumor cell. In some embodiments, the cell is a B cell or a T cell. In some aspects, the B cell is a plasmablast, memory B cell, or a plasma cell.

Also disclosed herein is a method of attaching a barcode to a solid support comprising the steps of: a) generating a hydrophilic compartment of an inverse emulsion, the hydrophilic compartment comprising: a solid support contained therein, wherein the solid support comprises an oligonucleotide bound to the surface via a capture moiety, wherein the oligonucleotide comprises a 3' sequence complementary to a 3' sequence on a barcode oligonucleotide; a barcode oligonucleotide comprising a 3' sequence complementary to the 3' end of the bound oligonucleotide, and a barcode sequence; and b) performing a polymerase extension reaction to add the sequence of the barcode to the bound oligonucleotide on the solid support.

In some aspects, the barcode oligonucleotide further comprises a 5' sequence identical or complementary to a reverse PCR primer. In some aspects, the method further comprises performing a PCR reaction using a fluorophore-labeled reverse primer.

In some aspects, the solid support is a bead or a surface. In some aspects, the capture moiety is streptavidin. In some aspects, the barcode oligonucleotide further comprises a RNA polymerase (RNAP) promoter and/or an endonuclease restriction site, a universal priming sequence, a cDNA binding site. In some aspects, the RNAP promoter selected from the group consisting of T7, T3, and SP6. In some aspects, the nicking endonuclease restriction site is selected from the group consisting of Nt.BbvCI, Nt.BspQI, Nt.BsmAI, Nt.BstNBI, Nt.AlwI, and Nt.BsmAI. In some aspects, the cDNA binding site is one or more G nucleotides.

Also disclosed herein is a method of attaching a barcode to a solid support comprising the steps of a) providing a solid support, with an oligonucleotide bound to the solid support via a capture moiety, wherein the oligonucleotide comprises an $S1_x$ sequence, and a sequence complementary to a 3' sequence on a first barcode oligonucleotide; a first barcode oligonucleotide comprising a 3' sequence complementary to a sequence of the bound oligonucleotide, and a W sequence; and b) performing a polymerase extension reaction or ligation reaction to add the W sequence to the $S1_x$ sequence of the bound oligonucleotide on the solid support; c) providing a second barcode oligonucleotide with a $S2_y$ sequence comprising a 3' sequence complementary to the 3' end of the oligonucleotide extended in step b); d) performing a polymerase extension reaction or ligation reaction to add the $S2_y$ sequence to the $S1_x$ and W sequences of the bound oligonucleotide on the solid support, where the barcode sequence comprises the $S1_x$, W, and $S2_y$ sequences.

In some aspects, the solid support is a bead. In some aspects, the capture moiety is streptavidin. In some aspects, the first or second barcode oligonucleotide further comprises a RNA polymerase (RNAP) promoter and/or a nicking endonuclease restriction site, a universal priming sequence, a cDNA binding site. In some aspects, the RNAP promoter selected from the group consisting of T7, T3, and SP6. In some aspects, the endonuclease restriction site is selected from the group consisting of Nt.BbvCI, Nt.BspQI, Nt.BsmAI, Nt.BstNBI, Nt.AlwI, and Nt.BsmAI. In some aspects, the cDNA binding site is one or more G nucleotides.

Also disclosed herein is a solid support with an attached barcode generated by any of the methods disclosed above. Also disclosed herein is a beaded barcode library comprising a plurality of such solid supports with attached barcodes.

Also disclosed herein is a barcode adapter construct comprising a universal priming sequence, a barcode, and a cDNA binding site. In some aspects, the construct further comprises an RNAP promoter. In some aspects, the RNAP promoter is selected from the group consisting of T7, T3, and SP6. In some aspects, the construct further comprises a nicking endonuclease restriction site. In some aspects, the nicking endonuclease restriction site is selected from the group consisting of Nt.BbvCI, Nt.BspQI, Nt.BsmAI, Nt.BstNBI, Nt.AlwI, and Nt.BsmAI.

Also disclosed herein is a barcode adapter template bead comprising a solid support and a barcode adapter molecule bound to the solid support via a capture moiety, wherein the barcode adapter molecule comprises a barcode sequence and a cDNA binding site. In some aspects, the cDNA binding site comprises one or more G nucleotides. In some aspects, the barcode sequence comprises a sequence $S1_x$-W-$S2_y$. Also disclosed herein is a beaded barcode library comprising a plurality of the barcode adapter template beads as disclosed above.

Also disclosed herein is a polynucleotide library comprising a plurality of barcode adapter template beads comprising a solid support and a barcode adapter molecule bound to the solid support via a capture moiety, wherein the barcode adapter molecule comprises a barcode sequence and a cDNA binding site, wherein a cDNA region is coupled to the 3' end of the adapter.

In some aspects, the cDNA binding site comprises one or more G nucleotides. In some aspects, the barcode sequence comprises a sequence $S1_x$-W-$S2_y$.

In some aspects, the cDNA is derived from a B cell. In some aspects, the B cell is a plasmablast, memory B cell, or a plasma cell. In some aspects, the cDNA is a B-cell derived variable immunoglobulin region.

Also disclosed herein is a microfluidic droplet device as shown in FIGS. 17-19.

BRIEF DESCRIPTION OF THE DRAWINGS

These and other features, aspects, and advantages will become better understood with regard to the following description, and accompanying drawings, where:

FIGS. 2A and 2B show methods of amplifying or generating an adapter molecule according to some embodiments of the invention. In FIG. 2A, RNA barcode adapters are synthesized in a linear amplification reaction by an RNAP, such as T7, which binds to a promoter sequence on a DNA template and synthesizes single-stranded barcode adapter RNA. In FIG. 2B, a nicking endonuclease such as Nt.BbvCI (NEB) is used to introduce a nick on the sense strand of a DNA template. DNA barcode adapters are then synthesized in an amplification reaction by a strand-displacing enzyme, such as Klenow exo-, which extends the nick and displaces the single-stranded barcode adapter.

The barcode adapter base-pairs with the tailed dCs (bottom) and the reverse transcriptase continues transcription using the barcode adapter as a template, incorporating the barcode sequence into the $1^{st}$ strand cDNA. All mRNAs in the reaction are therefore barcoded.

Figure 3:
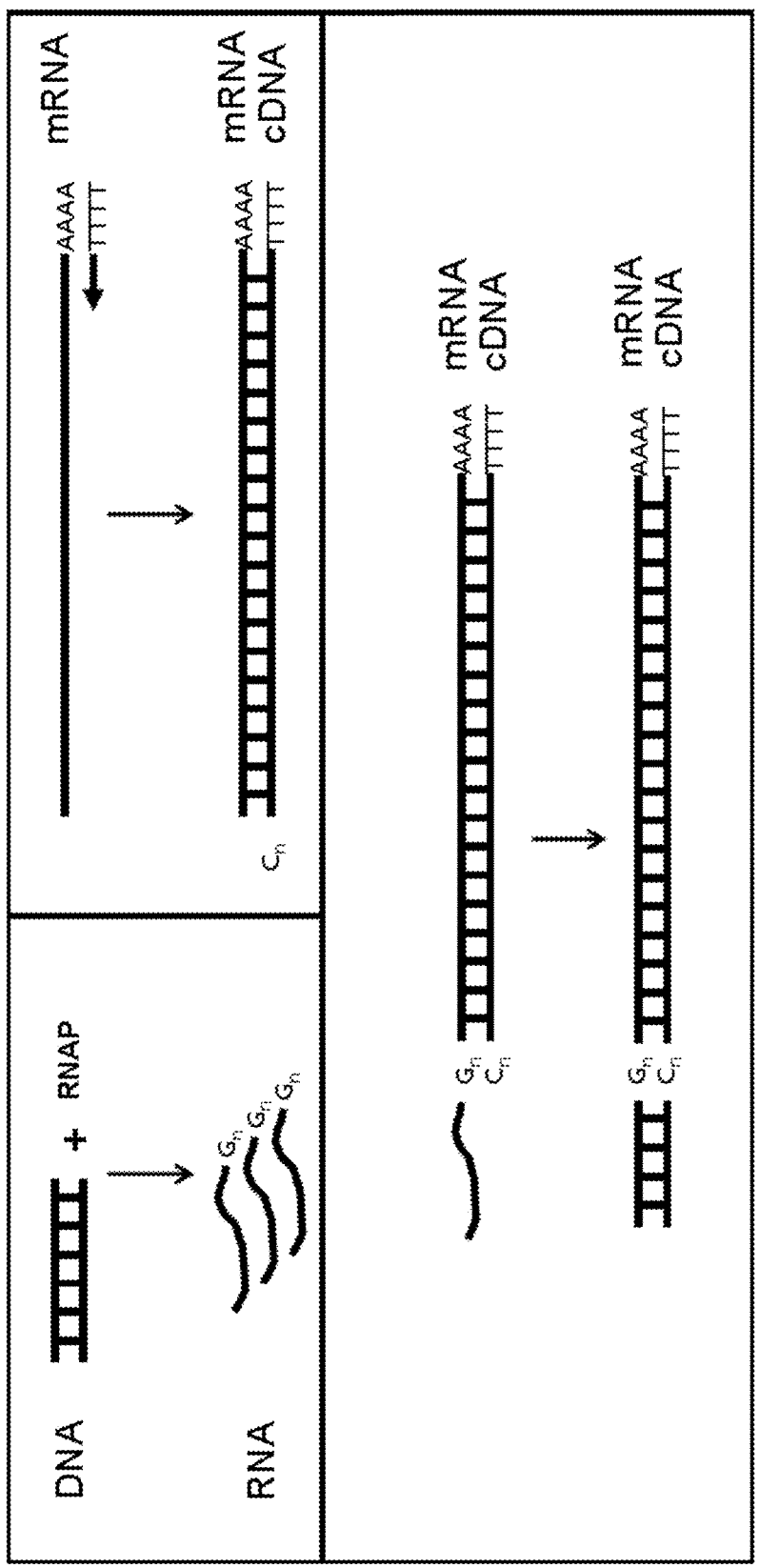
FIG. 3 shows the incorporation of barcode sequences into first strand cDNA according to some embodiments of the invention. Here RNA barcode adapters are synthesized to demonstrate barcoding of cDNA. DNA barcode adapters (synthesized in FIG. 2B) may also be used. An RNAP primes off its promoter and synthesizes RNA barcode adapters (FIG. 3, top left). In the same reaction, reverse transcription occurs and $1^{st}$ strand cDNA is generated (top right). The MMLV-based H-reverse transcriptase has 3' tailing activity and adds several dCs to the 3' end of the $1^{st}$ strand cDNA.
Figure 4:
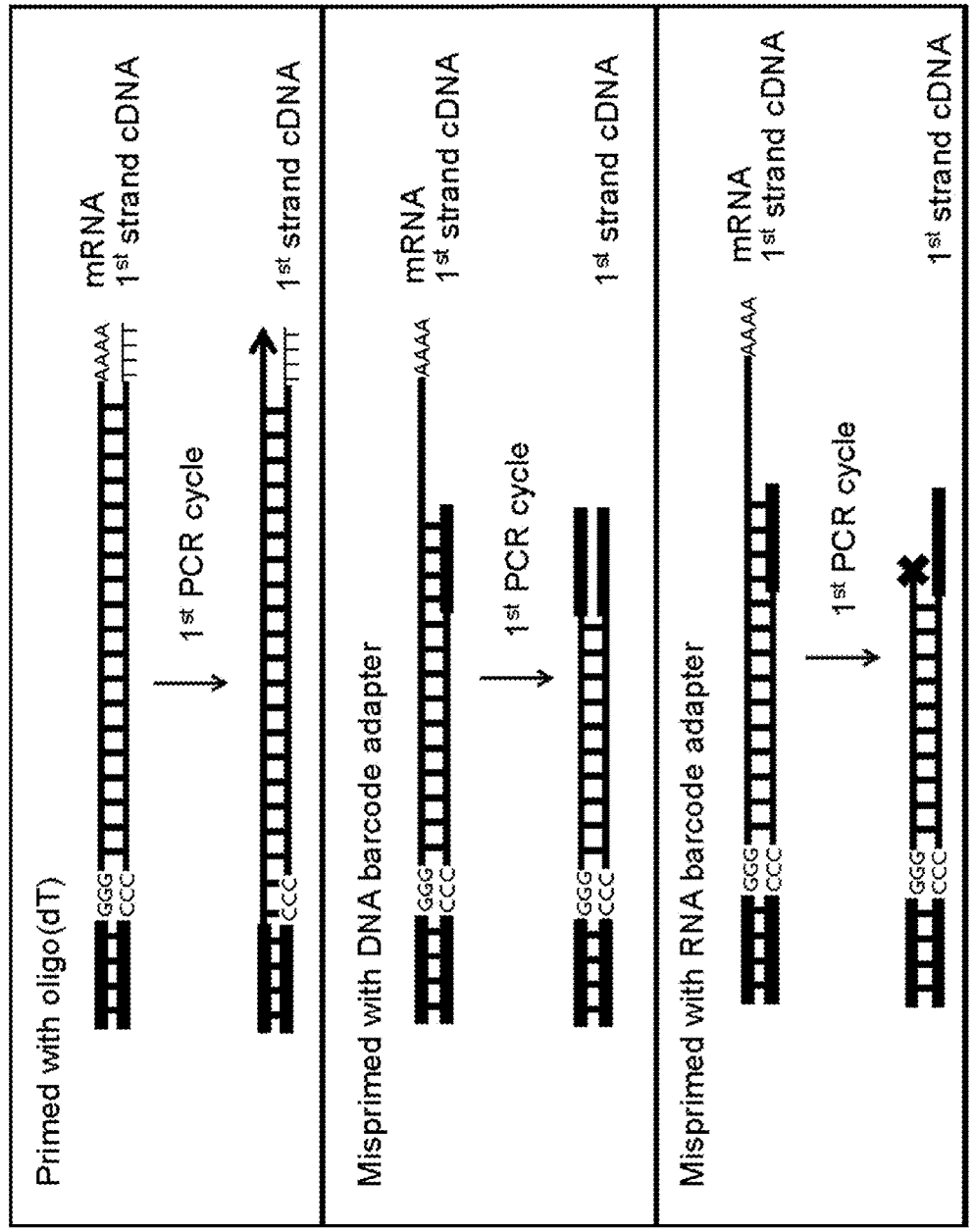

FIG. 4 shows that RNA barcode adapters have less background than DNA barcode adapters in embodiments of the invention. In the barcoding reaction in FIG. 3, both oligo(dT) and barcode adapters are present, and both oligos can prime the reverse transcription reaction. When the reaction is primed with oligo(dT) (FIG. 4, top), the reaction proceeds as normal. When the RT reaction is misprimed with a DNA barcode adapter (middle), during PCR the forward primer can prime off both the sense and anti-sense strands and create amplification of non-desired products. When the RT reaction is primed with RNA barcode adapter (bottom), the growing strand cannot use RNA nucleotides as a template when using a proof-reading DNA polymerase in PCR1, and as a result misprimed cDNAs will not contain barcode adapter sequences on both the sense and anti-sense strands. Therefore non-desired products should not be exponentially amplified, resulting in significantly less background.

Figure 5A:
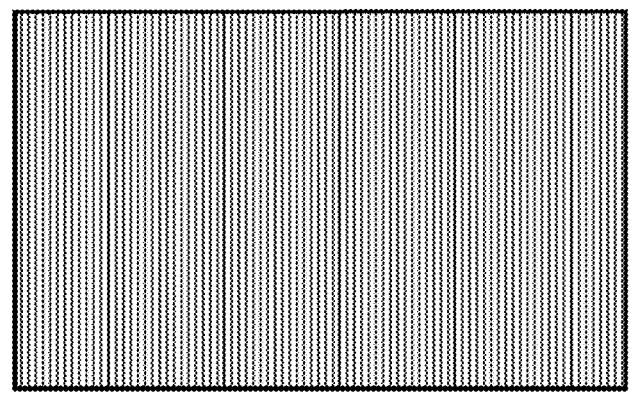
Figure 5B:
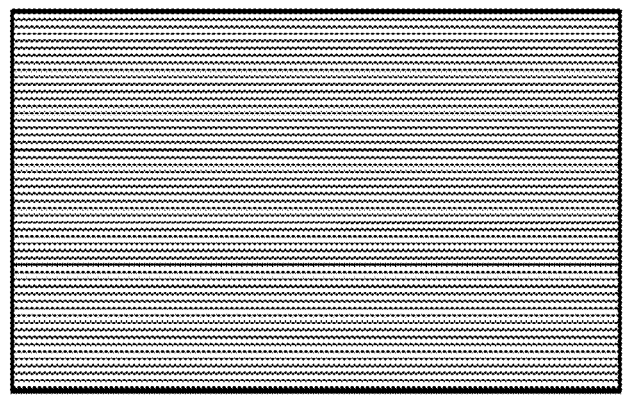
Figure 5C:
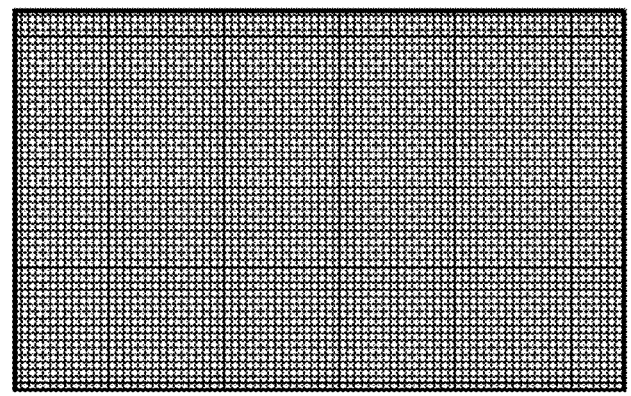

FIGS. 5A-C are cartoons illustrating the segregation of reaction volumes for generating barcode adapters and performing reverse transcription, according to some embodiments of the present invention. Barcode adapter molecules can be enzymatically generated in a plurality of first reaction volumes, such as droplets, which are represented by the vertical lines in FIG. 5A. Each first reaction volume can contain barcode adapter molecules in aqueous solution, all with the same barcode sequence. Separately, RNA molecules can be reverse transcribed in a plurality of second reaction volumes, which are represented by the horizontal lines in FIG. 5B. Each second reaction volume can contain RNA molecules all derived from the same sample. The first and second reaction volumes can then be combined, such as by merging droplets, as represented by the crossed lines in FIG. 5C. The products of the reactions in FIGS. 5A and 5B are mixed together, such that one barcode sequence is introduced into the reaction volume corresponding to each sample. The barcode sequence can be incorporated into first-strand cDNA or PCR products.

Figure 6C:
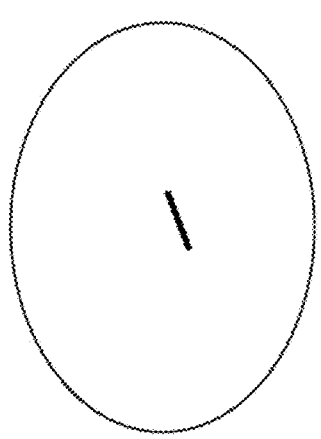
Figure 6D:
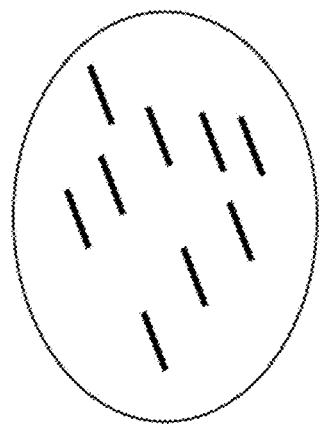
Figure 6A:
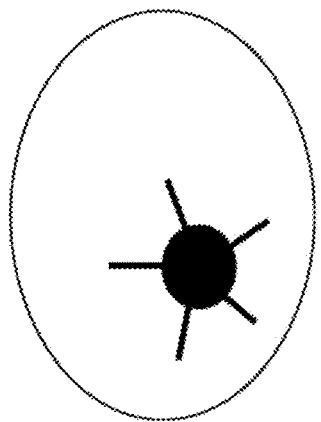
Figure 6B:
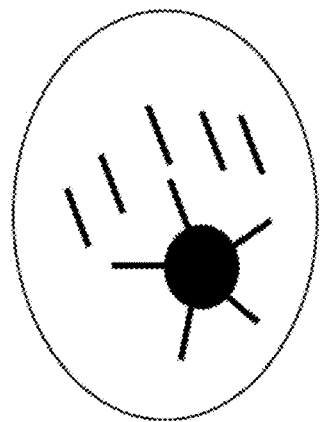

FIGS. 6A-D show the amplification of barcode adapter templates to produce barcode adapter molecules, in various embodiments of the invention. FIG. 6A shows barcode adapter templates attached to a solid surface, such as a bead. FIG. 6B shows barcode adapter molecules in aqueous solution, resulting from amplification of the barcode adapter templates in FIG. 6A. FIG. 6C shows a single barcode adapter template molecule. The molecule is in aqueous solution and is held inside a container. FIG. 6D shows the container of FIG. 6C with multiple barcode adapter molecules, which result from amplification of the single template molecule.

Figure 7A:
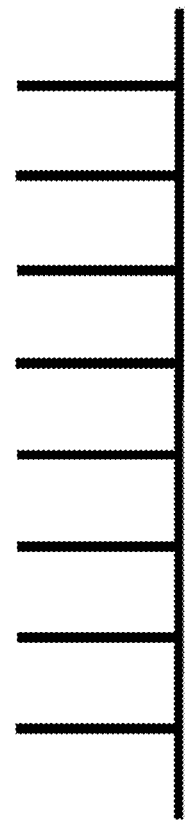
Figure 7B:
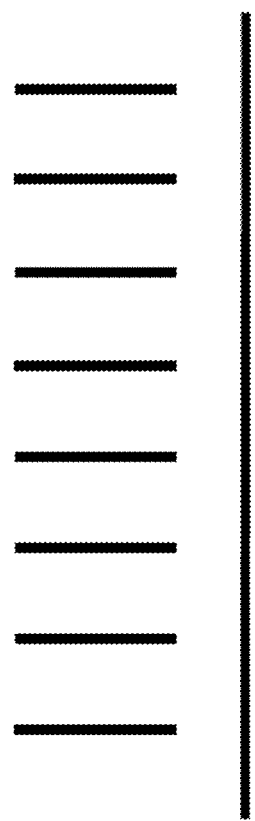
Figure 7C:
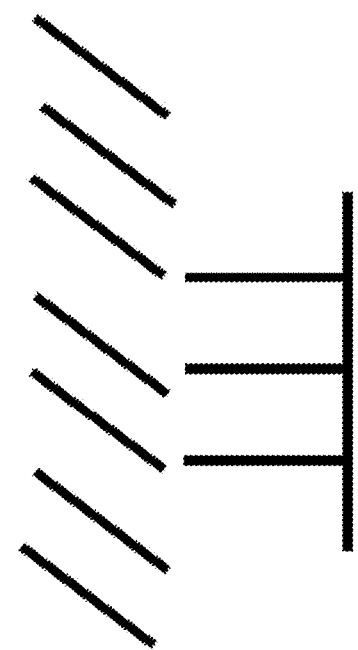
Figure 7D:
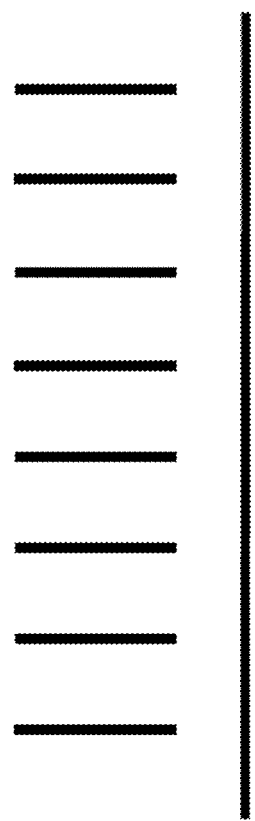

FIGS. 7A-D show the generation of barcode adapter molecules from templates, wherein the templates are attached to solid surfaces. Upon generation, the barcode adapter molecules are in aqueous solution. FIGS. 7A and 7B show barcode adapter templates attached to solid surfaces. FIG. 7C shows barcode adapter molecules amplified enzymatically from the barcode adapter templates in FIG. 7A. FIG. 7D shows barcode adapter molecules released into solution upon the chemical or enzymatic cleavage of the barcode adapter templates in FIG. 7B from the solid surface.

Figure 8:
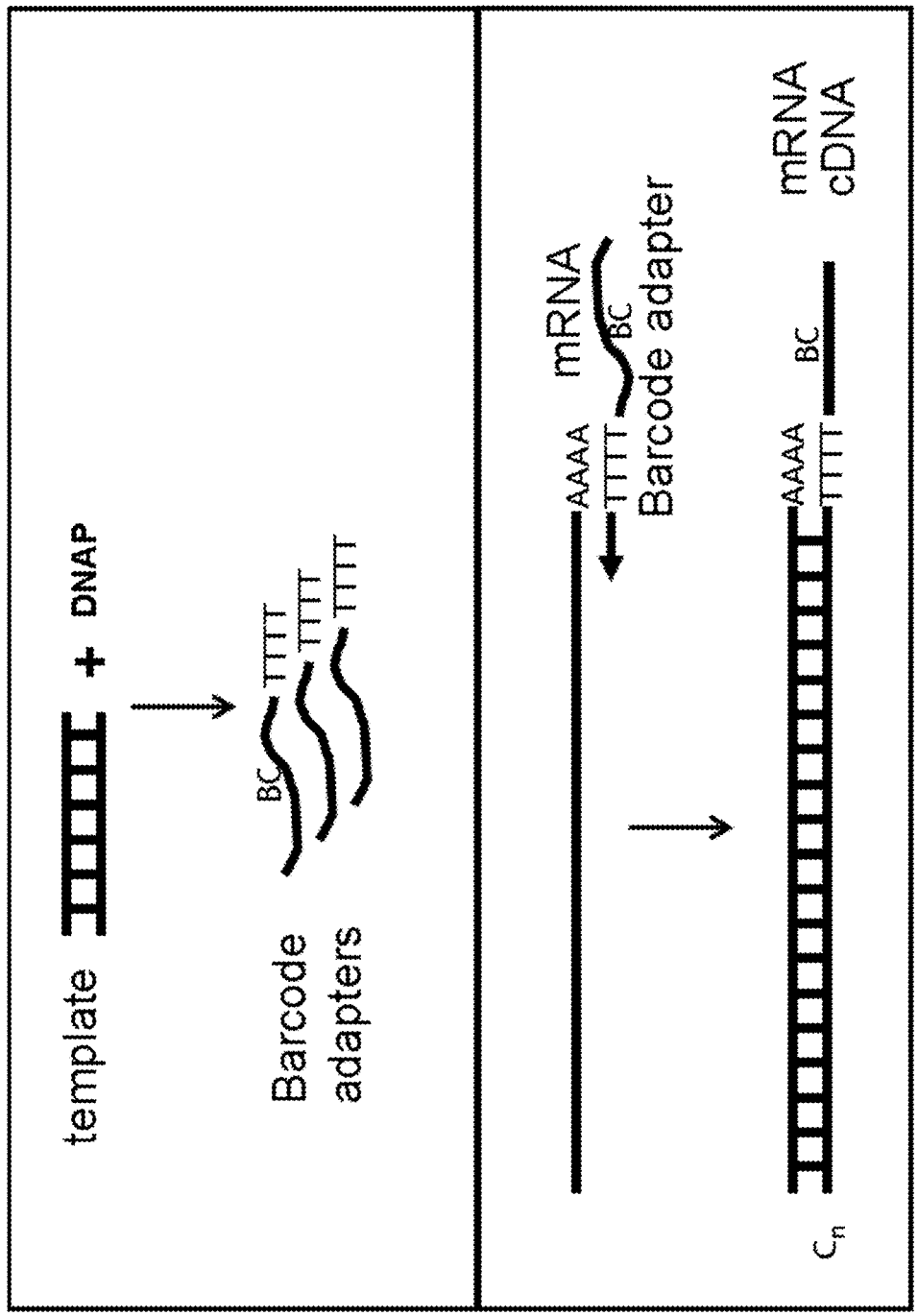

FIG. 8 shows incorporation of a barcode sequence into a first strand of cDNA using a DNA barcode adapter. (Top) The barcode adapter, including a 3' poly-T tract, is generated from a barcode adapter template using a DNA polymerase. Barcode adapter molecules are in aqueous solution. (Bottom) The barcode adapter anneals to the poly-A tail of an mRNA and serves as a primer for reverse transcription. The barcode sequence is incorporated into the 5' end of the first strand of cDNA.

Figure 9:
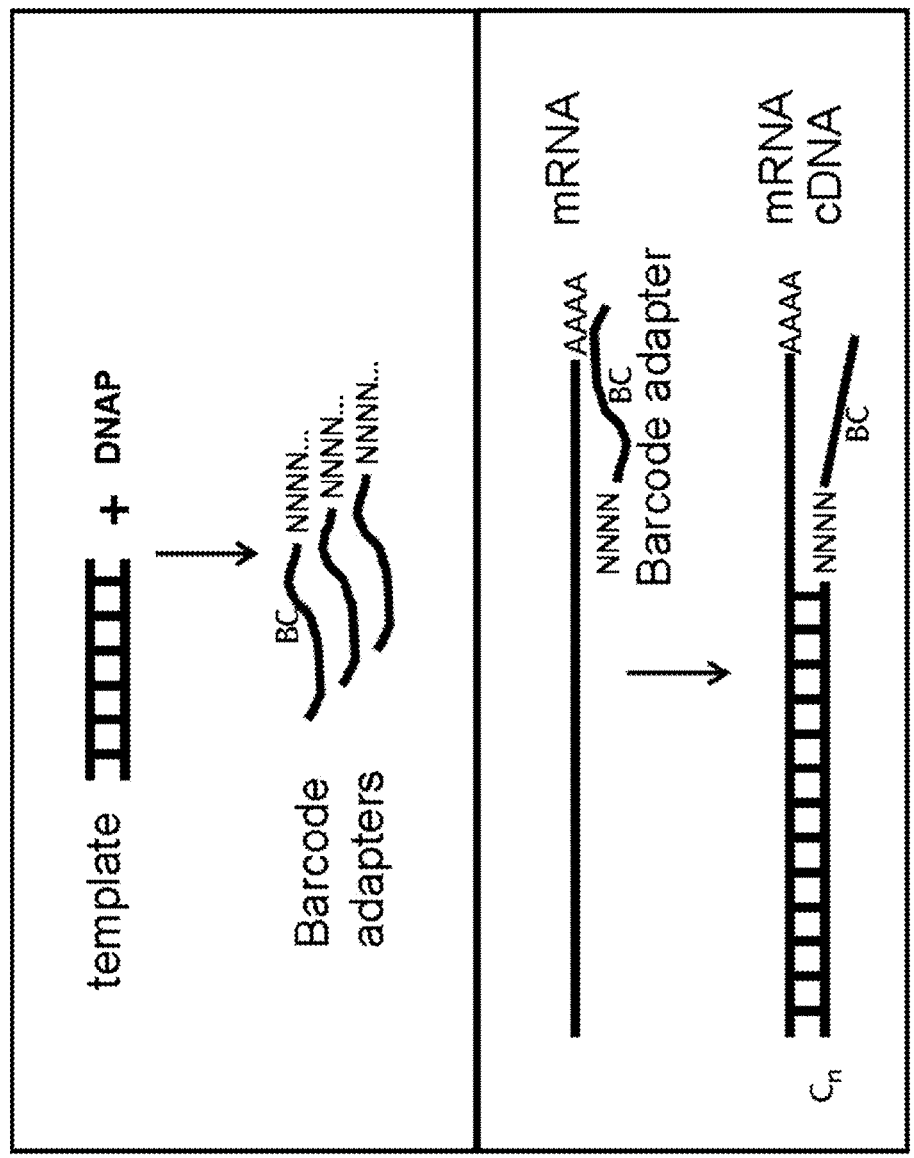

FIG. 9 shows incorporation of a barcode sequence into a first strand of cDNA using a DNA barcode adapter. (Top) The barcode adapter, including a 3' random or semi-random sequence tract, is generated from a barcode adapter template using a DNA polymerase. Barcode adapter molecules are in aqueous solution. (Bottom) The barcode adapter, by annealing to a region of an RNA that is at least partially complementary to the 3' sequence tract, serves as a primer for reverse transcription. The barcode sequence is incorporated into the 5' end of the first strand of cDNA.

Figure 10:
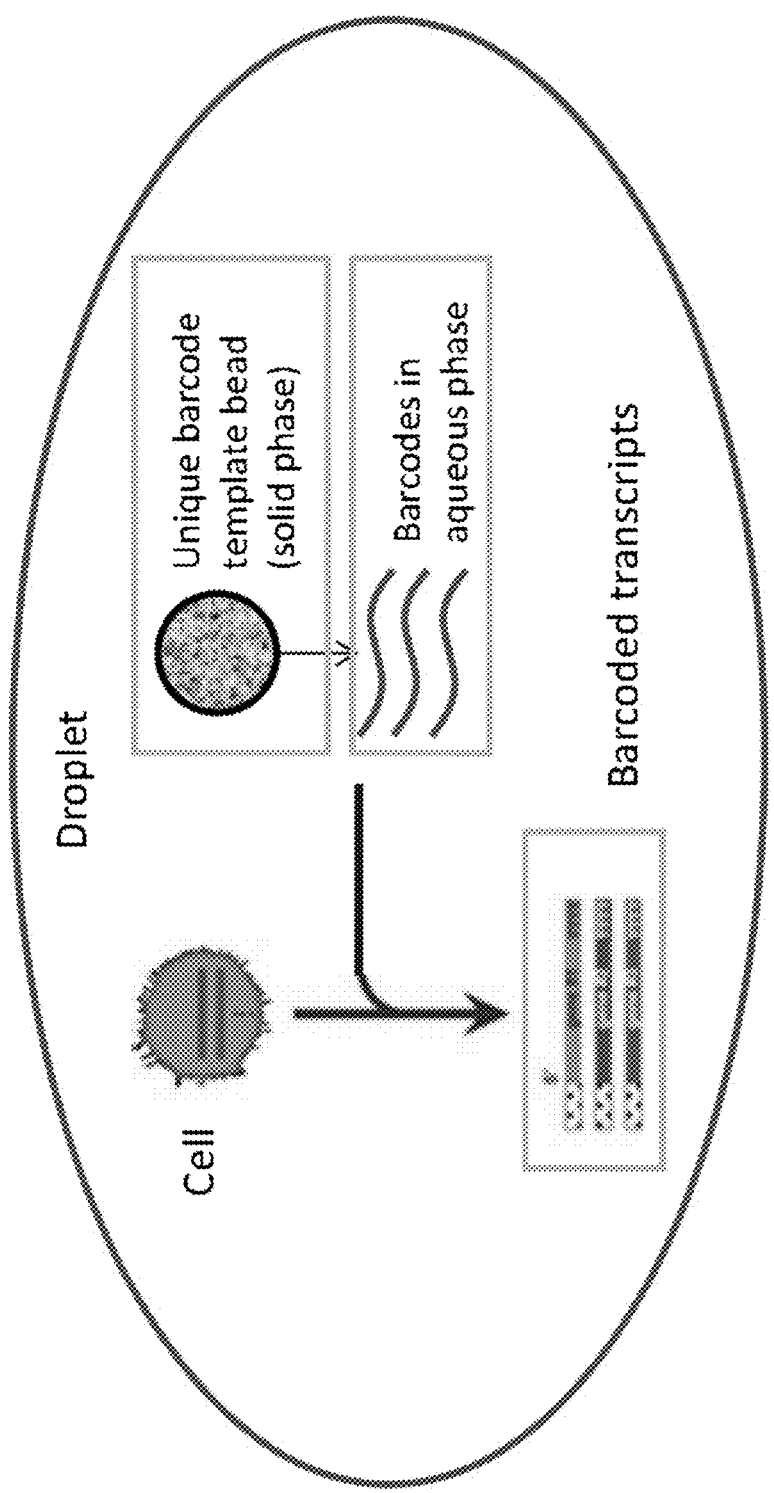

FIG. 10 is a schematic overview of a barcoding workflow that eliminates individual pipetting steps. In brief, barcoding reactions occur in water-in-oil droplets, where cells and beads containing barcode adapters are distributed by a droplet generating device. Barcode adapters are enzymatically amplified or released from a solid surface, such as a bead, and the barcodes are added to all transcripts from a cell.

Figure 11:
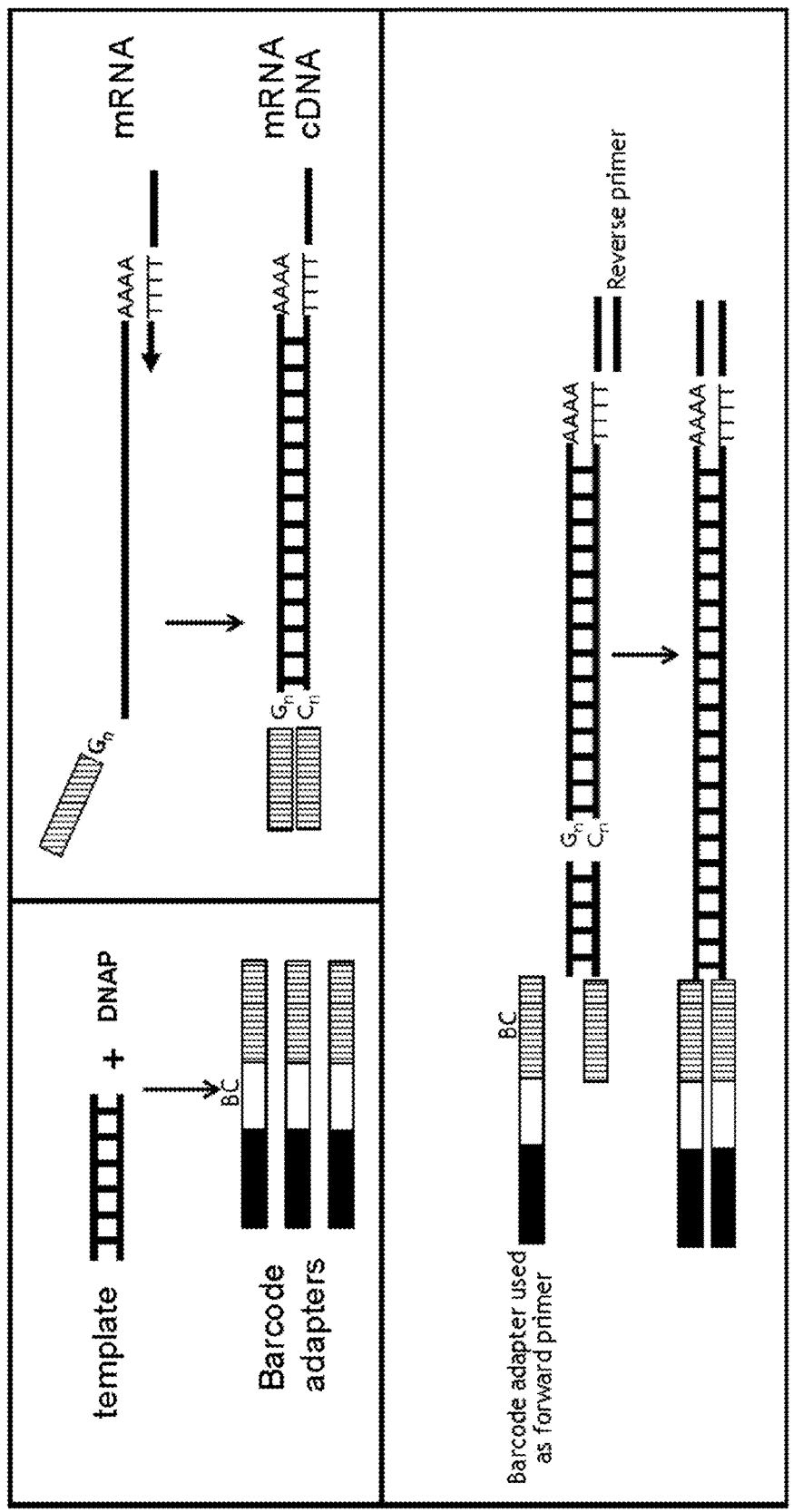

FIG. 11 shows incorporation of a barcode sequence into an amplicon using a DNA barcode adapter that serves as a forward primer for RT-PCR. The barcode adapter is generated enzymatically from a DNA template using a DNA polymerase (upper left). Barcode adapter molecules are in aqueous solution. In a separate reaction volume, or in the same reaction volume, a first strand of cDNA is synthesized (upper right) using an mRNA template, a reverse transcriptase, a primer containing a poly-T tract, and a template-switching oligonucleotide. The template-switching oligonucleotide contains a sequence region complementary to a sequence region in the barcode adapter. The barcode sequence is then incorporated into an amplicon during PCR amplification of the cDNA (bottom). The barcode adapter serves as a forward primer for PCR.

Figure 12:
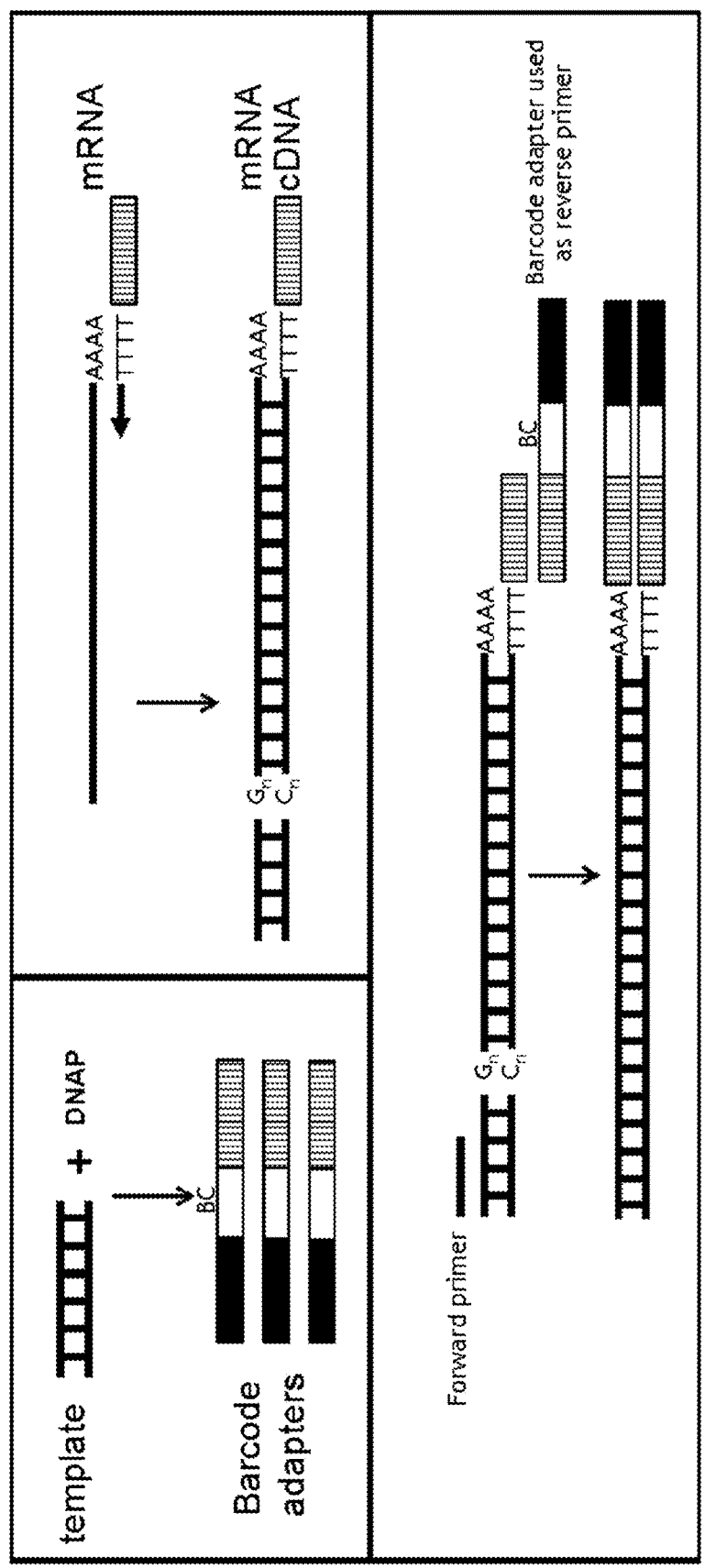

FIG. 12 shows incorporation of a barcode sequence into an amplicon using a DNA barcode adapter that serves as a reverse primer for RT-PCR. The barcode adapter is generated enzymatically from a DNA template using a DNA polymerase (upper left). Barcode adapter molecules are in aqueous solution. In a separate reaction volume, or in the same reaction volume, a first strand of cDNA is synthesized (upper right) using an mRNA template, a reverse transcriptase, a primer containing a poly-T tract, and a template-switching oligonucleotide. The primer contains a 5' sequence region complementary to a 3' sequence region in the barcode adapter. The barcode sequence is then incorporated into an amplicon during PCR amplification of the cDNA (bottom). The barcode adapter serves as a reverse primer for PCR.

Figure 13:
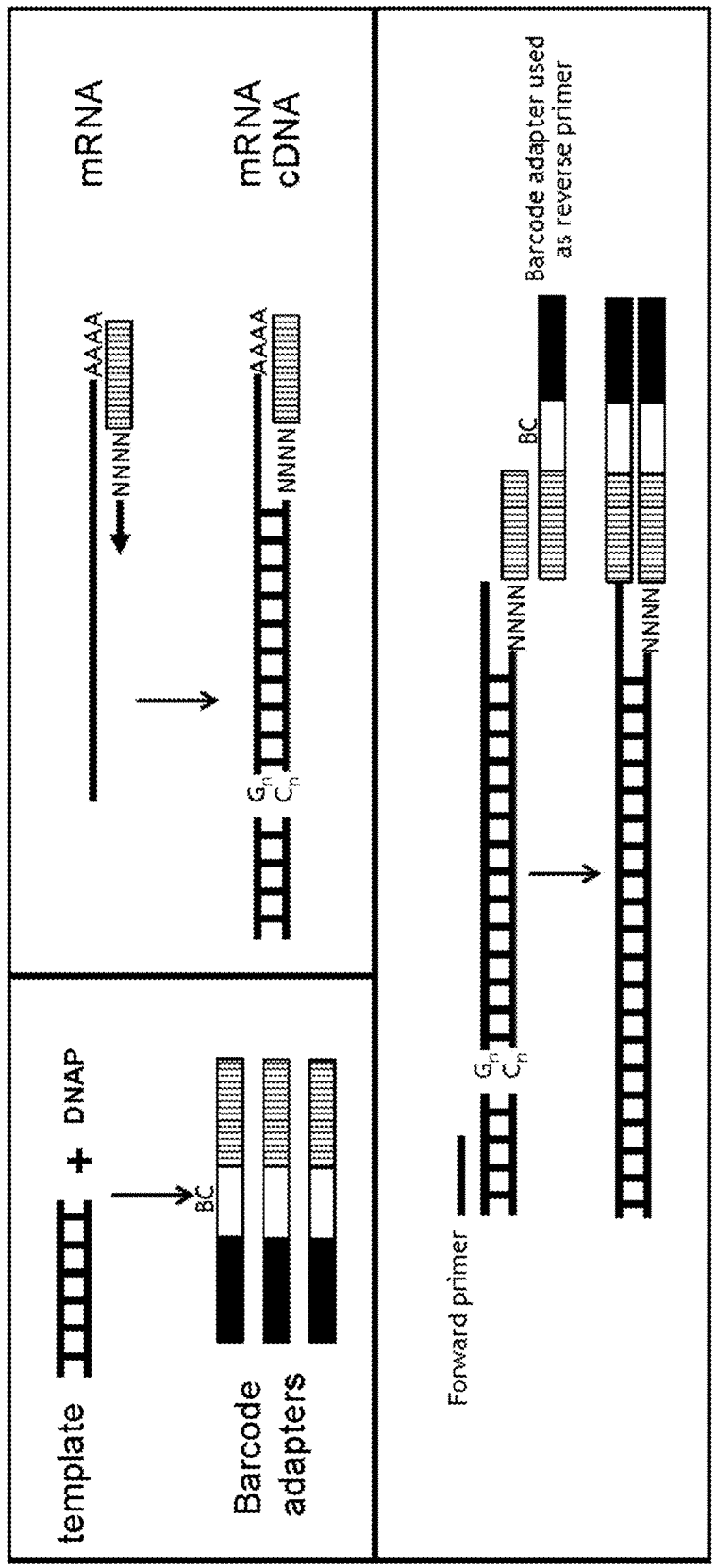

FIG. 13 shows incorporation of a barcode sequence into an amplicon using a DNA barcode adapter that serves as a reverse primer for RT-PCR. The barcode adapter is generated enzymatically from a DNA template using a DNA polymerase (upper left). Barcode adapter molecules are in aqueous solution. In a separate reaction volume, or in the same reaction volume, a first strand of cDNA is synthesized (upper right) using an mRNA template, a reverse transcriptase, a primer containing a 3' random sequence tract, and a template-switching oligonucleotide. The primer can anneal to the mRNA through the random sequence tract, and also contains a 5' sequence region complementary to a 3' sequence region in the barcode adapter. The barcode sequence is then incorporated into an amplicon during PCR amplification of the cDNA (bottom). The barcode adapter serves as a reverse primer for PCR.

Figure 14C:
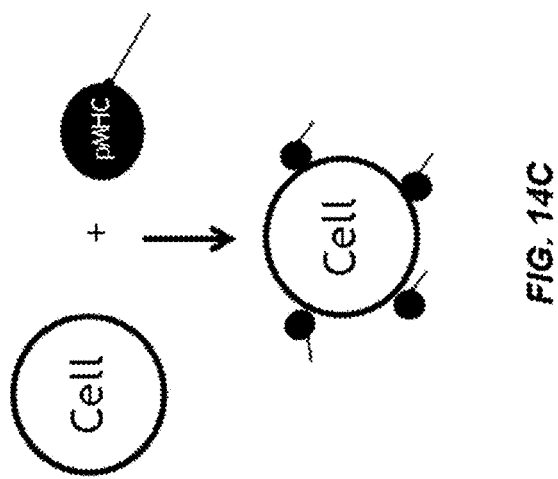
Figure 14B:
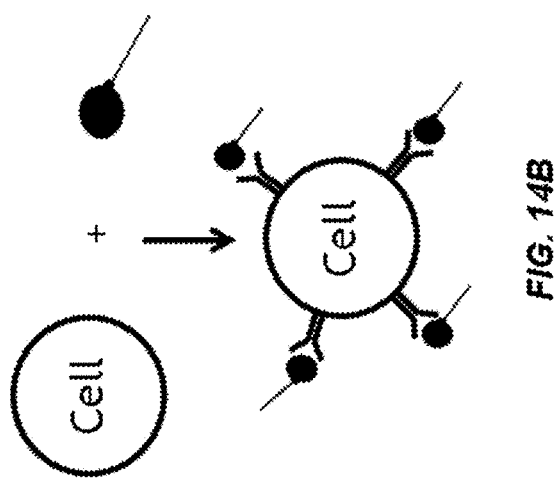
Figure 14A:
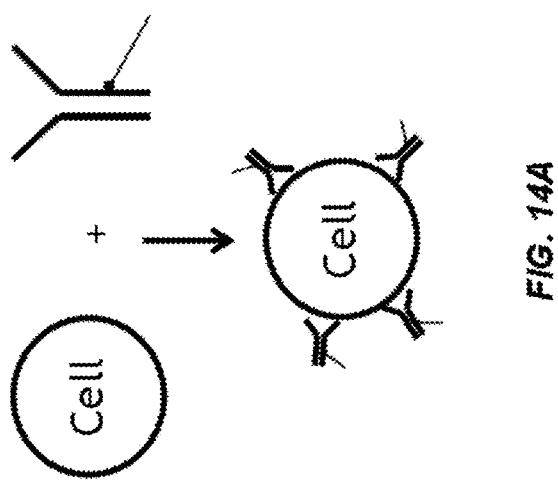

FIG. 14A-C illustrates methods of interrogating a population of cells for a selected phenotype using a nucleic acid marker, according to embodiments of the present invention. In addition to barcoding RNA from cells, any RNA, including RNA from non-cell sources, can be barcoded. Non-cell RNA may be introduced into reaction volumes by any means, such as by labeling cells with a nucleic acid marker. This marker can include a nucleic acid coupled to a molecular label, such as an antibody (FIG. 14A), an antigen (FIG. 14B), or pMHC (FIG. 14C). The nucleic acid marker can bind to some or all cells in the population, depending on the phenotypes of the cells and their affinities for the molecular label. All cells in the population can then be lysed and mRNAs in each cell can be barcoded. For cells that bind the nucleic acid marker, the associated nucleic acid can be barcoded as well. This nucleic acid can be an RNA, or a dsDNA template with an RNAP promoter, such as a T7, T3 or SP6 promoter. Sequencing can then associate non-endogenous RNA sequences with specific cells, thereby detecting which cells bound to the molecular label. Different molecular labels can be coupled to different nucleic acid sequences, enabling identification of multiple cellular phenotypes.

Figure 15:
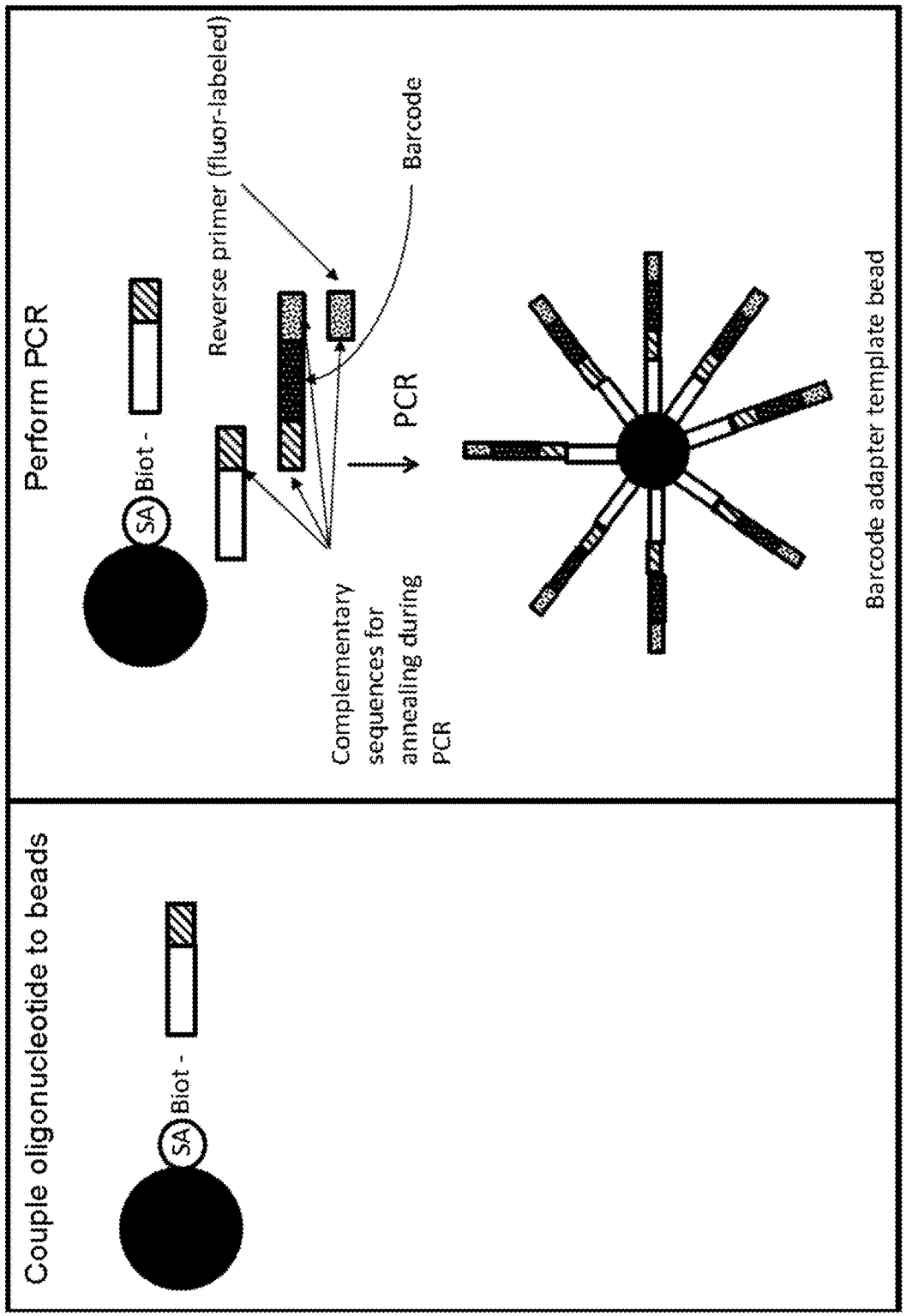

FIG. 15 shows synthesis of barcode adapter template beads in one reaction according to some embodiments of the invention. (Left) Beads are coupled to an oligonucleotide. Coupling may be done by coupling biotinylated oligos onto streptavidin coated beads, and may also be coupled using other means known in the field. (Right) Coupled beads, forward and reverse primers, and a barcode oligo containing a barcode sequence and sequences complementary to the forward and reverse primers are all present in a reaction container, with the barcode oligo preferably present at only a single copy. PCR is then conducted to amplify the barcode sequence and incorporate it into the bead-coupled oligonucleotides to form barcode adapter template beads.

Figure 16:
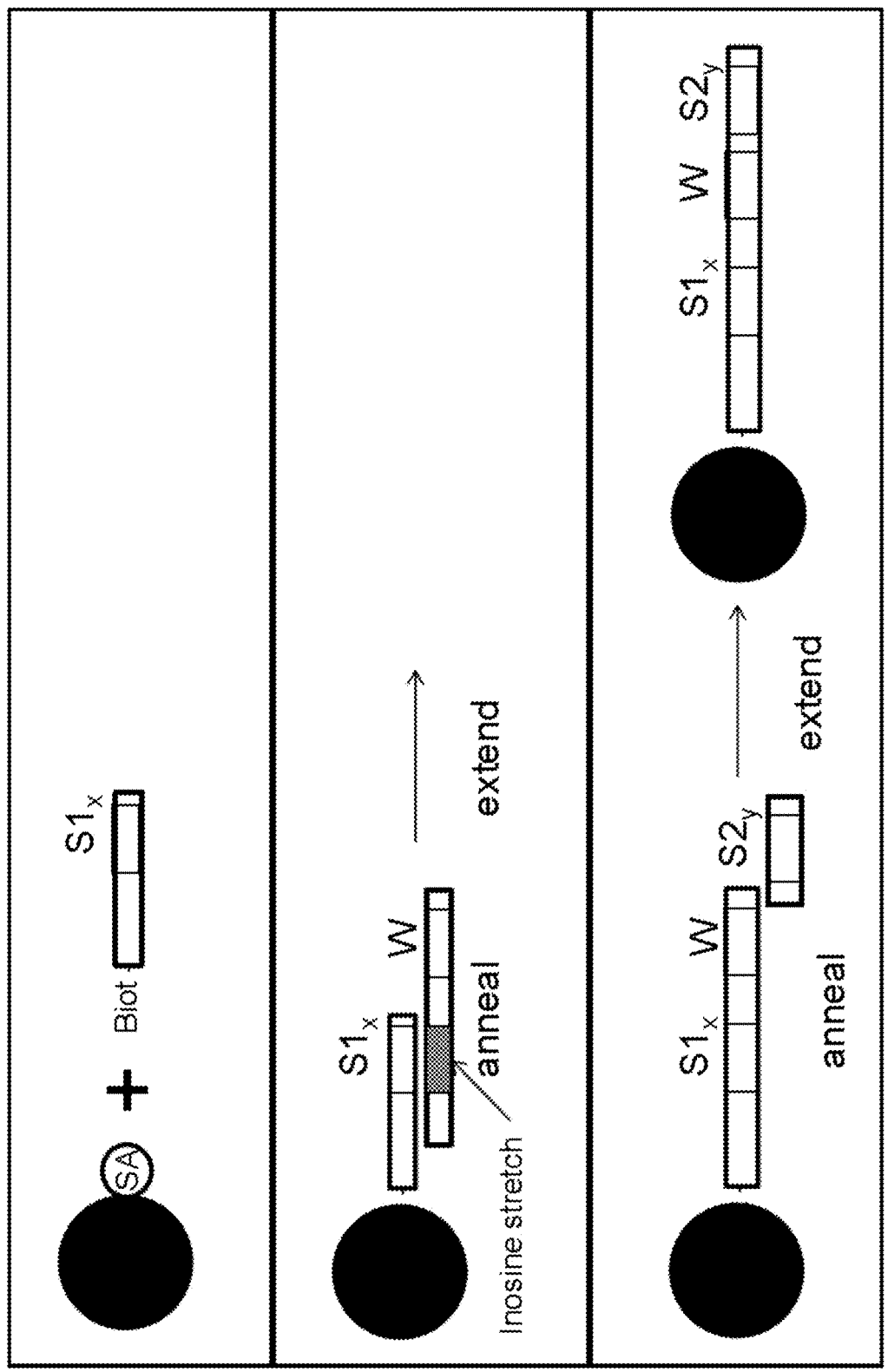

FIG. 16 shows synthesis of barcode adapter template beads in multiple steps according to some embodiments of the invention. (Top) Beads are coupled to (multiple copies of) an oligonucleotide containing a unique S1 sequence. Multiple, separate coupling reactions are performed, with each coupling reaction using an oligonucleotide containing a different unique S1 sequence. Beads, each coupled to an oligonucleotide with a different unique S1 sequence, are then pooled together, forming a library of beads having $S1_x$ sequences. (Middle) These beads are then used in an extension reaction. In each reaction, an oligonucleotide that contains a unique W sequence complementarily base-pairs with the $S1_x$-containing oligonucleotide coupled to the bead, and an extension reaction using a DNA polymerase is performed. Beads from all the extension reactions are pooled, and a library of beads containing a combination of $S1_x$ sequences each with the unique W sequence are formed. (Bottom) The double-stranded DNA from the previous step is denatured and the antisense strand washed off the beads. Additional, separate extension reactions are performed on the beads as before, but the oligonucleotide that complementarily base-pairs with the $S1_x$ and W containing oligonucleotide coupled to the beads contains a different unique S2 sequence in each separate reaction. Beads from all extension reactions are pooled, and a library of beads containing barcode adapter templates is obtained, with a combination of $S1_x$, W, and $S2_y$ sequences forming the barcode sequence. A large number of unique barcode sequences can thus be obtained in this combinatorial approach. Furthermore, multiple unique W sequences can each be combined with the $S1_x$ and $S2_y$ sequences, yielding barcodes of the general format $S1_x$-$W_z$-$S2_y$.

Figure 17:
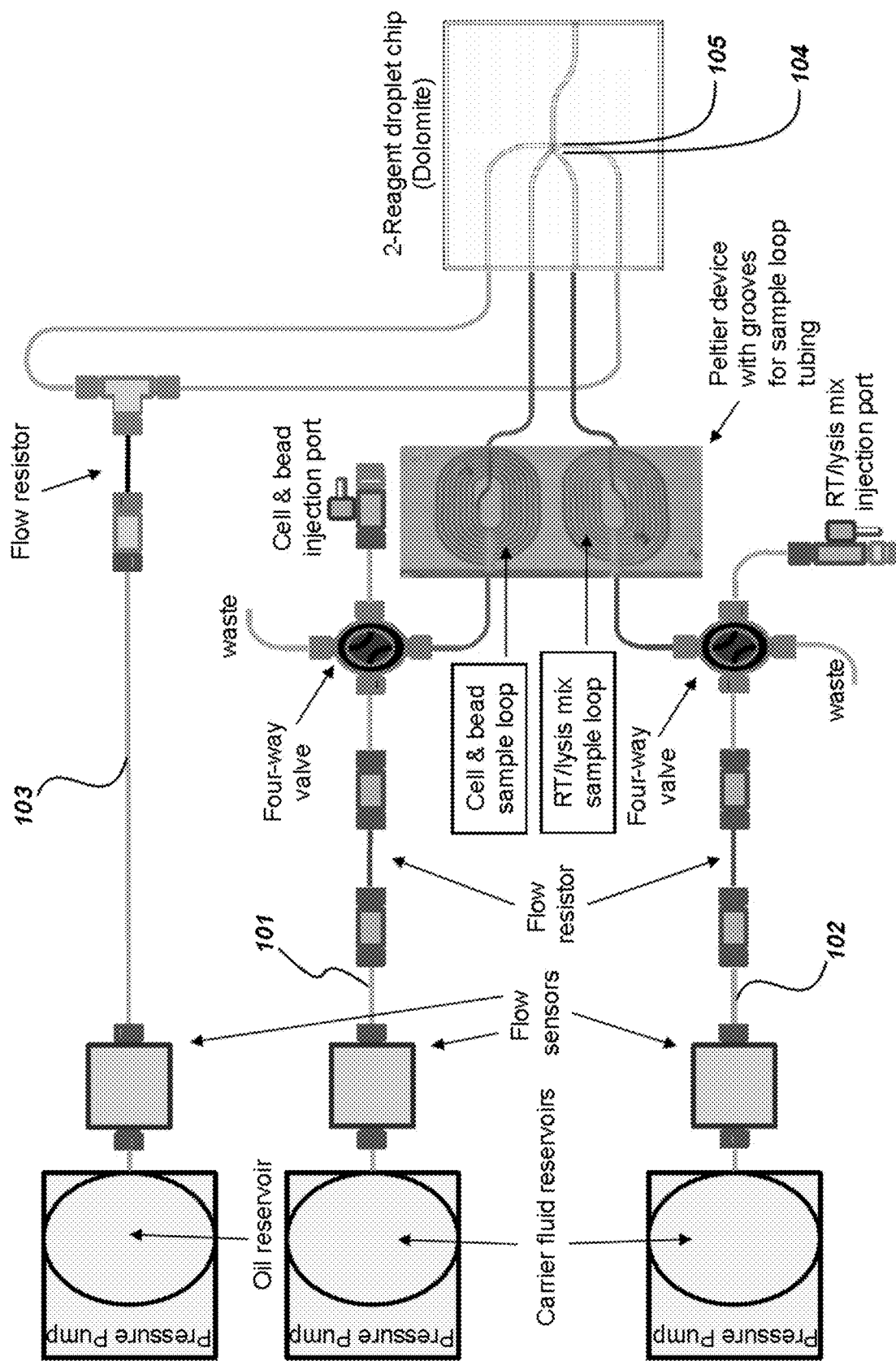

FIG. 17 shows a droplet device according to embodiments of the invention. Three Dolomite P-Pumps are equipped with flow sensors. The first P-Pump is connected directly to a 2-Reagent Droplet Chip via microfluidic tubing that incorporates a T-junction to split the line into two inputs. This is the oil input line. The other two P-Pumps are connected via fluidic tubing to FEP sample loops that fit into the grooves of a Peltier device used to keep samples chilled while the device is operating, and each of these loops is connected to the 2-Reagent Droplet Chip. Each sample loop incorporates a four-way valve at its front end so that sample can be loaded into the loop by means of a syringe. The first sample loop is to be filled with the cell and barcoded bead suspension while the second loop is to be filled with RT/lysis mix. The sample loops can be oriented horizontally and above or level with the droplet chip so as to avoid any uphill sections through which it may be difficult for cells and beads to travel.

Figure 18:
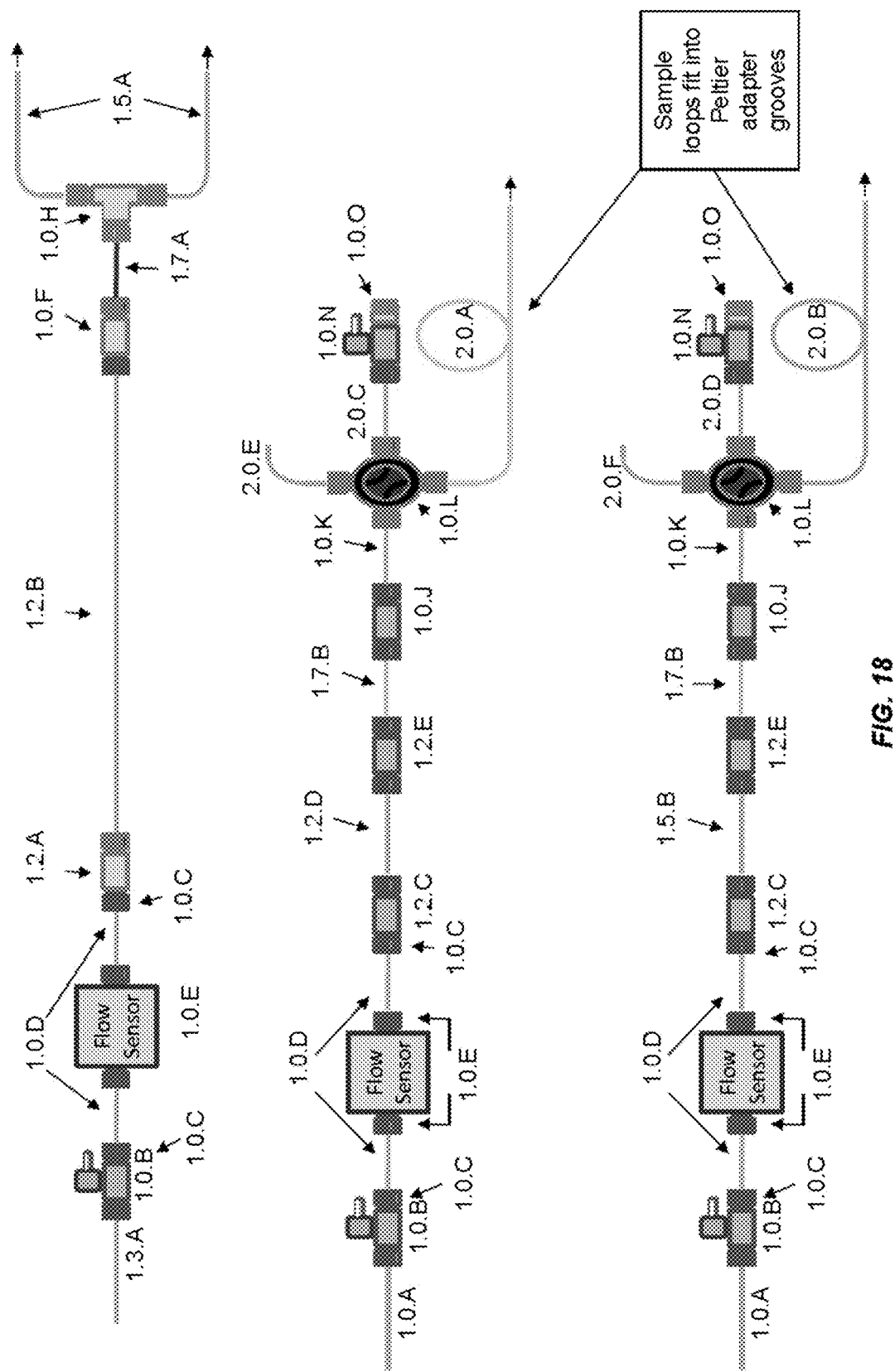

FIG. 18 provides details of the configuration of the droplet device shown in FIG. 17. Parts given by IDEX H&S part number: 1.0.A) 1528 (110 mm); 1.0.B) P-732; 1.0.C) P-232/P-248; 1.0.D) 1688 (300 mm); 1.0.E) M-645; 1.0.F) P-630; 1.0.H) P-632; 1.0.J) P-702; 1.0.K) 1529 (50 mm); 1.0.L) V-101D; 1.0.N) P-732; 1.0.O) P-624; 1.0.T) 1531 (900 mm); 1.2.A) P-630; 1.2.B) 1516 (500 mm); 1.2.C) P-702; 1.2.D) 1529 (150 mm); 1.2.E) P-702; 1.2.G) 1560 (150 mm); 1.3.A) 1528 (135 mm); 1.5.A) 1516 (150 mm); 1.5.B) 1529 (300 mm); 1.7.A) 61005; 1.7.B) 65020; 2.0.A) 1477 (1254 mm); 2.0.B) 1527 (1254 mm); 2.0.C) 1520 (120 mm); 2.0.D) 1520 (600 mm); 2.0.E) 1520 (200 mm); 2.0.F) 1520 (200 mm). Exit tubing (from the chip to the sample collection tube) is 180 mm of 1562.

Figure 19:
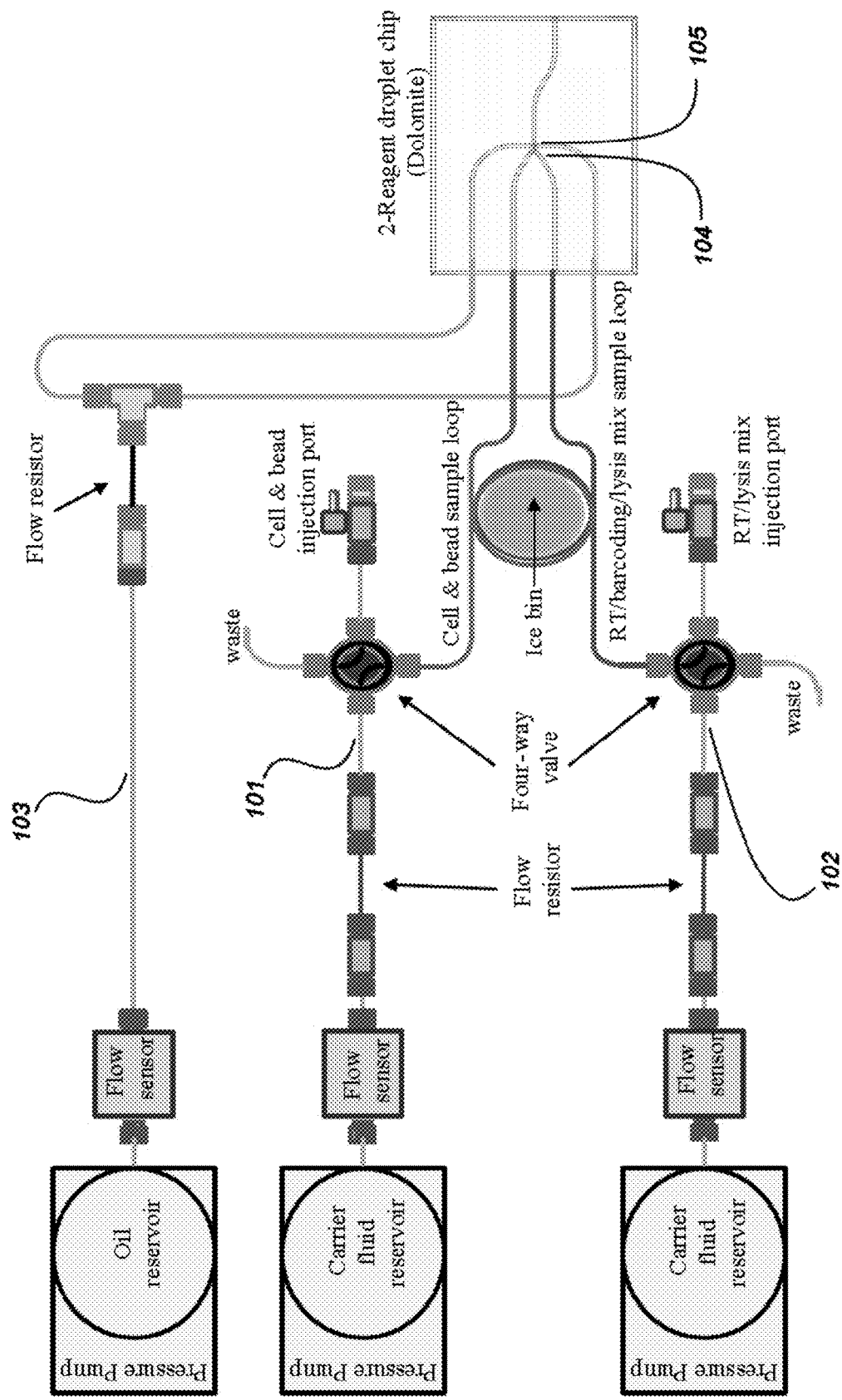

FIG. 19 shows an alternative embodiment of the droplet device described herein. The sample loops are in contact with an ice bin.

Figure 20:
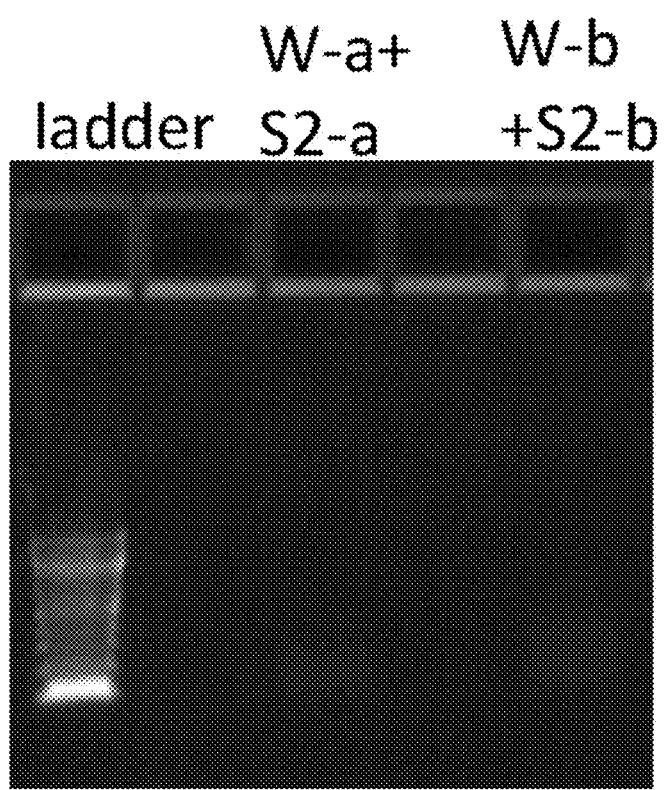

FIG. 20 shows RNA barcode adapters amplified from barcode adapter template beads, which were made using a multi-step approach. Barcode adapter template beads were used in an in vitro transcription reaction. Bands were present from beads made using S1-oligo+W-oligo-a+S2-oligo-a and S1-oligo+w-oligo-b+S2-oligo-b respectively.

Figure 21:
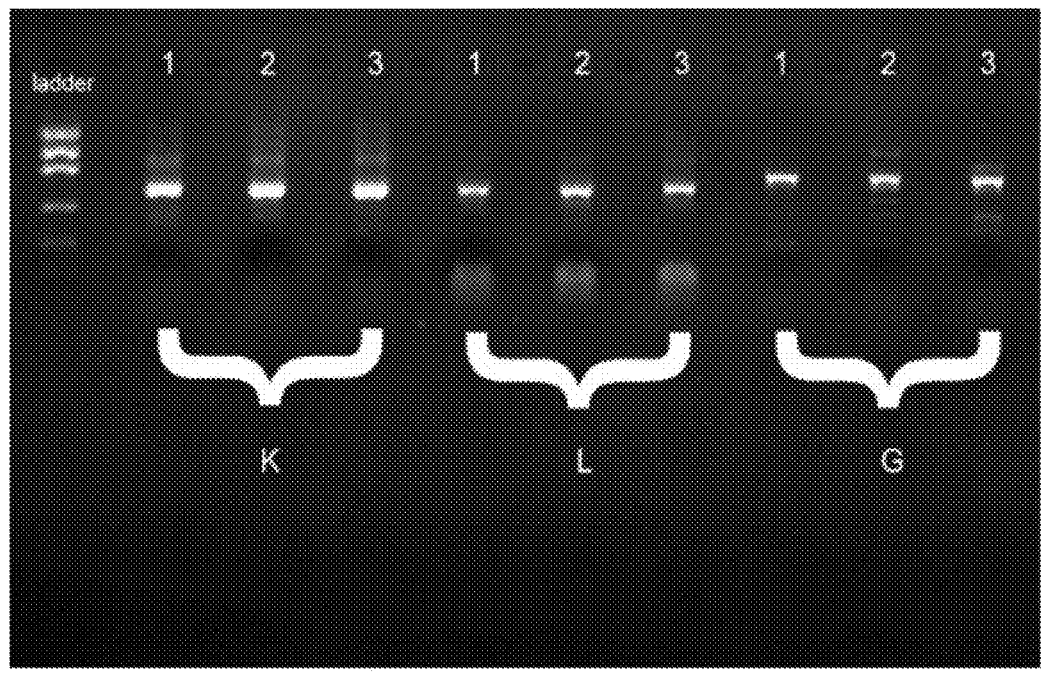

FIG. 21 shows a barcoding reaction performed in a variety of buffers. 1, 2, and 3 refer to three reaction buffers, which were respectively the 0.5×MMLV, 1× Thermopol DF and 0.5×TAE buffers described below. K, L, and G refer to kappa, lambda and gamma immunoglobulin chains. All chains were amplified in the different reaction buffers used.

Figure 22:
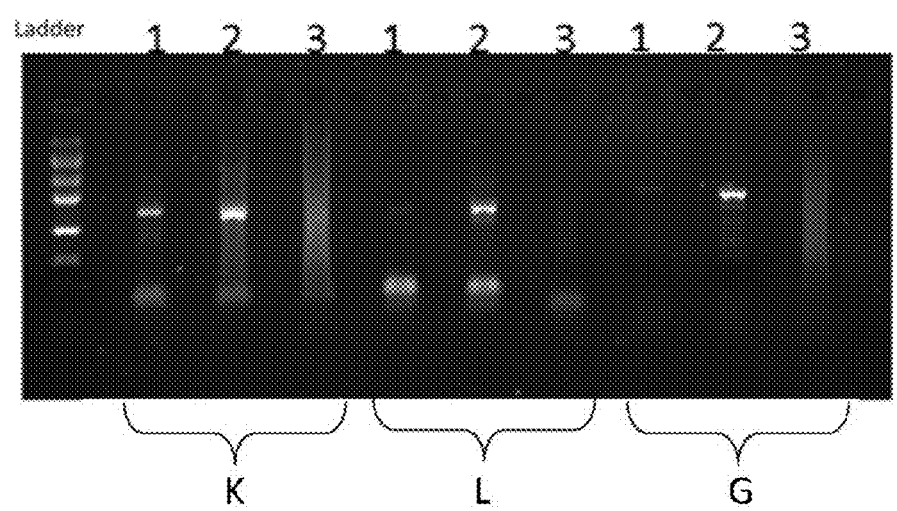

FIG. 22 shows that a barcoding reaction works better using RNA barcodes. 1, 2, and 3 refer to three reaction conditions, which were the 1×MMLV and 0.5×MMLV conditions using RNA barcode adapters, and 1×MMLV using DNA barcode adapters. K, L, and G refer to kappa, lambda and gamma immunoglobulin chains. The bands in the reaction using DNA adapters were obscured due to high background.

Figure 23:
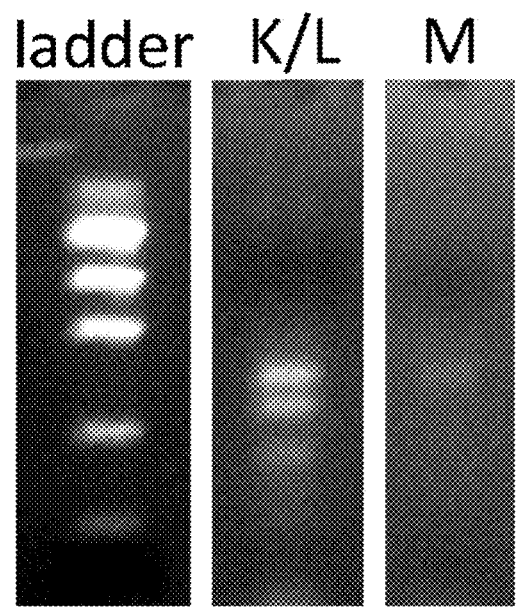

FIG. 23 shows amplified products from barcoding single B cells in droplet reaction containers with barcode adapter templates. The bands corresponding to kappa and lambda light chains ("K/L") and mu heavy chain ("M") can be clearly seen.

Figure 24:
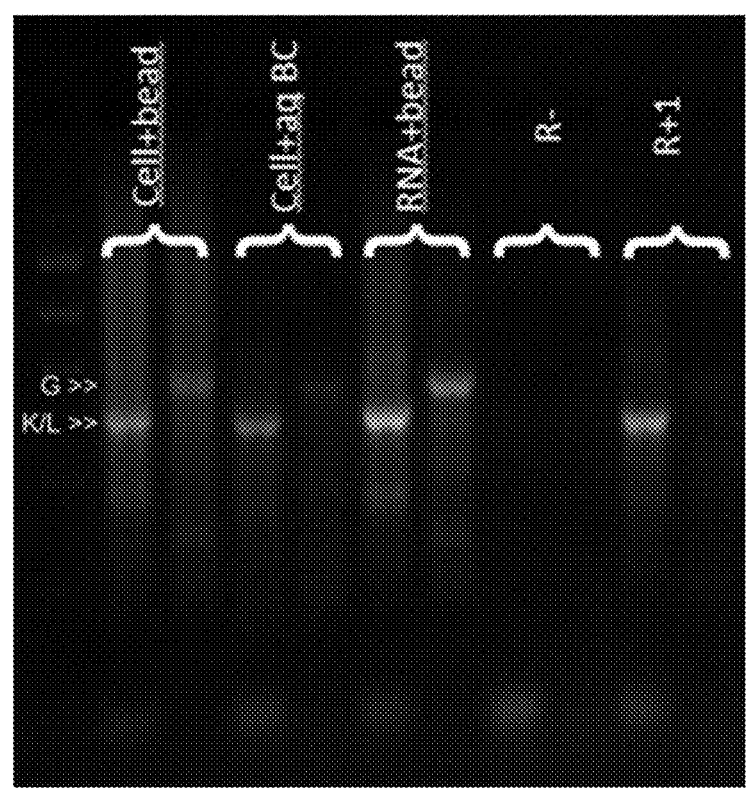

FIG. 24 shows RT/PCR amplification of light-chain (kappa/lambda) and heavy-chain (gamma) targets following co-encapsulation with barcoded beads in an aqueous-in-oil emulsion. Each sample is run in paired lanes—one for kappa/lambda light chain (left) and one for gamma heavy chain (right). Emulsion samples included the cell+bead co-encapsulated experimental sample (Cell+bead), as well as two control samples prepared identically except that in one, barcode template adapter beads were replaced with aqueous barcode adapter templates (Cell+aq BC), and one in which the cells were replaced with purified human PBMC RNA template obtained from AllCells (RNA+bead). Bulk positive and negative controls, which did not enter the emulsion device (R− and R+1 Respectively), were also included. Product bands were visible for the experimental sample and all positive controls, and were absent in the negative control.

Figure 25:
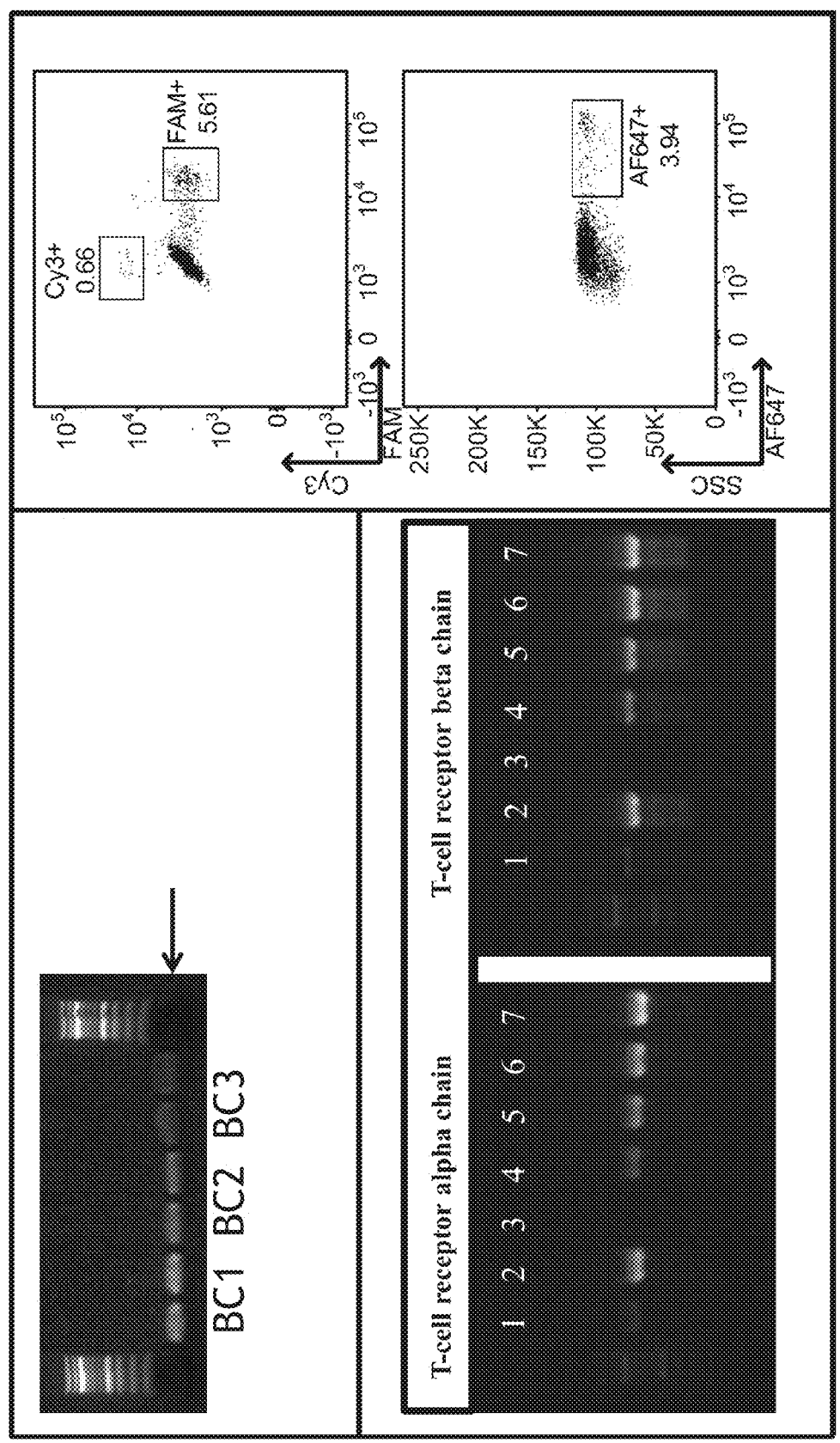

FIG. 25 illustrates methods of making barcode adapter template beads using multiple barcode adapter template types. Barcode-containing oligos were successfully generated with the expected length of 82 bp (upper left). Monocolor barcode adapter template beads were successfully obtained (right). The top graph was first gated on AF647- beads and the bottom graph was first gated on FAM-Cy3- beads so that the gates drawn in both graphs showed only monocolor beads. Beads were successfully used for barcoding RNA (lower left). Here, T cell receptor alpha and beta chains were successfully barcoded and amplified. Previously-generated beads were used as positive controls (lanes 1-2), and mono color barcode adapter template beads (lanes 4-7) were compared with a negative control (lane 3). DNA was analyzed on a 2% agarose gel, with a 100 bp ladder loaded in the left lane.

Figures 26, 27:
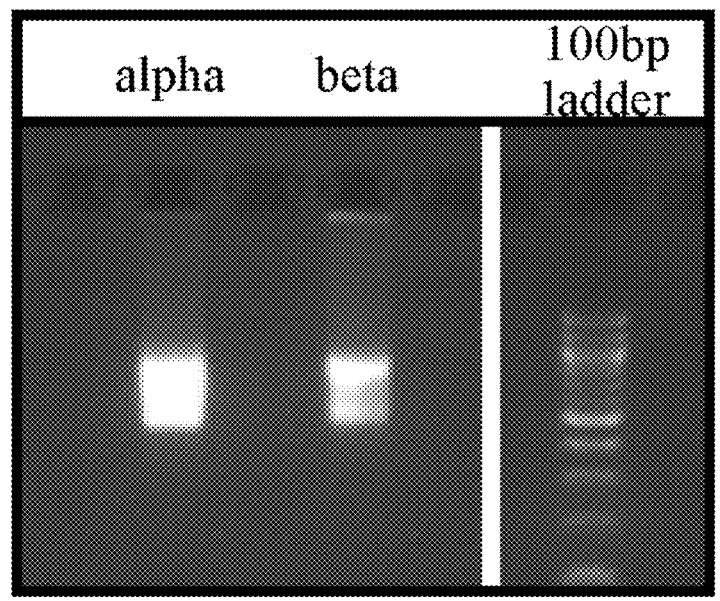

FIG. 26 illustrates efficient barcoding of T cell receptor alpha chain by encapsulating barcode adapter template beads and cells in droplets of varying sizes. Barcoded RNA was amplified after barcoding and analyzed on a 2% agarose gel.

FIG. 27 shows library PCR amplification products of TCR alpha and beta chains. Products were visualized on a 2% agarose gel. A 100 bp ladder was loaded in the right lane.

Figure 28:
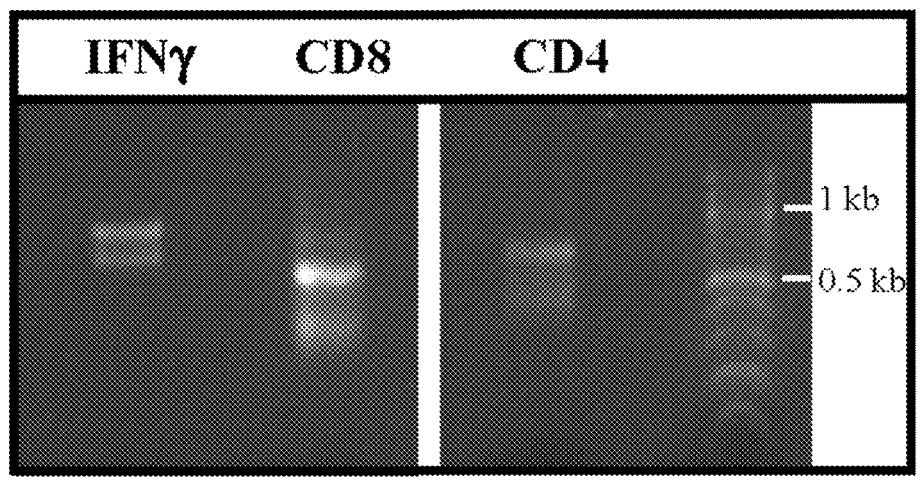

FIG. 28 shows library PCR amplification products of IFNγ, CD8 and CD4 genes. Products were visualized on a 2% agarose gel. A 100 bp ladder was loaded in the right lane.

Figure 29:
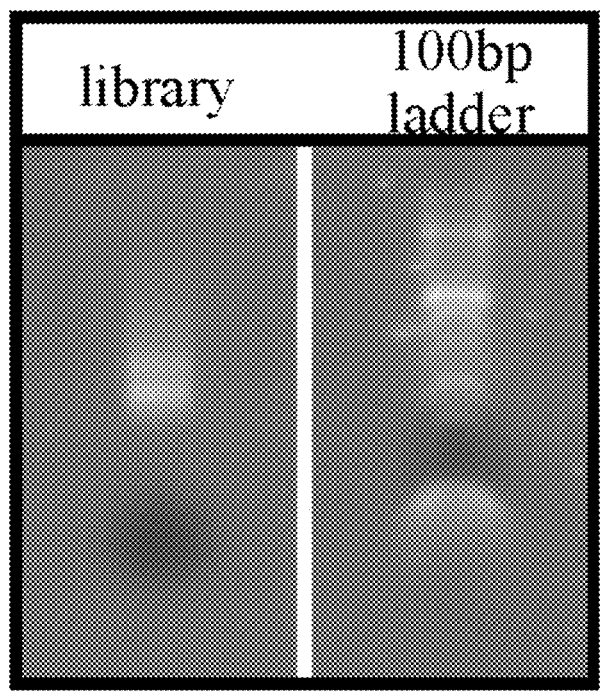

FIG. 29 shows library PCR amplification products of a transcriptomics library. Products were visualized on a 2% agarose gel. A 100 bp ladder was loaded in the right lane.

DEFINITIONS

As the term is used herein, "incorporating" a sequence into a polynucleotide refers to covalently linking a series of nucleotides with the rest of the polynucleotide, for example at the 3' or 5' end of the polynucleotide, by phosphodiester bonds, wherein the nucleotides are linked in the order prescribed by the sequence. A sequence has been "incorporated" into a polynucleotide, or equivalently the polynucleotide "incorporates" the sequence, if the polynucleotide contains the sequence or a complement thereof. Incorporation of a sequence into a polynucleotide can occur enzymatically (e.g., by ligation or polymerization) or using chemical synthesis (e.g., by phosphoramidite chemistry).

As used herein, the terms "amplify" and "amplification" refer to enzymatically copying the sequence of a polynucleotide, in whole or in part, so as to generate more polynucleotides that also contain the sequence or a complement thereof. The sequence being copied is referred to as the template sequence. Examples of amplification include DNA-templated RNA synthesis by RNA polymerase, RNA-templated first-strand cDNA synthesis by reverse transcriptase, and DNA-templated PCR amplification using a thermostable DNA polymerase. Amplification includes all primer-extension reactions.

As used herein, the term "isothermal" refers to a reaction, such as an enzymatic reaction, that is carried out at a constant temperature or range of temperatures.

The term "associated" is used herein to refer to the relationship between a sample and the DNA molecules, RNA molecules, or other polynucleotides originating from or derived from that sample. A polynucleotide is associated with a sample if it is an endogenous polynucleotide, i.e. it occurs in the sample at the time the sample is selected, or is derived from an endogenous polynucleotide. For example, the mRNAs endogenous to a cell are associated with that cell. cDNAs resulting from reverse transcription of these mRNAs, and DNA amplicons resulting from PCR amplification of the cDNAs, contain the sequences of the mRNAs and are also associated with the cell. The polynucleotides associated with a sample need not be located or synthesized in the sample, and are considered associated with the sample even after the sample has been destroyed (for example, after a cell has been lysed). Molecular barcoding or other techniques can be used to determine which polynucleotides in a mixture are associated with a particular sample.

As the term is used herein, a "reaction volume" (or equivalently a "container" or "compartment") is a space where a volume of liquid, for example an aqueous solution, can be held and remain segregated (e.g., isolated) from other such volumes of liquid or the surrounding medium. The segregation between a reaction volume and its surroundings can result from solid barriers around the reaction volume or from phase separation. For example, an aqueous microfluidic droplet suspended in a hydrophobic carrier fluid can constitute a reaction volume because water is immiscible in the carrier fluid. Thus, two droplets that are separated from each other in the carrier fluid remain segregated, and nucleic acids or other hydrophilic species dissolved in one droplet cannot exit the droplet or transit to another droplet. Reaction volumes can also be defined by, for example, flasks, beakers, centrifuge tubes, and wells in a multi-well plate.

"Adding" a barcode adapter to the RNAs associated with a sample involves introducing the adapter molecule into the reaction volume containing these RNAs, such that the RNAs can take part in a barcoding reaction. Once added, the barcode adapter can react directly with one or more RNAs, for example by hybridizing with an RNA, or can take part in a polymerization reaction or series of reactions (for example, reverse transcription or RT-PCR) in which RNA molecules serve as templates.

In some aspects, a composition can include a polynucleotide. The term "polynucleotide(s)" refers to nucleic acids such as DNA molecules and RNA molecules and analogs thereof (e.g., DNA or RNA generated using nucleotide analogs or using nucleic acid chemistry). As desired, the polynucleotides may be made synthetically, e.g., using art-recognized nucleic acid chemistry or enzymatically using, e.g., a polymerase, and, if desired, can be modified. Typical modifications include methylation, biotinylation, and other art-known modifications. In addition, a polynucleotide can be single-stranded or double-stranded and, where desired, linked to a detectable moiety. In some aspects, a polynucleotide can include hybrid molecules, e.g., comprising DNA and RNA.

"G," "C," "A," "T" and "U" each generally stand for a nucleotide that contains guanine, cytosine, adenine, thymidine and uracil as a base, respectively. However, it will be understood that the term "ribonucleotide" or "nucleotide"

can also refer to a modified nucleotide or a surrogate replacement moiety. The skilled person is well aware that guanine, cytosine, adenine, and uracil may be replaced by other moieties without substantially altering the base pairing properties of an oligonucleotide comprising a nucleotide bearing such replacement moiety. For example, without limitation, a nucleotide comprising inosine as its base may base pair with nucleotides containing adenine, cytosine, or uracil. Hence, nucleotides containing uracil, guanine, or adenine may be replaced in nucleotide sequences by a nucleotide containing, for example, inosine. In another example, adenine and cytosine anywhere in the oligonucleotide can be replaced with guanine and uracil, respectively to form G-U Wobble base pairing with the target mRNA. Sequences containing such replacement moieties are suitable for the compositions and methods described herein.

As used herein, and unless otherwise indicated, the term "complementary," when used to describe a first nucleotide sequence in relation to a second nucleotide sequence, refers to the ability of a polynucleotide comprising the first nucleotide sequence to hybridize and form a duplex structure under certain conditions with a polynucleotide comprising the second nucleotide sequence, as will be understood by the skilled person. Such conditions can, for example, be stringent conditions, where stringent conditions may include: 400 mM NaCl, 40 mM PIPES pH 6.4, 1 mM EDTA, 50° C. or 70° C. for 12-16 hours followed by washing. Other conditions, such as physiologically relevant conditions as may be encountered inside an organism, can apply. The skilled person will be able to determine the set of conditions most appropriate for a test of complementarity of two sequences in accordance with the ultimate application of the hybridized nucleotides.

Complementary sequences include base-pairing of a region of a polynucleotide comprising a first nucleotide sequence to a region of a polynucleotide comprising a second nucleotide sequence over the length or a portion of the length of one or both nucleotide sequences. Such sequences can be referred to as "complementary" with respect to each other herein. However, where a first sequence is referred to as "substantially complementary" with respect to a second sequence herein, the two sequences can be complementary, or they may include one or more, but generally not more than about 5, 4, 3, or 2 mismatched base pairs within regions that are base-paired. For two sequences with mismatched base pairs, the sequences will be considered "substantially complementary" as long as the two nucleotide sequences bind to each other via base-pairing.

"Complementary" sequences, as used herein, may also include, or be formed entirely from, non-Watson-Crick base pairs and/or base pairs formed from non-natural and modified nucleotides, in as far as the above embodiments with respect to their ability to hybridize are fulfilled. Such non-Watson-Crick base pairs includes, but are not limited to, G:U Wobble or Hoogstein base pairing.

The term percent "identity," in the context of two or more nucleic acid or polypeptide sequences, refer to two or more sequences or subsequences that have a specified percentage of nucleotides or amino acid residues that are the same, when compared and aligned for maximum correspondence, as measured using one of the sequence comparison algorithms described below (e.g., BLASTP and BLASTN or other algorithms available to persons of skill) or by visual inspection. Depending on the application, the percent "identity" can exist over a region of the sequence being compared, e.g., over a functional domain, or, alternatively, exist over the full length of the two sequences to be compared.

For sequence comparison, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., infra).

One example of an algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information web-site. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands.

Identical sequences include 100% identity of a polynucleotide comprising a first nucleotide sequence to a polynucleotide comprising a second nucleotide sequence over the entire length of one or both nucleotide sequences. Such sequences can be referred to as "fully identical" with respect to each other herein. However, in some aspects, where a first sequence is referred to as "substantially identical" with respect to a second sequence herein, the two sequences can be fully complementary, or they may have one or more, but generally not more than about 5, 4, 3, or 2 mismatched nucleotides upon alignment. In some aspects, where a first sequence is referred to as "substantially identical" with respect to a second sequence herein, the two sequences can be fully complementary, or they may be at least about 50, 60, 70, 80, 81, 82, 83, 84, 85, 86, 87, 88, 89, 90, 91, 92, 93, 94, 95, 96, 97, 98, or 99% identical to each other. To determine the percent identity of two nucleotide sequences described herein, the default settings of BLASTN described above can be used.

Where a first sequence is referred to as "distinct" with respect to the identity of a second sequence herein, the two sequences have at least one or more mismatched nucleotides upon alignment. In some aspects, distinct sequences can have 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or more mismatched nucleotides upon alignment. In some aspects, distinct sequences can be about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 81, 82, 83, 84, 85, 86, 87, 88, 89, 90, 91, 92, 93, 94, 95, 96, 97, 98, 99, or less than 100% identical to each other. In some aspects, where a first sequence is referred to as "distinct" with respect to a second sequence herein, the two sequences can have substantially or fully identical sequences, but instead differ from one another based upon differing patterns of modification within the sequences. Such modifications are generally known in the art, e.g., methylation.

In some aspects, a polynucleotide can be present in a library of polynucleotides. In some aspects, a polynucleotide library can include a plurality of polynucleotides. In some aspects, each polynucleotide in the plurality of polynucleotides can be derived from a single sample. In some aspects, a single sample can include a single cell such as a B cell.

Conventional notation is used herein to describe nucleotide sequences: the left-hand end of a single-stranded nucleotide sequence is the 5'-end; the left-hand direction of a double-stranded nucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand;" sequences on the DNA strand having the same sequence as an mRNA transcribed from that DNA and which are located 5' to the 5'-end of the RNA transcript are referred to as "upstream sequences;" sequences on the DNA strand having the same sequence as the RNA and which are 3' to the 3' end of the coding RNA transcript are referred to as "downstream sequences."

The term "messenger RNA" or "mRNA" refers to an RNA that is without introns and that can be translated into a polypeptide.

The term "cDNA" refers to a DNA that is complementary or identical to an mRNA, in either single stranded or double stranded form.

The term "amplicon" refers to the amplified product of a nucleic acid amplification reaction, e.g., RT-PCR.

The term "hybridize" refers to a sequence specific non-covalent binding interaction with a complementary nucleic acid. Hybridization may occur to all or a portion of a nucleic acid sequence. Those skilled in the art will recognize that the stability of a nucleic acid duplex, or hybrids, can be determined by the Tm. Additional guidance regarding hybridization conditions may be found in: Current Protocols in Molecular Biology, John Wiley & Sons, N.Y., 1989, 6.3.1-6.3.6 and in: Sambrook et al., Molecular Cloning, a Laboratory Manual, Cold Spring Harbor Laboratory Press, 1989, Vol. 3.

As used herein, "region" refers to a contiguous portion of the nucleotide sequence of a polynucleotide. Examples of regions are described herein an include identification regions, sample identification regions, plate identification regions, adapter regions, and the like. In some aspects, a polynucleotide can include one or more regions. In some aspects, a polynucleotide can include less than 2, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or more regions. In some aspects, regions can be coupled. In some aspects, regions can be operatively coupled. In some aspects, regions can be physically coupled.

As used herein "variable region" refers to a variable nucleotide sequence that arises from a gene recombination or gene conversion event, such as V(D)J recombination and homologous recombination between upstream VH gene segments and rearranged VDJ genes to produce a final, expressed gene product. Examples are but not limited to immunoglobulin genes and T cell receptor genes. For example, it can include a V, J, and/or D region of an immunoglobulin or T cell receptor sequence isolated from a T cell or B cell of interest, such as an activated T cell or an activated B cell.

As used herein "B cell variable immunoglobulin region" refers to a variable immunoglobulin nucleotide sequence isolated from a B cell. For example, a variable immunoglobulin sequence can include a V, J, and/or D region of an immunoglobulin sequence isolated from a B cell of interest such as a memory B cell, an activated B cell, or plasmablast.

As used herein, "barcode" or "barcode sequence" refers to any unique sequence label that can be coupled to at least one nucleotide sequence for, e.g., later identification of the at least one nucleotide sequence.

As used herein, "barcode set" refers to any unique set of sequences that can be coupled to nucleotide sequences from a sample, where a nucleotide sequence is coupled to one barcode sequence in the set, for, e.g., later identification of the nucleotide sequences.

The terms "barcode adapter", "barcoded adapter", and "barcode adapter molecule" are used interchangeably herein to refer to an oligonucleotide that comprises a unique barcode sequence.

The terms "barcode adapter template", "adapter template", "template molecule", "barcode adapter construct", and "adapter construct" are used interchangeably herein to refer to a nucleic acid molecule comprising a barcode sequence that can be used as a template to amplify and produce single stranded barcode adapter molecules.

As used herein, "barcode adapter template bead" refers to a bead coupled to one or more barcode adapter templates.

As used herein, "barcoding" or "barcoding reaction" refers to a reaction that links a barcode sequence, or the complement of a barcode sequence, with a nucleic acid. The barcode adapter need not necessarily be covalently linked with the nucleic acid, but the barcode sequence information itself is linked with or incorporated into the nucleic acid. "Barcoding nucleic acids", "barcoding cells", "barcoding nucleic acids from cells", "barcoding nucleic acids from reaction containers", and "barcoding reaction containers" are used interchangeably.

As used herein "identification region" refers to a nucleotide sequence label (e.g., a unique barcode sequence) that can be coupled to at least one nucleotide sequence for, e.g., later identification of the at least one nucleotide sequence. In some aspects, a barcode sequence is used as a sample identification region. In some aspects, a barcode set is used as a sample identification region.

As used herein "immunoglobulin region" refers to a contiguous portion of nucleotide sequence from one or both chains (heavy and light) of an antibody.

As used herein "adapter region" or "adapter molecule" refers to a linker that couples a first nucleotide sequence to a second nucleotide sequence. In some aspects, an adapter region can include a contiguous portion of nucleotide sequence that acts as a linker. In some aspects, an adapter region or adapter molecule can include a binding site, such as a cDNA binding site. For example, a binding site can have the sequence GGG and couples a first sequence to a second sequence via binding between GGG and CCC. In some aspects, the adapter region or adapter molecule can comprise elements such as an RNA polymerase promoter, a nicking endonuclease restriction site, a universal priming sequence, a barcode, and a cDNA binding site.

The term "sample" can include RNA, DNA, a single cell or multiple cells or fragments of cells or an aliquot of body fluid, taken from a subject (e.g., a mammalian subject, an animal subject, a human subject, or a non-human animal subject). Samples can be selected by one of skill in the art using any means now known or later discovered including centrifugation, venipuncture, blood draw, excretion, swabbing, ejaculation, massage, biopsy, needle aspirate, lavage sample, scraping, surgical incision, laser capture microdissection, gradient separation, or intervention or other means known in the art. Samples can also be selected by one of skill in the art using one or more markers known to be associated with a sample of interest. Samples can also be selected using methods known in the art such as cell sorting and FACS.

DETAILED DESCRIPTION OF THE INVENTION

Embodiments of the invention provide a method to generate unique nucleic acid barcoded adapters in each reaction container such that the nucleic acid barcoded adapters are in aqueous phase but the template from which they were generated can either be attached to a solid surface (such as attached to beads) or be free in solution. Nucleic acid barcoded adapters are any polynucleotide sequence that comprise a unique barcode sequence and may or may not have modifications (for example, biotinylated or contain C18 spacers) or contain modified polynucleotides (such as 2'-O-methyl RNA bases).

Also provided are compositions generated using the methods disclosed herein. Accordingly, the present invention provides compositions of RNA and DNA adapters and constructs for their generation. Also provided are barcode adapter template bead libraries, emulsion droplet libraries loaded with RNA barcode adapters, emulsions containing barcode libraries with cells, barcoded cDNA libraries, and microfluidic droplet generating devices, among others.

Figure 1:
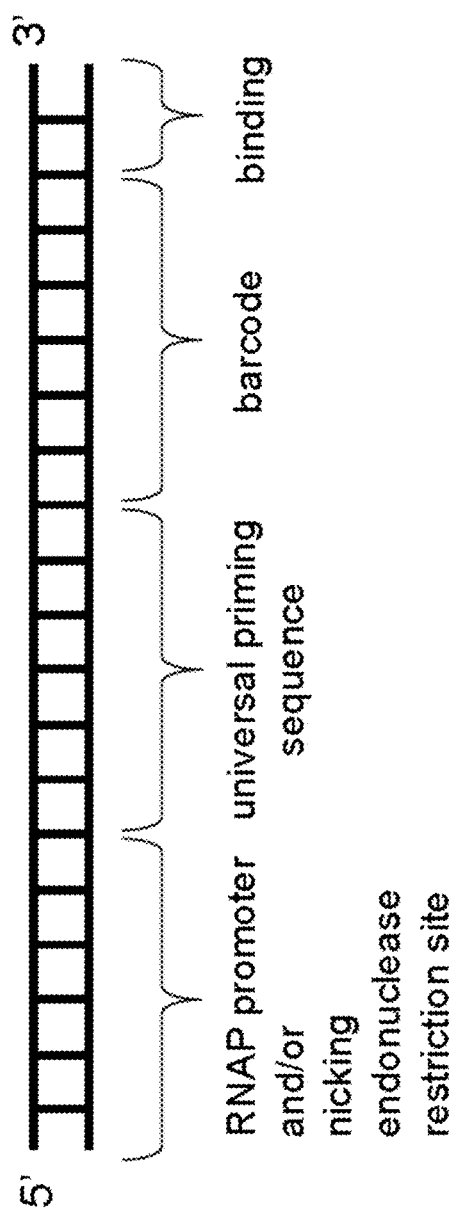
FIG. 1 is a map of an adapter molecule, or a template molecule for generating an adapter molecule, according to some embodiments of the invention. The sequence of an adapter molecule can include an RNA polymerase promoter and/or a nicking endonuclease site, followed by a universal priming sequence (used in subsequent PCR steps for annealing primers) followed by a barcode sequence and a nucleic acid binding sequence.

In some embodiments, the barcoded adapter template is a double-stranded DNA (dsDNA) template which comprises the following sequence: 5'-T7 promoter—universal priming sequence—barcode sequence—binding sequence-3'. The T7 promoter sequence allows for synthesis of an RNA barcoded adapter from the template by T7 RNA polymerase. The universal priming sequence is used for complementarity to PCR primers that are used downstream. The binding sequence consists of 1 or more guanine bases (G's) and allows for complementary base-pairing of the barcoded adapter to the 3' end of $1^{st}$ strand cDNA (FIG. 1).

Other promoter sequences can be used, such as but not limited to T3 and SP6 promoter sequences, which allows for synthesis of an RNA barcoded adapter by T3 and SP6 RNA polymerases respectively. Other RNA polymerases which do not have a specific promoter sequence may also be used, as long as a full length or near full length barcoded adapter is synthesized in a large fraction of cases (FIG. 2A). Isothermal amplification may also be used, typically using DNA polymerases with strand-displacement activity such as Bst large fragment and Klenow 3'→5'exo- as long as full length or near full length barcoded adapters are synthesized in a large fraction of cases. Specific primer or nicking endonuclease sequences may be used instead of a promoter sequence, depending on the isothermal amplification method used (FIG. 2B). Barcoded adapters thus generated will comprise DNA nucleotides instead of RNA nucleotides. Both RNA or DNA barcoded adapters can be attached to polynucleotides of interest.

Attaching barcoded adapters to 3' end of $1^{st}$ strand cDNA has been previously described (PCT/US2012/000221). Briefly, H-MMLV reverse transcriptases have a 3' dC tailing activity and add non-templated dCs to $1^{st}$ strand cDNA. If a barcoded adapter ending in at least 1 G is also present, the adapter can base-pair with the 3' dC of the $1^{st}$ strand cDNA and the reverse transcriptase undergoes template switching and continues transcription using the barcoded adapter as a template. The reverse transcriptase thus covalently adds the barcode sequence to the 3' end of the $1^{st}$ strand cDNA via phosphodiester bonds (FIG. 3).

In some embodiments, barcoded adapters are linearly amplified from double-stranded DNA (dsDNA) containing a 5' T7 promoter using a T7 RNA polymerase. In some embodiments, the barcoded adapters are linearly amplified in the same reaction as the reverse transcription reaction. Amplifying barcoded adapters from a dsDNA template provides at least the following advantages:
1. Barcoded adapter templates can be attached to beads (a unique barcode per bead) and stored in the same storage container
2. Multiple copies of a unique barcoded adapter can be delivered into a reaction container without use of an individual pipetting step
3. Barcoded adapters are amplified, overcoming the limited amount of polynucleotides that can be attached to each bead
4. Amplified barcodes are in aqueous phase and utilize much more rapid liquid phase rather than solid phase kinetics There are also advantages involved in using an RNA barcoded adapter rather than a DNA barcoded adapter:
1. An RNA barcoded adapter may be more efficient in the template switching reaction which attaches the barcode sequence to polynucleotides of interest as reverse transcriptases typically use RNA rather than DNA as a template and template switching is used by the reverse transcriptase in vivo to switch to an RNA template in the replication of retroviruses.
2. Using an entirely RNA transcript as an adapter results in less background when using proof-reading DNA polymerases in downstream PCR reactions. Background occurs when the barcode adapter misprimes and initiates reverse transcription, resulting in barcode adapter sequences added at both the 5' and 3' end of $1^{st}$ strand cDNA. These can be amplified in PCR by just one primer complementary to the barcode adapter. However, if proof-reading DNA polymerases are used during PCR, they will not transcribe the RNA primer (FIG. 4), eliminating background from barcode adapter mispriming.

Due to the large number of barcoding reactions involved, NextGen sequencing is best suited to sequencing the barcoded nucleic acids to bioinformatically associate nucleic acids from the same reaction container with one another. Additional barcodes may be associated with a set of samples that are distinct from another set of samples and can be associated using PCR primers with unique barcode sequences. These additional barcodes are also refered to as plate-IDs. Plate-IDs confer advantages such as distinguishing between different sets of samples in the same sequencing run, or bioinformatically tracking and eliminating any potential contaminations between different sets of samples.

As PCR and NextGen sequencing errors are unavoidable, the barcodes described herein can be designed to be a reasonable distance (e.g., Hamming or edit distance) apart in sequence space, so that the sequences of any two barcodes will differ from each other by at least several nucleotides. Thus, the majority of barcode sequencing reads can be correctly assigned, with a small percentage of unassigned and misassigned barcodes.

In some embodiments, pre-determined barcode sequences are designed with a minimum Hamming or edit distance apart. In some embodiments, barcodes comprise random nucleotides, such as $(N)_{15}$, which results in a total possible space of $4^{15}$, or ~1 billion unique barcode sequences. If the number of samples to be barcoded is much fewer than this total space, e.g. 1 million, or 0.1% of the total barcode space, we expect the barcodes should be of sufficient distance apart from one another that the majority of barcodes should be correctly assigned.

As long as the misassignment rate is sufficiently low, misassigned sequencing reads can be detected and discarded simply because the nucleic acids linked to the misassigned barcode sequence are different from the consensus sequence. We would expect the consensus sequence for each gene (e.g. gamma heavy chain, TCR alpha chain) associated to a barcode sequence to be assembled from correctly assigned reads as the barcode sequences were designed to be of a sufficient distance apart.

Samples in reaction containers can be barcoded with either a unique barcode, or a unique barcode set. A unique barcode set can be used by, e.g., delivering two or more barcode adapter template beads per reaction container, and each nucleic acid of a sample is barcoded with one of the barcodes in the unique barcode set. Nucleic acids are then associated to a sample by use of a unique barcode set.

One method to distinguish which barcode sets are used for which samples is by examining reads from NextGen sequencing. Each barcode sequence is expected to be associated with assembled contigs from different samples as barcode sequences are reused in unique barcode sets. But contigs from the same sample are expected to be identical. For example, identical immunoglobulin gamma heavy chain contigs may be observed to be using barcode sequences a, b and c. And barcode sequences a, b and d may be observed to be associated with another immunoglobulin gamma heavy chain contig. From this, we can then conclude that a, b and c comprise barcode set1, and a, b and d barcode set2.

In some embodiments, a library of barcode adapter template beads of N unique barcode sequences is sufficiently diverse to barcode n samples that such the majority of samples are barcoded with either a unique barcode or a unique barcode set. If the number of barcode adapter template beads greatly exceed N, sampling with replacement can be approximated, and the number of samples barcoded with a unique barcode, U follows the binomial distribution and is given by:

$$U = N * \binom{n}{k} p^k (1-p)^{n-k}$$

Where k=1, and p=1/N.

The fraction of samples that are not barcoded with a unique barcode (and thus have two or more samples associated with one another) is given by $$1 - U/n$$

The relationship between N, n and the fraction of samples not barcoded with a unique barcode is given in Table 1.

TABLE 1

Fraction of samples not barcoded with a unique barcode

| # unique barcodes (N) | # samples barcoded (n) | | | | |
|---|---|---|---|---|---|
| | 1,000 | 10,000 | 100,000 | 1,000,000 | 10,000,000 |
| 1,000 | 63.19% | 100.00% | 100.00% | 100.00% | 100.00% |
| 5,000 | 18.11% | 86.47% | 100.00% | 100.00% | 100.00% |

TABLE 1-continued

Fraction of samples not barcoded with a unique barcode

| # unique barcodes (N) | # samples barcoded (n) | | | | |
|---|---|---|---|---|---|
| | 1,000 | 10,000 | 100,000 | 1,000,000 | 10,000,000 |
| 10,000 | 9.51% | 63.21% | 100.00% | 100.00% | 100.00% |
| 50,000 | 1.98% | 18.13% | 86.47% | 100.00% | 100.00% |
| 100,000 | 0.99% | 9.52% | 63.21% | 100.00% | 100.00% |
| 500,000 | 0.20% | 1.98% | 18.13% | 86.47% | 100.00% |
| 1,000,000 | 0.10% | 0.99% | 9.52% | 63.21% | 100.00% |
| 5,000,000 | 0.02% | 0.20% | 1.98% | 18.13% | 86.47% |
| 10,000,000 | 0.01% | 0.10% | 1.00% | 9.52% | 63.21% |
| 50,000,000 | 0.00% | 0.02% | 0.20% | 1.98% | 18.13% |
| 100,000,000 | 0.00% | 0.01% | 0.10% | 1.00% | 9.52% |

As can be seen, if N=10n, >90% of the samples will be barcoded with a unique barcode.

The number of samples barcoded with a unique barcode set, $U_{SET}$, with x barcodes in a set also follows the binomial distribution, and can be thought of as a barcode library with $\binom{N}{x}$ unique barcode combinations (N is assumed to be sufficiently large that combination is essentially without repetition), with nx barcodes used to barcode n samples and is given by:

$$U_{SET} = \binom{N}{x} * \binom{n}{k} p^k (1-p)^{n-k}$$

Where k=1, and $$p = 1 \bigg/ \binom{N}{x}.$$

The fraction of samples that are not barcoded with a unique barcode (and thus have two or more samples associated with one another) is given by $$1 - U_{SET}/n$$

The relationship between N, n, x and the fraction of samples not barcoded with a unique barcode is given in Tables 2 and 3.

TABLE 2

Fraction of samples not barcoded with a unique barcode set when x = 2

| # unique barcodes (N) when using barcode set with x = 2 | # samples barcoded (n) | | | | |
|---|---|---|---|---|---|
| | 1,000 | 10,000 | 100,000 | 1,000,000 | 10,000,000 |
| 100 | 18.28% | 86.74% | 100.00% | 100.00% | 100.00% |
| 500 | 0.80% | 7.70% | 55.14% | 99.97% | 100.00% |
| 1,000 | 0.20% | 1.98% | 18.14% | 86.49% | 100.00% |
| 5,000 | 0.01% | 0.08% | 0.80% | 7.69% | 55.07% |
| 10,000 | 0.00% | 0.02% | 0.20% | 1.98% | 18.13% |
| 50,000 | 0.00% | 0.00% | 0.01% | 0.08% | 0.80% |
| 100,000 | 0.00% | 0.00% | 0.00% | 0.02% | 0.20% |

TABLE 3

Fraction of samples not barcoded with a unique barcode set when x = 3

| # unique barcodes (N) when using barcode set with | # samples barcoded (n) | | | | |
|---|---|---|---|---|---|
| x = 3 | 1,000 | 10,000 | 100,000 | 1,000,000 | 10,000,000 |
| 100 | 0.62% | 6.00% | 46.12% | 99.79% | 100.00% |
| 500 | 0.00% | 0.05% | 0.48% | 4.71% | 38.30% |
| 1,000 | 0.00% | 0.01% | 0.06% | 0.60% | 5.84% |
| 5,000 | 0.00% | 0.00% | 0.00% | 0.00% | 0.05% |
| 10,000 | 0.00% | 0.00% | 0.00% | 0.00% | 0.01% |
| 50,000 | 0.00% | 0.00% | 0.00% | 0.00% | 0.00% |
| 100,000 | 0.00% | 0.00% | 0.00% | 0.00% | 0.00% |

As can be seen, when using unique barcode sets instead of unique barcodes, a much smaller number of unique barcodes in the barcode adapter library is required to barcode a similar number of samples such that the majority of samples can be identified with a unique barcode set.

I. METHODS

A. Producing Polynucleotides of Interest

In some aspects, the present invention provides methods for producing one or more polynucleotides of interest. Such polynucleotides can be barcoded nucleic acids, for example cDNAs or DNA amplicons containing barcodes, wherein a common barcode or barcode set indicates that a group of polynucleotides are derived from the same sample. According to the methods, a plurality of RNAs associated with one or more samples is obtained as described below. The RNAs associated with each sample are present in a separate reaction volume. An adapter molecule is then added to the RNAs associated with each sample to incorporate a barcode sequence into one or more polynucleotides derived from the RNAs.

To maximize barcoding reaction kinetics, the barcode adapter is preferably free in solution prior to or at the time it is added to the RNAs. Adding the barcode adapter can be achieved by pipetting, by pouring one reaction volume into another, or by merging two or more reaction volumes. For example, the barcode adapter can be generated and/or encapsulated in one reaction volume, which can then be combined with another reaction volume containing RNAs associated with one sample (FIG. 5A-C). In some embodiments, the barcode adapter added to the RNAs from a sample is generated in situ in the reaction volume where the RNAs are present.

In some embodiments, barcode adapters are generated enzymatically from barcode adapter templates. A barcode adapter template can be a double-stranded DNA molecule containing a barcode sequence, as well as other sequence regions to facilitate generation of the barcode adapter and the subsequent barcoding of nucleic acids (FIG. 1). Barcode adapter templates can be prepared using standard molecular cloning techniques. In some embodiments, a barcode adapter template includes a promoter for RNA polymerase (RNAP), such as a T7, T3, or SP6 promoter. An RNA barcode adapter can then be generated by contacting the template molecule with an appropriate RNAP and allowing in vitro transcription to occur (FIG. 2A). In some embodiments, a barcode adapter template includes a nicking endonuclease restriction site, such as a Nt.BbvCI, Nt.BspQI, Nt.BsmAI, Nt.BstNBI, Nt.AlwI, or Nt.BsmAI site. DNA barcode adapters can be generated from such a template by contacting the template with a nicking endonuclease specific for the restriction site, and then exposing the template to a strand-displacing DNA polymerase (FIG. 2B). Examples of suitable strand-displacing DNA polymerases include Klenow exo-fragment, Bst Large Fragment, and engineered variants thereof. In general, barcode adapters are generated from barcode adapter templates by contacting the templates with one or more enzymes. In some embodiments, the enzymatic reactions are isothermal reactions.

A barcode adapter template can be free in solution when it is used to generate barcode adapters, or it can be bound to a solid support. Examples of solid supports that can be used in embodiments of the present methods and compositions include beads, chromatographic resins, multi-well plates, microcentrifuge tubes, or other objects having solid surfaces. A barcode adapter template can be bound to a solid support using any desired mechanism or capture chemistry, for example a biotin-avidin, biotin-streptavidin, or gold-thiol interaction. In some embodiments, any solid support to which a barcode adapter template is attached is contacted with an aqueous solution, and barcode adapter molecules generated from the template are released into this solution as they are generated (FIGS. 6A, 6B, 7A-D). The aqueous solution can be in the same reaction volume as the RNA molecules associated with the sample to which the barcode adapter molecule is to be added. That is, the barcode adapter molecule can be generated in situ for the barcoding reaction. Alternatively, the aqueous solution contacting the solid support for a barcode adapter template can be held in a different reaction volume from the target RNAs, and barcode adapters generated from the template can be added to these RNAs upon combining the two reaction volumes.

In some embodiments, barcode adapters are generated by cleaving barcode adapter templates from a solid support (FIGS. 7B and 7D). Template molecules can contain endonuclease restriction sites that facilitate cleavage of the template molecules upon exposure to an appropriate enzyme (e.g., a restriction endonuclease). The nucleic acid molecule that is released into solution upon such cleavage can serve as a barcode adapter and take part directly in a barcoding reaction, or can be subjected to further enzymatic reactions (e.g., in vitro transcription) to generate adapter molecules.

Regardless of how barcode adapter molecules are generated, libraries of these molecules can be prepared to barcode nucleic acids from many samples. Adapter molecules can be segregated into different reaction volumes, such that each reaction volume contains, for example, one adapter molecule on average. Alternatively, each reaction volume can contain multiple copies of an adapter molecule, wherein each copy contains the same barcode sequence. The reaction volumes can be microfluidic droplets or can be enclosed in microcentrifuge tubes or other containers.

A barcode adapter molecule can include, in addition to a barcode sequence, a universal priming sequence or universal priming region, and a binding site, as described below under "Compositions". The adapter molecule can also include a unique molecular identifier (UMI) sequence. In some embodiments, a UMI sequence contains randomized nucleotides and is incorporated into the barcode adapter (or the barcode adapter template from which the adapter is generated) independently of the barcode sequence. Thus, a set of barcode adapter molecules containing the same barcode sequence can contain different UMI sequences. In embodiments where the set of barcode adapter molecules containing the same barcode sequence but different UMI sequences is added to the RNAs associated with one sample, every RNA sequence can be linked to a different UMI sequence during barcoding. Methods of preparing barcode adapter template beads with UMI sequences, wherein the template molecules on each bead contain the same barcode sequence and a library of different UMI sequences, are disclosed below in Examples 12 and 13.

Barcode adapters can be RNA or DNA molecules, or RNA-DNA hybrids. For example, an adapter can include RNA nucleotides covalently linked to DNA nucleotides in a common oligonucleotide strand. A barcode adapter can also be single-stranded or double stranded. If double-stranded, the barcode adapter can have one or more blunt ends or ends with single-stranded overhangs.

In some embodiments, the barcode adapter is a single-stranded DNA molecule and serves as a primer for reverse transcription. The barcode adapter can be generated using a DNA polymerase (DNAP). Here, the binding site of the barcode adapter is an RNA binding site (e.g., an mRNA binding site) and contains a sequence region complementary to a sequence region in one or more RNAs. In some embodiments, the binding site is complementary to a sequence region common to all RNAs in the sample to which the barcode adapter is added. For example, the binding site can be a poly-T tract, which is complementary to the poly-A tails of eukaryotic mRNAs (FIG. 8). Alternatively or in addition, the binding site can include a random sequence tract (FIG. 9). Upon adding the barcode adapter to the RNAs associated with a sample, reverse transcription can occur and first strands of cDNA can be synthesized, such that the barcode sequence is incorporated into the first strands of cDNA. It will be recognized that reverse transcription requires appropriate conditions, for example the presence of an appropriate buffer and reverse transcriptase enzyme, and temperatures appropriate for annealing of the barcode adapter to RNAs and the activity of the enzyme. It will also be recognized that reverse transcription, involving a DNA primer and an RNA template, is most efficient when the 3' end of the primer is complementary to the template and can anneal directly to the template. Accordingly, the barcode adapter can be designed so that the binding site occurs at the 3' end of the adapter molecule.

When the barcode adapter is used as a primer for first strand cDNA synthesis in reverse transcription, and in other embodiments of the present methods involving reverse transcription (described below), the reverse transcription reaction can occur in the same reaction volume where the barcode adapter is generated. Thus, the barcode adapter can be added to a sample, or the RNAs associated with the sample, at the time the barcode adapter is generated. For example, a microfluidic droplet can contain a bead to which barcode adapter templates are bound, and a cell (FIG. 10). Barcode adapter molecules can be generated if one or more enzymes, such as a nicking endonuclease, strand-displacing DNA polymerase, or RNA polymerase, are also present in the droplet. Reverse transcription can then occur if lysis reagents are present in the droplet to release RNAs from the cell, and if reverse transcriptase, primers, and other appropriate reagents are present. Enzymes and reagents for generating barcode adapters and facilitating lysis and reverse transcription can be added to the droplet all at once, for example by merging a droplet containing the enzymes and reagents with the droplet containing the bead and cell, or can be added in steps.

In some embodiments of the present methods, the RNAs associated with each sample are reverse-transcribed but the barcode adapter does not prime first strand cDNA synthesis. Instead, a standard DNA primer containing a poly-T tract, random sequence, or other RNA binding site is used. In these embodiments, the barcode adapter can be generated in the same compartment or reaction volume where first-strand cDNA synthesis occurs. In this case, it can be beneficial to include a buffer in the reaction volume with Tris, potassium ions, chloride ions, sulphate ions, ammonium ions, acetic acid ions, and/or magnesium ions at a pH of about 8.0 to 8.8. Alternatively, the barcode adapter can be generated and first strand cDNA synthesis can occur in different compartments, in which case the compartments can be combined before or after first strand cDNA synthesis, as desired. The compartments can also be combined before or after the barcode adapter is generated. The different possibilities for carrying out enzymatic reactions and combining compartments provide flexibility for optimizing reaction conditions. Regardless of how the barcode adapter is added to the RNAs associated with a sample, however, the barcode adapter can take part in enzymatic barcoding reactions during or immediately after first strand cDNA synthesis.

As described above, the present methods can employ a reverse transcriptase enzyme (for example MMLV H⁻ reverse transcriptase) that adds one or more non-templated nucleotides (such as Cs) to the end of a nascent cDNA strand upon reaching the 5' end of the template RNA. These nucleotides form a 3' DNA overhang at one end of the RNA/DNA duplex. If a second RNA molecule contains a sequence region, for example a poly-G tract at its 3' end, that is complementary to the non-templated nucleotides, and binds to the non-templated nucleotides, the reverse transcriptase can switch templates and continue extending the cDNA, now using the second RNA molecule as a template. Such a second RNA molecule is referred to herein and known in the art as a template-switching oligonucleotide.

In embodiments of the present methods, the barcode adapter serves as a template-switching oligonucleotide for reverse transcription (FIG. 3). Thus, the barcode sequence is incorporated into the first strand of cDNA after template switching, and is present in DNA molecules resulting from amplification (for example, by PCR) of the first strand of cDNA. In these embodiments, any reverse transcriptase that has template switching activity can be used. The binding site of the barcode adapter is a cDNA binding site and preferably occurs at the 3' end of the adapter molecule. The binding site can include a G-tract (comprising one or more G nucleotides), or any other sequence that is at least partially complementary to that of the 3' overhang generated by the reverse transcriptase. It will be recognized that the overhang sequence, and thus an appropriate sequence for the binding site of the barcode adapter, may depend on the choice of reverse transcriptase used in the method.

In other embodiments, the RNAs associated with each sample are reverse-transcribed, but a barcode sequence is not incorporated into the first strand of cDNA at all. That is, the barcode adapter does not serve as a primer for first strand cDNA synthesis or as a strand-switching oligonucleotide. Rather, the barcode adapter serves as a primer for PCR amplification of the first strand of cDNA or its complement. In these embodiments, the cDNA is amplified using a forward primer and a reverse primer, where the reverse primer has the same sequence as at least a portion of the primer for first-strand cDNA synthesis. The barcode adapter can be either the forward primer or the reverse primer, and is a single-stranded DNA oligonucleotide. When the barcode adapter is the forward primer, it can anneal to a part of the first-strand cDNA (or its complement) resulting from extension of the cDNA following strand-switching (FIG. 11). Alternatively, the barcode adapter can anneal to a part of the first-strand cDNA templated on an RNA from the sample. Thus, template switching, and the addition of a template-switching oligonucleotide to the reaction volume for the sample, need not occur to carry out these embodiments of the invention. When the barcode adapter is the reverse primer, it can be used in conjunction with any primer for first-strand cDNA synthesis, including a primer that includes a random sequence (FIGS. 12 and 13).

The methods of the present invention can be practiced with any desired samples. In some embodiments, each sample includes a cell, and can be for example a single cell. A cell can be enclosed in a reaction volume such as a microfluidic droplet, and if desired can be lysed to release RNA molecules into the reaction volume. For this purpose, the cell can be contacted with a lysis buffer at any convenient time. The cell can be a B cell, for example, a plasmablast, memory B cell, or plasma cell, or any other kind of cell.

The inventors have found that cells can be advantageously suspended in a cell suspension buffer comprising an osmoprotectant prior to lysis. The osmoprotectant can protect the cells from osmotic stress and ensure that cellular physiology remains stable or unperturbed prior to barcoding. In some embodiments, cells are suspended in the cell suspension buffer along with barcode adapter molecules and/or barcode adapter templates. In some embodiments, cells are suspended in the cell suspension buffer before being contacted with reagents for reverse transcription, PCR, and/or lysis. The cell suspension buffer can be included in any reaction volume and is compatible with the methods described herein for forming and combining aqueous reaction volumes.

In some embodiments, the osmoprotectant in the cell suspension buffer is a betaine or a close structural analog thereof. Examples of betaines and close structural analogs include glycine betaine (also called N,N,N-trimethylglycine), proline betaine (also called stachydrine), beta-alanine betaine, ectoine, choline-O-sulfate, trigonelline, dimethylsulfoniopropionate (DMSP), and dimethylthetin. In some embodiments, the osmoprotectant is glycine betaine. In addition to serving as osmoprotectants, betaines have been shown to reduce the formation of secondary structure in PCR and improve the specificity of amplification. Betaines can therefore can be generally beneficial to include in the present methods.

In some embodiments, the osmoprotectant is a sugar or polyol, such as trehalose. Other useful sugars or polyols include sucrose, fructose, raffinose, mannitol, and myo-inositol. In some embodiments, the osmoprotectant is an amino acid such as proline. A single osmoprotectant can be included in the cell suspension buffer, or multiple osmoprotectants can be included in combination. Each osmoprotectant can be present at any useful concentration. In some embodiments, the osmolarity of the cell suspension buffer is about 250-350 mOsm/L. In some embodiments, the osmoprotectant contributes up to 10%, 20%, 30%, 40%, 50%, 60%, 70%, 80%, 90%, or 100% of the osmolarity of the buffer. An exemplary cell suspension buffer used herein (see, e.g., Examples 7-9, 11, and 14) includes about 230-330 mM betaine and about 10 mM NaCl.

In embodiments where each sample includes at least one cell, the RNAs associated with the sample can include mRNAs. The sample can include, for example, at least 1, 3, 10, 30, 100, 300, 1,000, 3,000, 10,000, 30,000, 100,000, 300,000, or 1,000,000 mRNA molecules, which can represent any number of genes, alleles, reading frames, or distinct sequences. In some embodiments, the RNAs associated with the sample include all mRNAs from the sample, a full or partial transcriptome of the cell, or the total RNA from the cell.

It will be recognized that more RNAs per sample can be barcoded and more polynucleotides of interest can be produced if larger numbers of barcode adapter molecules can be delivered to the reaction volume for each sample. However, without being bound by any theory, the present methods place no limits on the number of RNAs that can be barcoded per sample, Accordingly, the number of polynucleotides of interest produced per sample can be at least 10, 30, 100, 300, 1,000, 3,000, 10,000, 30,000, 100,000, 300,000, or 1,000, 000. Each polynucleotide of interest can be present in multiple copies. Furthermore, the number of cells or samples that can be barcoded in one execution of the method is limited only by the challenges (discussed above) of preparing many barcode adapter templates with unique barcode sequences. In some embodiments, the one or more samples include at least 10, 30, 100, 300, 1,000, 3,000, 10,000, 30,000, 100,000, 300,000, or 1,000,000 cells. Samples (for example, each being a single cell) can be obtained from the same subject or different subjects. For example, at least 2, 3, 4, 5, 6, 7, 8, 9, 10, 20, 30, 40, 50, 60, 70, 80, 90 or 100 different subjects can provide samples.

The present methods can also be used to interrogate a population of cells for a phenotype of interest using a nucleic acid marker. The nucleic acid marker includes a nucleic acid linked to a binder, which can specifically bind to a subset of cells from the population that do or do not present the phenotype. For example, the binder can bind to certain proteins, glycoproteins, glycolipids, or other moieties present on the surfaces of some cells. In some embodiments, the binder is a molecular label such as an antibody, antigen, or protein (FIGS. 14A-C). In some embodiments, the binder is a peptide-MHC complex. The nucleic acid can be linked to the binder covalently, using a non-covalent capture moiety, or otherwise as desired.

To interrogate cells for the phenotype, cells are contacted with the nucleic acid marker and then washed. Thus, the nucleic acid marker is retained only on the cells to which the binder binds. The cells can then be enclosed in reaction volumes and lysed as described above, so that RNAs in the cells can be barcoded. During the barcoding reaction, the nucleic acid of the nucleic acid marker is also barcoded, so that the marker sequence appears in RNA or amplicon sequencing data for a cell that retains the marker. In some embodiments, the nucleic acid of the nucleic acid marker is an RNA molecule with a sequence not endogenous to cells of the population. In some embodiments, the nucleic acid is a double-stranded DNA molecule comprising an RNAP promoter. Thus, the nucleic acid can be transcribed while in the same reaction volume as the cell (or a lysate thereof), and the resulting RNA molecules can be barcoded along with RNAs from the cell.

Cells can be interrogated for multiple phenotypes using multiple nucleic acid markers, each including a different binder linked to a different nucleic acid sequence. For example, cells can be contacted with a first nucleic acid marker and a second nucleic acid marker, wherein each nucleic acid marker includes a molecular label linked to a nucleic acid. The molecular labels of the two nucleic acid markers can be different from each other (for example, be different proteins or have affinities for different cell surface moieties). The nucleic acids linked to these molecular labels can contain sequences that differ from each other in whole or in part. Cells can be contacted with two or more nucleic acid markers simultaneously or sequentially.

As a further example, three antibodies can be linked to different non-endogenous RNA sequences, and barcoded sequencing data for cells treated with these antibodies can reveal whether each cell presents targets for none, some, or all of the antibodies. The copy number of barcoded amplicons may also reveal phenotypes by degree, for example the relative abundances of a cell surface moiety on different cells, where the moiety is targeted by the nucleic acid marker.

B. Attaching Polynucleotides to Solid Supports

Another aspect of the present invention provides methods for attaching a polynucleotide to a solid support, wherein the polynucleotide contains a barcode sequence. The polynucleotide can be a barcode adapter template or a precursor to such a template. The polynucleotide can thus be used as described above to enzymatically generate barcode adapters and incorporate the barcode sequences into amplicons derived from RNAs.

In some embodiments, the methods involve generating a hydrophilic compartment (i.e., an aqueous droplet) of an inverse emulsion. The compartment can be generated as desired, for example by mixing an aqueous solution in a hydrophobic carrier fluid and optionally agitating the mixture. The aqueous solution can have a solid support, oligonucleotides, and reagents suspended therein, so that each compartment contains all necessary components for attaching the polynucleotide to the solid support when the compartment is formed. In these embodiments, prior to adding the solid support to the compartment, an oligonucleotide is bound to the surface of the solid support via a capture moiety. This oligonucleotide is referred to herein as the "bound oligonucleotide" and contains a 3' sequence complementary to a 3' sequence of a barcode oligonucleotide. The polynucleotide is thus formed on the solid support through a polymerase extension reaction involving the bound oligonucleotide and barcode oligonucleotide, and this reaction takes place within the compartment.

In preferred embodiments, when the hydrophilic compartment is formed, the barcode oligonucleotide is present at a low or limiting concentration (for example, one molecule per compartment). This concentration is convenient when a library of barcode oligonucleotides having randomized sequences is used to prepare a plurality of barcode template beads. If every barcode oligonucleotide is assumed to have a different barcode sequence, and the solid support in each compartment is desired to have only one barcode sequence, then one barcode oligonucleotide (at most or on average) can be present per compartment. Once this condition is met, multiple solid supports (e.g., multiple beads) can be present in a compartment, or multiple copies of the bound oligonucleotide can be bound to each solid support, but all polynucleotides resulting from the polymerase extension reaction in the compartment will contain the same barcode sequence.

Preferred solid supports for use in the present methods are beads, for example spherical beads made of metals and/or polymeric materials and having diameters in the range of ~0.1 to 10 micrometers. Beads having other characteristics can be used instead or in addition. The solid support can be functionalized with a capture moiety to attach the bound oligonucleotide to the surface (FIG. 15, left). Examples of capture moieties include avidin, streptavidin, biotin, carboxyl groups, epoxy groups, hydroxyl groups, thiol groups, and gold. Some capture moieties have binding partners to which they bind specifically and non-covalently. For example, streptavidin takes biotin as its binding partner. Such a capture moiety can be coupled directly (e.g., covalently) to the solid support, and the binding partner can be coupled to the bound oligonucleotide, or vice versa, so that the bound oligonucleotide is bound to the solid support through a non-covalent interaction. Other capture moieties provide a direct covalent linkage between the bound oligonucleotide and solid support.

The bound oligonucleotide is preferably a single-stranded DNA molecule that is bound to the solid support at its 5' end. Thus, 3' end of the bound oligonucleotide is free in solution and, when hybridized to the barcode oligonucleotide, can be extended by an enzyme such as DNA polymerase. The extension reaction is templated using the barcode oligonucleotide, so that the barcode sequence gets incorporated into the DNA strand bound to the bead. If desired, the bound oligonucleotide and/or the barcode oligonucleotide can have sequences designed to minimize intramolecular secondary structure.

The barcode oligonucleotide can contain sequence regions discussed above, such as a universal priming sequence and/or a binding site. Upon performing a primer extension reaction with the bound oligonucleotide and the barcode oligonucleotide, these sequence regions will be incorporated into the polynucleotide bound to the solid support. If the polynucleotide is subsequently used as a barcode adapter template, the sequence regions will also be present in barcode adapter molecules generated from the template. Other sequences, such as an RNAP promoter and/or a nicking endonuclease restriction site, can be included in the barcode oligonucleotide to facilitate the enzymatic production of barcode adapter molecules. The RNAP promoter can be selected from the group consisting of T7, T3, and SP6 promoters. The nicking endonuclease restriction site can be selected from the group consisting of Nt.BbvCI, Nt.BspQI, Nt.BsmAI, Nt.BstNBI, Nt.AlwI, and Nt.BsmAI sites. The binding site within the barcode oligonucleotide can contain one or more G nucleotides.

In some embodiments, the barcode sequence and other sequence regions are incorporated into the bound oligonucleotide and/or the polynucleotide attached to solid support using PCR (FIG. 15, right). In these embodiments, the barcode oligonucleotide serves as a template for PCR, and the bound oligonucleotide serves as a primer, with enzymatic extension of the bound oligonucleotide proceeding from its 3' end. The barcode oligonucleotide also includes a 5' sequence identical or complementary to a PCR reverse primer sequence. Thus, a reverse primer can anneal to the 5' end of the barcode oligonucleotide (or its complement) and prime extension in a direction opposite that of the bound oligonucleotide. If desired, this reverse primer can be fluorophore-labeled, so that polynucleotides generated by PCR and attached to the solid support are fluorescent. The label can be used to determine whether a solid support (for example, a bead) has been successfully attached to a polynucleotide that includes the barcode sequence.

The above methods can be performed in a single step. In other embodiments of the present methods, a polynucleotide containing a barcode sequence is attached to a solid support in multiple steps. In these embodiments, the barcode sequence is made up of several sequence regions, for example $S1_x$, W, and $S2_y$ regions. These sequence regions can be introduced into the polynucleotide as part of two or more barcode oligonucleotides, with each barcode oligonucleotide being used in a separate step or enzymatic reaction. In the polynucleotide resulting from the separate steps, the $S1_x$, W, and $S2_y$ regions are not necessarily contiguous. Various $S1_x$, W, and $S2_y$ sequences can be combined on different solid supports to form different barcodes sequences or libraries of barcode sequences.

To attach a polynucleotide to a solid support in multiple steps, wherein the polynucleotide contains a barcode sequence, a solid support and oligonucleotide bound to the solid support are provided as described above. The solid support and bound oligonucleotide can be provided in a hydrophilic compartment of an emulsion, or in any other desired reaction volume. Also provided is a first barcode oligonucleotide (FIG. 16, top and middle). The bound oligonucleotide comprises an $S1_x$ sequence and a sequence complementary to a 3' sequence of the first barcode oligonucleotide. The first barcode oligonucleotide comprises a W sequence. In the first step of the multistep procedure, a polymerase extension reaction or a ligation reaction is performed to incorporate the W sequence into the bound oligonucleotide. Thus, after this step, the $S1_x$ sequence and W sequence are present in the same nucleic acid strand bound to the solid support. If an extension reaction is used, the bound oligonucleotide can serve as a primer and the first barcode oligonucleotide can serve as a template, as discussed above for the single-step procedure, so that the bound oligonucleotide is extended from its 3' end. In some embodiments, a portion of the first barcode oligonucleotide that is complementary to the $S1_x$ sequence in the bound oligonucleotide contains an inosine tract.

Subsequently, a second barcode oligonucleotide is provided to incorporate a $S2_y$ sequence into the bound oligonucleotide (FIG. 16, bottom). The second barcode oligonucleotide comprises the $S2_y$ sequence, as well as a 3' sequence complementary to the 3' end of the bound oligonucleotide resulting from the first step of the multistep procedure. Thus, the second barcode oligonucleotide may include a sequence region complementary or identical to a portion of the first barcode oligonucleotide. The second barcode oligonucleotide is reacted with the bound oligonucleotide (now extended to include both the $S1_x$ sequence and the W sequence) through a polymerase extension reaction or ligation reaction. After this step, the $S1_x$, W, and $S2_y$ sequences are all present in the same nucleic acid strand bound to the solid support.

As desired, the same or different reaction conditions can be used for the first and second steps of a multistep procedure to attach a polynucleotide to a solid support. For example, the same enzyme (e.g., a DNA polymerase) or different enzymes (e.g., a DNA polymerase and a ligase) can be used for reactions of the first barcode oligonucleotide and second barcode oligonucleotide, although using the same enzyme can be more convenient. To mix reagents and the solid support for consecutive steps, reagents can be apportioned into reaction volumes, and reaction volumes can be split, combined, or otherwise handled, all as desired. For example, the solid support and bound oligonucleotide can be distributed into many reaction volumes, and different first barcode oligonucleotides can be added to each reaction volume, so that different W sequences are coupled to the same $S1_x$ sequence. Each of these reaction volumes can in turn be split into many more volumes for the addition of the second barcode oligonucleotide, so that many $S2_y$ sequences are coupled to each W sequence. In some embodiments, solid supports are washed to remove unbound oligonucleotides. In some embodiments, solid supports are heated after incorporating the W sequence into the bound oligonucleotide, to melt the duplex of the bound oligonucleotide and first barcode oligonucleotide, and allow the bound oligonucleotide and second barcode oligonucleotide to anneal.

Sequence regions that can be included in barcode adapter molecules and/or barcode adapter templates, such as a universal priming sequence, binding site, RNAP promoter, or nicking endonuclease restriction site, can be distributed between the first barcode oligonucleotide and the second barcode oligonucleotide as desired. For example, all such sequences can be included in one barcode oligonucleotide, or some can be included in one barcode oligonucleotide and some can be included in the other. In some embodiments, a chosen barcode oligonucleotide, being either the first barcode oligonucleotide or the second barcode oligonucleotide, further comprises a universal priming sequence and a binding site. In some embodiments, this chosen barcode oligonucleotide also comprises an RNAP promoter or a nicking endonuclease restriction site. It will be recognized that the present methods provide many options for incorporating different sequence regions into barcode adapter templates. The optimal designs of these templates and the oligonucleotides used to prepare them may depend on what mechanisms are used for enzymatically generating barcode adapter molecules and barcoding RNAs.

Any of the methods described herein for attaching polynucleotides to solid supports can be used to prepare one or more solid supports for use in barcoding samples, cells, or RNAs. The polynucleotide(s) attached to each solid support includes barcode sequences and can serve as a barcode adapter template. The present methods can also be used to prepare a barcode library, which includes a plurality of solid supports, each associated with a barcode sequence. Any two solid supports (for example, beads) can have barcode sequences that differ from each other in whole or in part. In some embodiments, every solid support in the barcode library is associated with a different barcode sequence.

A barcode adapter template bead prepared according to the present methods includes a bead bound to a barcode adapter template. The bead can be bound to multiple copies of the template molecule, for example at least 10, 30, 100, 300, 1,000, 3,000, 10,000, 30,000, 100,000, 300,000, or 1,000,000 copies. In some embodiments, each copy of the template molecule bound to one bead includes the same barcode sequence. In embodiments where the template molecule has a barcode sequence of the form $S1_x$-W-$S2_y$, each copy of the template molecule bound to one bead includes the same $S1_x$, W, and/or $S2_y$ sequence. The present methods also allow preparation of a beaded barcode library comprising a plurality of barcode adapter template beads. Every bead in the library can be associated with a different barcode sequence, and copies of barcode adapter templates on each bead can comprise the same barcode sequence.

In some embodiments, the present methods can be used to prepare a polynucleotide library by physically capturing cDNAs prepared from or obtained from one or more samples (e.g., cells) on barcode adapter template beads. Each bead includes a template molecule with a cDNA binding site at the 3' end. The bead can be contacted with an enzyme to render the binding site single-stranded (for example, leaving a 3' overhang at the end of the template molecule free in solution). The bead is then contacted with one or more cDNAs from a sample such that the cDNAs bind to copies of the template molecule through the binding sites. In preferred embodiments, the binding site includes one or more G nucleotides, for example a poly-G tract, and is complementary to the non-templated poly-C tract added to the end of cDNAs by reverse transcriptase.

The beads in a polynucleotide library can be used as desired, for example to sequence the cDNAs from a plurality of samples or separate the cDNAs from different samples. In the latter case, beads corresponding to different samples can be pelleted using centrifugation or magnetism, and then resuspended and separated using standard methods. If desired, following the binding of cDNAs to template molecules on a bead, the template molecules can be enzymatically extended, thereby incorporating the cDNA sequences into DNA duplexes bound the bead and associating these sequences with a barcode sequence. If the number of copies of cDNA molecules from a sample is comparable to the number of copies of the barcode adapter template on a bead, then these cDNA molecules can be captured on a small number of beads (for example, at most about 1, 3, 10, 30, 100, 300, or 1000 beads per sample). RNAs from samples can be reverse transcribed using standard methods or as discussed above to generate cDNA. B cells (e.g., plasmablasts, memory B cells, and plasma cells) can be used as samples, and in some embodiments the cDNA is a B-cell derived variable immunoglobulin region.

II. COMPOSITIONS

A. Polynucleotides

In some aspects, a polynucleotide can include a cDNA region. In some aspects, a polynucleotide can include a sample identification (barcode)-adapter region. In some aspects, a polynucleotide can include a sample identification (barcode) region. In some aspects, a polynucleotide can include an adapter region. In some aspects, a polynucleotide can include a universal primer region. In some aspects, a polynucleotide can include an amplicon region. In some aspects, a polynucleotide can include a plate identification region. In some aspects, a polynucleotide can include a first plate identification region. In some aspects, a polynucleotide can include a second plate identification region. In some aspects, a polynucleotide can include a restriction site region. In some aspects, a polynucleotide can include a first restriction site region. In some aspects, a polynucleotide can include a second restriction site region. In some aspects, a polynucleotide can include a sequencing region. In some aspects, a polynucleotide can include a first sequencing region. In some aspects, a polynucleotide can include a second sequencing region.

In some aspects, a polynucleotide can include a plurality of any region described herein. For example, a polynucleotide can include a first sample identification (barcode) region and a second sample identification (barcode) region. In some aspects, the first sample identification (barcode) region and the second sample identification (barcode) region are identical or substantially identical. In some aspects, the first sample identification (barcode) region and the second sample (barcode) identification region are distinct. In some aspects, an identification (barcode) region is coupled to a variable immunoglobulin region.

In some aspects the sequence of a region will be at least long enough to serve as a target sequence for a primer or a probe in a PCR reaction. In some aspects, a region can be 1 to greater than 5000 base pairs in length. For example, a region can be from 1-10,000 nucleotides in length, e.g., 2-30 nucleotides in length, including all sub-ranges therebetween. As non-limiting examples, a region can be from 1-30 nucleotides, 1-26 nucleotides, 1-23 nucleotides, 1-22 nucleotides, 1-21 nucleotides, 1-20 nucleotides, 1-19 nucleotides, 1-18 nucleotides, 1-17 nucleotides, 18-30 nucleotides, 18-26 nucleotides, 18-23 nucleotides, 18-22 nucleotides, 18-21 nucleotides, 18-20 nucleotides, 19-30 nucleotides, 19-26 nucleotides, 19-23 nucleotides, 19-22 nucleotides, 19-21 nucleotides, 19-20 nucleotides, 20-30 nucleotides, 20-26 nucleotides, 20-25 nucleotides, 20-24 nucleotides, 20-23 nucleotides, 20-22 nucleotides, 20-21 nucleotides, 21-30 nucleotides, 21-26 nucleotides, 21-25 nucleotides, 21-24 nucleotides, 21-23 nucleotides, or 21-22 nucleotides. In some aspects, a region can be about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or more nucleotides in length. In some aspects, a region can be less than 50, 50-100, 100-200, 200-300, 300-400, 400-500, 500-600, 600-700, 700-800, 800-900, 900-1000, or greater than 1000 nucleotides in length. In some aspects, a region can be less than 1000, 1000-2000, 2000-3000, 3000-4000, 4000-5000, 5000-6000, 6000-7000, 7000-8000, 8000-9000, 9000-10000, or greater than 10000 nucleotides in length. In some aspects, a region can include at least two nucleotides, at least 3, at least 4, at least 5, at least 6, at least 7, at least 8, at least 9, at least 10, at least 15, at least 20 or more nucleotides of a polynucleotide disclosed herein.

In some aspects a polynucleotide can be derived from or associated with a single sample. In some aspects a region can be derived from or associated with a single sample. In some aspects, a cDNA region can be derived from or associated with a single sample. In some aspects, an amplicon region can be derived from or associated with a single sample. A "single sample" includes a sample comprising polynucleotides that is taken from a single source. In some aspects, a single source includes a sample taken at a particular time point or at a particular location, e.g., in a subject or flask of cells or plate of cells. In some aspects, a first single sample is taken from a first subject at a first time point and a second single sample is taken from the first subject at a second time point that is distinct from the first time point. In some aspects, a first single sample is taken from a first subject at a first location and a second sample is taken from the first subject at a second location that is distinct from the first location. In some aspects, a first single sample is taken from a first subject at a time point and a second single sample is taken from a second subject at a time point. In some aspects, a first single sample is taken from a first subject at a location and a second sample is taken from a second subject at a location. In one embodiment, a sample comprises polynucleotides that include mRNA derived from one or more B cells. In another embodiment, a sample comprises polynucleotides including cDNA derived from one or more B cells. In another embodiment, a single sample comprises mRNA derived from one or more B cells sorted into a single well of a 96-well or 384-well plate. Samples are generally derived from a prokaryotic cell(s) (e.g., a bacterial cell(s)), a eukaryotic cell(s) (e.g., a mammalian and yeast cell(s)), or other sources of genetic material such as a virus or phage. The term "mammal" or "mammalian" as used herein includes both humans and non-humans and include but is not limited to humans, non-human primates, canines, felines, murines, bovines, equines, and porcines. In some aspects, the methods of the invention are applied to single samples in a plate with at least 96 wells, at least 384 wells, at least 1536 wells, or more wells. In further aspects, the methods of the invention are applied to single samples in at least one, two, three, four, five, six, seven, eight, ten, fifteen, twenty, thirty or more plates with at least 96 wells each.

In some aspects a 5' adapter region sequence and/or a sample identification region are added to all cDNAs from a single sample, e.g., during RT and not just to Ig genes. In some aspects, 3' gene specific primers (GSPs) can be used to amplify any expressed gene in the single sample. In some aspects, genes are amplified that have a 5' variable region, e.g., T cell receptors and B cell receptors without needing multiple degenerate 5' primers to amplify the gene(s) of interest. GSPs can include primers specific for IgG, IgM, IgD, IgA, IgE, TCR chains, and other genes of interest.

In some aspects, multiple rounds of PCR can also be performed, e.g., using nested GSPs. For such nested GSPs, the GSP for the second round of PCR hybridizes to its target gene sequence at a position 5' along that sequence relative to the position hybridized to by the GSP used in the first round of PCR.

In some aspects, cDNA region or an amplicon region can include a DNA polynucleotide. In some aspects, cDNA region or an amplicon region can include a cDNA polynucleotide. In some aspects, cDNA region or an amplicon region can include an RNA polynucleotide hybridized to a DNA polynucleotide. In some aspects, cDNA region or an amplicon region can include an mRNA polynucleotide hybridized to a cDNA polynucleotide.

In some aspects, a universal primer region is not fully complementary to any human exon. In some aspects, a universal primer region is not fully complementary to any expressed human gene. In some aspects, a universal primer region has minimal secondary structure.

In some aspects, an amplicon region comprises an immunoglobulin heavy chain amplicon sequence. In some aspects, an amplicon region comprises an immunoglobulin light chain amplicon sequence. In some aspects, an amplicon region comprises a T cell receptor alpha amplicon sequence. In some aspects, an amplicon region comprises a T cell receptor beta amplicon sequence.

In some aspects, a polynucleotide is present in a library of polynucleotides and can be differentiated from other polynucleotides present in the library based on a region of the polynucleotide.

In some aspects, the sequence of the sample identification region of each polynucleotide in a library derived from a first single sample is distinct from the sequence of the sample identification region of the other polynucleotides in the library derived from one or more samples distinct from the first single sample. In some aspects, the sequence of the sample identification region of each polynucleotide in a library derived from a first single sample differs by at least 1 nucleotide from the sequence of the sample identification region of the other polynucleotides in the library derived from one or more samples distinct from the first single sample. In some aspects, the sequence of the sample identification region of each polynucleotide in a library derived from a first single sample differs by at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more nucleotides from the sequence of the sample identification region of the other polynucleotides in the library derived from one or more samples distinct from the first single sample. In some aspects, the sequence of the sample identification region of each polynucleotide in a library derived from a first single sample can be about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 81, 82, 83, 84, 85, 86, 87, 88, 89, 90, 91, 92, 93, 94, 95, 96, 97, 98, 99, or less than 100% identical to the sequence of the sample identification region of the other polynucleotides in the library derived from one or more samples distinct from the first single sample. In some aspects, the sequence of the sample identification region of each polynucleotide in a library derived from a first single sample is less than 100% identical to the sequence of the sample identification region of the other polynucleotides in the library derived from one or more samples distinct from the first single sample. In some aspects, a sample-identification region acts as a digital barcode on all $1^{st}$ strand cDNA reverse transcribed from a single sample. In some aspects, the sample identification region is at least 1 nucleotide in length. In some aspects, a sample-identification region can comprise at least 3 nucleotides, and sample-identification regions can differ from each other by at least 1 nucleotide. In one embodiment, sample-identification regions are 3-15 nucleotides in length and differ from each other by at least 1 nucleotide. In some aspects, sample-identification regions can comprise at least 64 variants (using sample-identification regions 3 nucleotides in length with each sample-ID differing from each other by at least 1 nucleotide), or in some aspects larger numbers of variants. In some aspects, the sequence attached 3' to the sample-identification region can be an adapter region comprising at least 1 G. In a preferred embodiment, the sequence attached 3' to the sample-identification region can be an adapter region comprising at least 2 G's. In one embodiment, a sequence attached to the 5' end of a sample-identification region is a universal primer sequence that can be used during PCR amplification to avoid the need for the subsequent addition of a 5' universal primer sequence (by ligation or another method) or the use of multiple degenerate 5' primers to amplify genes with variable 5' regions. In some aspects, the sequence of the first plate identification region of each polynucleotide in a library derived from a first set of single samples is distinct from the sequence of the first plate identification region of the other polynucleotides in the library derived from one or more single sample sets distinct from the first set of single samples. In some aspects, the sequence of the first plate identification region of each polynucleotide in a library derived from the first set of single samples differs by at least 1 nucleotide from the sequence of the first plate identification region of the other polynucleotides in the library derived from one or more single sample sets distinct from the first set of single samples. In some aspects, the sequence of the first plate identification region of each polynucleotide in a library derived from the first set of single samples differs by at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more nucleotides from the sequence of the first plate identification region of the other polynucleotides in the library derived from one or more single sample sets distinct from the first set of single samples. In some aspects, the sequence of the first plate identification region of each polynucleotide in a library derived from the first set of single samples can be about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 81, 82, 83, 84, 85, 86, 87, 88, 89, 90, 91, 92, 93, 94, 95, 96, 97, 98, 99, or less than 100% identical to sequence of the first plate identification region of the other polynucleotides in the library derived from one or more single sample sets distinct from the first set of single samples. In some aspects, the sequence of the first plate identification region of each polynucleotide in a library derived from the first set of single samples is less than 100% identical to sequence of the first plate identification region of the other polynucleotides in the library derived from one or more single sample sets distinct from the first set of single samples. In some aspects, the sequence of the second plate identification region of each polynucleotide in a library derived from a first set of single samples is distinct from the sequence of the second plate identification region of the other polynucleotides in the library derived from one or more single sample sets distinct from the first set of single samples. In some aspects, the sequence of the second plate identification region of each polynucleotide in a library derived from the first set of single samples differs by at least 1 nucleotide from the sequence of the second plate identification region of the other polynucleotides in the library derived from one or more single sample sets distinct from the first set of single samples. In some aspects, the sequence of the second plate identification region of each polynucleotide in a library derived from the first set of single samples differs by at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more nucleotides from the sequence of the second plate identification region of the other polynucleotides in the library derived from one or more single sample sets distinct from the first set of single samples. In some aspects, the sequence of the second plate identification region is identical to the sequence of the first plate identification region on a polynucleotide. In some aspects, the sequence of the second plate identification region of each polynucleotide in a library derived from the first set of single samples can be about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 81, 82, 83, 84, 85, 86, 87, 88, 89, 90, 91, 92, 93, 94, 95, 96, 97, 98, 99, or less than 100% identical to sequence of the second plate identification region of the other polynucleotides in the library derived from one or more single sample sets distinct from the first set of single samples. In some aspects, the sequence of the second plate identification region of each polynucleotide in a library derived from the first set of single samples is less than 100% identical to sequence of the second plate identification region of the other polynucleotides in the library derived from one or more single sample sets distinct from the first set of single samples. In some aspects, a plate-identification region (e.g., a first plate identification region or a second plate identification region) can comprise at least 2 nucleotides, and plate-identification regions differ from each other by at least 1 nucleotide. In one embodiment, plate-identification regions are 2-10 nucleotides in length and differ from each other by at least 1 nucleotide. In some aspects, use of plate-identification regions is found in only some embodiments, as the use of a larger number of different sample-identification regions (one per single sample to be analyzed) can eliminate the need for plate-identification regions. In some aspects, plate-identification regions are used to reduce the number of unique oligonucleotides containing a sample-identification region that need to be synthesized.

In some aspects, a polynucleotide includes one or more adapter regions. In some aspects, an adapter region includes one or more G's. In some aspects, an adapter region includes 2, 3, 4, 5, 6, 7, 8, 9, 10 or more G's. In some aspects, adapter regions are attached to the 3' ends of cDNAs using the template switching property of MMLV H⁻ reverse transcriptases. Different methods to attach adapter regions exist, including but not limited to, doing PCR with primers with 5' flanking adapter region sequences, sticky and blunt end ligations, template-switching-mediated addition of nucleotides, or other methods to covalently attach nucleotides to the 5' end, to the 3' end, or to the 5' and 3' ends of the polynucleotides. These methods can employ properties of enzymes commonly used in molecular biology. PCR can use, e.g., thermophilic DNA polymerase. Sticky ends that are complementary or substantially complementary are created through either cutting dsDNA with restriction enzymes that leave overhanging ends or through 3' tailing activities of enzymes such as TdT (terminal transferase). Sticky and blunt ends can then be ligated with a complementary adapter region using ligases such as T4 ligase. Template-switching utilizes the 3' tailing activity of MMLV H⁻ reverse transcriptase to add one or more cytosines (C's) to the 3' end of cDNAs and its ability to switch template from mRNA to an adapter region with complementary G's. In some aspects, a cDNA includes 1, 2, 3, 4, 5, 6, 7, 8, 9, 10 or more C's on its 3' end.

In some aspects, a polynucleotide includes one or more restriction site regions. Restriction site regions include one or more restriction sites. Restrictions sites can include: NheI, XhoI, BstBI, EcoRI, SacII, BbvCI, PspXI, AgeI, ApaI, KpnI, Acc65I, XmaI, BstEII, DraIII, PacI, FseI, AsiSI, and AscI. In some aspects, any rare 8-cutter enzyme restriction site can be used.

In some aspects, one or more regions of a polynucleotide described herein can be operatively coupled to one or more other regions of the polynucleotide. In some aspects, two or more distinct regions of a single polynucleotide can be operatively coupled. For example, a universal primer region can be operatively coupled to an adapter region. In some aspects two or more regions can be operatively coupled together that are substantially identical to each other in sequence or identical in description. For example, a first sample identification region can be operatively coupled to a second sample identification region. In some aspects, the sequences of the first sample identification region and the second sample identification region are identical or substantially identical. In some aspects, the sequences of the first sample identification region and the second sample identification region are different or distinct.

In some aspects, one or more regions of a polynucleotide described herein can be coupled to one or more other regions of the polynucleotide. In some aspects, two or more distinct regions of a single polynucleotide can be coupled. For example, a universal primer region can be coupled to an adapter region. In some aspects two or more regions can be coupled together that are substantially identical to each other in sequence or identical in description. For example, a first sample identification region can be coupled to a second sample identification region. In some aspects, the sequences of the first sample identification region and the second sample identification region are identical or substantially identical. In some aspects, the sequences of the first sample identification region and the second sample identification region are different or distinct.

In some aspects, a polynucleotide includes the sequence 5'-A-B-3', wherein A is a sample identification region, and wherein B is an adapter region. In some aspects, a polynucleotide includes the sequence 5'-A-B-C-3', wherein A is a universal primer region, wherein B is a sample identification region, and wherein C is an adapter region. In some aspects, a polynucleotide includes the sequence 5'-A-B-C-3', wherein A is a sample identification region, wherein B is an adapter region, and wherein C is an amplicon region derived from a single sample. In some aspects, a polynucleotide includes the sequence 5'-A-B-C-D-3', wherein A is a universal primer region, wherein B is a sample identification region, wherein C is an adapter region, and wherein D is an amplicon region derived from a single sample. In some aspects, a polynucleotide includes the sequence 5'-A-B-C-

D-E-3', wherein A is a plate identification region, wherein B is a universal primer region, wherein C is a sample identification region, wherein D is an adapter region, and wherein E is an amplicon region derived from a single sample. In some aspects, a polynucleotide includes the sequence 5'-A-B-C-D-E-F-3', wherein A is a first restriction site region, wherein B is a universal primer region, wherein C is a sample identification region, wherein D is an adapter region, wherein E is an amplicon region derived from a single sample, and wherein F is a second restriction site region.

In some aspects, the regions of each of the above sequences can be rearranged in a different order, e.g., 5'-C-A-D-B-3' or 5'-E-A-C-B-D-F-3' or 5'-B-A-3'. In some aspects, one or more regions of the above sequences can be deleted, e.g., 5'-A-D-3' or 5'-B-C-3'. In some aspects, one or more additional regions can be added to the above sequences, e.g., 5'-A-A$_2$-B-3' or 5'-A-B-C-D-E-F-G-3'. In such examples the one or more additional regions can be any region disclosed herein or equivalents thereof. In some aspects, one or more regions of the sequences above can be modified, e.g., methylated.

In some aspects, a polynucleotide can include an adapter molecule. In some aspects, a polynucleotide adapter molecule can include a universal primer region, a sample identification region, and an adapter region, wherein the 3' end of the universal primer region is coupled to the 5' end of the sample identification region, and wherein the 3' end of the sample identification region is coupled to the 5' end of the adapter region. In some aspects, an adapter molecule includes a polynucleotide comprising at least 2 nucleotides that bind to C's added by a reverse transcriptase at the 3' end of a 1st strand cDNA. In some aspects, an adapter molecule includes a deoxyribose polynucleotide comprising 3-6 G's (DNA G's). In another embodiment, an adapter molecule includes a ribose polynucleotide consisting of 3-6 G's (RNA G's). In other embodiments, the adapter molecule can utilize nucleotide analogues, such locked nucleic acids (LNAs), e.g., LNA G's. In other embodiments, the nucleotide base may also be a universal or degenerate base such as 5-nitroindole and 3-nitropyrrole that can base-pair to C's as well as other nucleotides, in any combination.

In some aspects, a polynucleotide can include a primer or a probe. In some aspects, a primer can include a universal primer region and a plate identification region, and wherein the 3' end of the plate identification region is coupled to the 5' end of the universal primer region.

In some aspects, a composition can include a polynucleotide composition library. In some aspects, a polynucleotide composition library includes a plurality of polynucleotide compositions. In some aspects each composition is present in a separate container. In some aspects, a container can be a test tube. In some aspects, a container can be a well in a plate. In some aspects, a container can be a well in a 96-well plate. In some aspects, a container can be a well in a 384-well plate. In some aspects, each composition comprises a cDNA region derived from a single sample. In some aspects, each composition comprises a sample identification-adapter region comprising a sample identification region coupled to an adapter region. In some aspects the sequence of the sample identification region of each sample identification-adapter region in a library is distinct from the nucleotide sequence of the sample identification region of the other sample identification-adapter regions present in each separate container in the library. In some aspects the sample identification-adapter region is attached to the cDNA region. In some aspects the sample identification-adapter region is attached to the cDNA region by binding between their 3' regions. In some aspects the sample identification-adapter region is attached to the cDNA region by G:C binding. In some aspects, the cDNA region comprises an RNA polynucleotide hybridized to a DNA polynucleotide. In some aspects, the cDNA region comprises an mRNA polynucleotide hybridized to a cDNA polynucleotide.

In some aspects, the plurality of polynucleotide compositions in a polynucleotide library can comprise at least 2, at least 3, at least 10, at least 30, at least 100, at least 300, at least 1000, at least 3000, at least 10,000, at least 30,000, at least 100,000, at least 300,000, at least 1,000,000, at least 3,000,000, at least 10,000,000, at least 30,000,000, or more members. In other aspects, the plurality of polynucleotide compositions in a polynucleotide library can comprise at least 2, at least 3, at least 10, at least 30, at least 100, at least 300, at least 1000, at least 3000, at least 10,000, at least 30,000, or more genes of a cell sample's whole transcriptome. In other aspects, the plurality of polynucleotide compositions in a polynucleotide library comprises at least 1, at least 2, at least 3, at least 10, at least 30, at least 100, at least 300, at least 1000, at least 10,000, at least 100,000, at least 1,000,000, at least 10,000,000, at least 1,000,000,000 or more of the different antibody species present in the blood of an individual. These the antibody species can be expressed by plasmablasts, plasma cells, memory B cells, long-lived plasma cells, naïve B cells, other B lineage cells, or combinations thereof.

B. Vectors

In some aspects, a composition can include a vector. The term "vector" is used to refer to a carrier nucleic acid molecule into which a nucleic acid sequence can be inserted for introduction into a cell where it can be replicated. Vectors can be used in the transformation of a host cell with a nucleic acid sequence. In some aspects, a vector can include one or more polynucleotides described herein. In one embodiment, a library of nucleic acid sequences encoding target polypeptides may be introduced into a population of cells, thereby allowing screening of a library. A nucleic acid sequence can be "exogenous" or "heterologous" which means that it is foreign to the cell into which the vector is being introduced or that the sequence is homologous to a sequence in the cell but in a position within the host cell nucleic acid in which the sequence is ordinarily not found. Vectors include plasmids, cosmids, and viruses (e.g., bacteriophage). One of skill in the art may construct a vector through standard recombinant techniques, which are described in Maniatis et al., 1988 and Ausubel et al., 1994, both of which references are incorporated herein by reference. In some aspects, a vector can be a vector with the constant regions of an antibody pre-engineered in. In this way, one of skill can clone just the VDJ regions of an antibody of interest and clone those regions into the pre-engineered vector.

The term "expression vector" refers to a vector containing a nucleic acid sequence coding for at least part of a gene product capable of being transcribed. In some cases, RNA molecules are then translated into a protein, polypeptide, or peptide. Expression vectors can contain a variety of "control sequences," which refer to nucleic acid sequences for the transcription and possibly translation of an operably linked coding sequence in a particular host organism. In addition to control sequences that govern transcription and translation, vectors and expression vectors may contain nucleic acid sequences that serve other functions as well.

In some aspects, a vector can include a promoter. In some aspects, a vector can include an enhancer. A "promoter" is a control sequence that is a region of a nucleic acid sequence at which initiation and rate of transcription are controlled. It may contain genetic elements at which regulatory proteins and molecules may bind such as RNA polymerase and other transcription factors. The phrases "operatively positioned," "operatively linked," "under control," and "under transcriptional control" mean that a promoter is in a correct functional location and/or orientation in relation to a nucleic acid sequence to control transcriptional initiation and/or expression of that sequence. A promoter may or may not be used in conjunction with an "enhancer," which refers to a cis-acting regulatory sequence involved in the transcriptional activation of a nucleic acid sequence.

A promoter may be one naturally associated with a gene or sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other prokaryotic cell, and promoters or enhancers not "naturally occurring," i.e., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology, including PCR, in connection with the compositions disclosed herein (see U.S. Pat. No. 4,683,202, U.S. Pat. No. 5,928,906, each incorporated herein by reference).

In some aspects, a promoter and/or enhancer that effectively directs the expression of the DNA segment in the cell type chosen for expression. One example of such promoter that may be used is the E. coli arabinose or T7 promoter. Those of skill in the art of molecular biology generally are familiar with the use of promoters, enhancers, and cell type combinations for protein expression, for example, see Sambrook et al. (1989), incorporated herein by reference. The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

In some aspects, vectors can include initiation signals and/or internal ribosome binding sites. A specific initiation signal also may be included for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

In some aspects, a vector can include sequences that increase or optimize the expression level of the DNA segment encoding the gene of interest. An example of such sequences includes addition of introns in the expressed mRNA (Brinster, R. L. et al. (1988) Introns increase transcriptional efficiency in transgenic mice. Proc. Natl. Acad. Sci. USA 85, 836-40; Choi, T. et al. (1991) A generic intron increases gene expression in transgenic mice. Mol. Cell. Biol. 11, 3070-4). Another example of a method for optimizing expression of the DNA segment is "codon optimization". Codon optimization involves insertion of silent mutations in the DNA segment to reduce the use of rare codons to optimize protein translation (Codon engineering for improved antibody expression in mammalian cells. Carton J M, Sauerwald T, Hawley-Nelson P, Morse B, Peffer N, Beck H, Lu J, Cotty A, Amegadzie B, Sweet R. Protein Expr Purif. 2007 October; 55(2):279-86. Epub 2007 Jun. 16.).

In some aspects, a vector can include multiple cloning sites. Vectors can include a multiple cloning site (MCS), which is a nucleic acid region that contains multiple restriction enzyme sites, any of which can be used in conjunction with standard recombinant technology to digest the vector (see Carbonelli et al., 1999, Levenson et al., 1998, and Cocea, 1997, incorporated herein by reference.) "Restriction enzyme digestion" refers to catalytic cleavage of a nucleic acid molecule with an enzyme that functions only at specific locations in a nucleic acid molecule. Many of these restriction enzymes are commercially available. Use of such enzymes is understood by those of skill in the art. Frequently, a vector is linearized or fragmented using a restriction enzyme that cuts within the MCS to enable exogenous sequences to be ligated to the vector. "Ligation" refers to the process of forming phosphodiester bonds between two nucleic acid fragments, which may or may not be contiguous with each other. Techniques involving restriction enzymes and ligation reactions are well known to those of skill in the art of recombinant technology.

In some aspects, a vector can include a termination signal. The vectors or constructs will generally comprise at least one termination signal. A "termination signal" or "terminator" is comprised of the DNA sequences involved in specific termination of an RNA transcript by an RNA polymerase. Thus, in certain embodiments, a termination signal that ends the production of an RNA transcript is contemplated. A terminator may be necessary in vivo to achieve desirable message levels.

Terminators contemplated for use include any known terminator of transcription described herein or known to one of ordinary skill in the art, including but not limited to, for example, rho dependent or rho independent terminators. In certain embodiments, the termination signal may be a lack of transcribable or translatable sequence, such as due to a sequence truncation.

In some aspects, a vector can include an origin of replication.

In order to propagate a vector in a host cell, it may contain one or more origins of replication sites (often termed "ori"), which is a specific nucleic acid sequence at which replication is initiated.

In some aspects, a vector can include one or more selectable and/or screenable markers. In certain embodiments, cells containing a nucleic acid construct may be identified in vitro or in vivo by including a marker in the expression vector. Such markers would confer an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

Usually the inclusion of a drug selection marker aids in the cloning and identification of transformants, for example, genes that confer resistance to neomycin, puromycin, hygromycin, DHFR, GPT, zeocin and histidinol are useful selectable markers. In addition to markers conferring a phenotype that allows for the discrimination of transformants based on the implementation of conditions, other types of markers including screenable markers such as GFP, whose basis is colorimetric analysis, are also contemplated. Alternatively, screenable enzymes such as chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selectable and screenable markers are well known to one of skill in the art.

In one aspect, the vector can express DNA segments encoding multiple polypeptides of interest. For example, DNA segments encoding both the immunoglobulin heavy chain and light chain can be encoded and expressed by a single vector. In one aspect, both DNA segments can be included on the same expressed RNA and internal ribosome binding site (IRES) sequences used to enable expression of the DNA segments as separate polypeptides (Pinkstaff J K, Chappell S A, Mauro V P, Edelman G M, Krushel L A., Internal initiation of translation of five dendritically localized neuronal mRNAs., Proc Natl Acad Sci USA. 2001 Feb. 27; 98(5):2770-5. Epub 2001 Feb. 20.). In another aspect, each DNA segment has its own promoter region resulting in expression of separate mRNAs (Andersen C R, Nielsen L S, Baer A, Tolstrup A B, Weilguny D. Efficient Expression from One CMV Enhancer Controlling Two Core Promoters. Mol Biotechnol. 2010 Nov. 27. [Epub ahead of print]).

C. Host Cells and Expression Systems

In some aspects, a composition can include a host cell. In some aspects, a host cell can include a polynucleotide or vector described herein. In some aspects, a host cell can include a eukaryotic cell (e.g., insect, yeast, or mammalian) or a prokaryotic cell (e.g., bacteria). In the context of expressing a heterologous nucleic acid sequence, "host cell" can refer to a prokaryotic cell, and it includes any transformable organism that is capable of replicating a vector and/or expressing a heterologous gene encoded by a vector. A host cell can, and has been, used as a recipient for vectors. A host cell may be "transfected" or "transformed," which refers to a process by which exogenous nucleic acid is transferred or introduced into the host cell. A transformed cell includes the primary subject cell and its progeny.

In particular embodiments, a host cell is a Gram negative bacterial cell. These bacteria are suited for use in that they possess a periplasmic space between the inner and outer membrane and, particularly, the aforementioned inner membrane between the periplasm and cytoplasm, which is also known as the cytoplasmic membrane. As such, any other cell with such a periplasmic space could be used. Examples of Gram negative bacteria include, but are not limited to, *E. coli, Pseudomonas aeruginosa, Vibrio cholera, Salmonella typhimurium, Shigella flexneri, Haemophilus influenza, Bordotella pertussi, Erwinia amylovora, Rhizobium* sp. The Gram negative bacterial cell may be still further defined as bacterial cell which has been transformed with the coding sequence of a fusion polypeptide comprising a candidate binding polypeptide capable of binding a selected ligand. The polypeptide is anchored to the outer face of the cytoplasmic membrane, facing the periplasmic space, and may comprise an antibody coding sequence or another sequence. One means for expression of the polypeptide is by attaching a leader sequence to the polypeptide capable of causing such directing.

Numerous prokaryotic cell lines and cultures are available for use as a host cell, and they can be obtained through the American Type Culture Collection (ATCC), which is an organization that serves as an archive for living cultures and genetic materials. An appropriate host can be determined by one of skill in the art based on the vector backbone and the desired result. A plasmid or cosmid, for example, can be introduced into a prokaryote host cell for replication of many vectors. Bacterial cells used as host cells for vector replication and/or expression include DH5-alpha, JM109, and KC8, as well as a number of commercially available bacterial hosts such as SURE™ Competent Cells and SOLOPACK™ Gold Cells (STRATAGENE™, La Jolla). In some aspects, other bacterial cells such as *E. coli* LE392 are contemplated for use as host cells.

Many host cells from various cell types and organisms are available and would be known to one of skill in the art. Similarly, a viral vector may be used in conjunction with a prokaryotic host cell, particularly one that is permissive for replication or expression of the vector. Some vectors may employ control sequences that allow it to be replicated and/or expressed in both prokaryotic and eukaryotic cells. One of skill in the art would further understand the conditions under which to incubate all of the above described host cells to maintain them and to permit replication of a vector. Also understood and known are techniques and conditions that would allow large-scale production of vectors, as well as production of the nucleic acids encoded by vectors and their cognate polypeptides, proteins, or peptides.

In some aspects, a host cell is mammalian. Examples include CHO cells, CHO-K1 cells, or CHO-S cells. Other mammalian host cells include NS0 cells and CHO cells that are dhfr−, e.g., CHO-dhfr−, DUKX-B11 CHO cells, and DG44 CHO cells.

Numerous expression systems exist that can comprise at least a part or all of the compositions disclosed herein. Expression systems can include eukaryotic expression systems and prokaryotic expression systems. Such systems could be used, for example, for the production of a polypeptide product identified as capable of binding a particular ligand. Prokaryote-based systems can be employed to produce nucleic acid sequences, or their cognate polypeptides, proteins and peptides. Many such systems are commercially and widely available. Other examples of expression systems comprise of vectors containing a strong prokaryotic promoter such as T7, Tac, Trc, BAD, lambda pL, Tetracycline or Lac promoters, the pET Expression System and an *E. coli* expression system.

D. Polypeptides

In some aspects, a composition can include a polypeptide. In some aspects, a polypeptide encoded by a polynucleotide described herein can be expressed, e.g., from a host cell. The terms "polypeptide" or "protein" include a macromolecule having the amino acid sequence of a native protein, that is, a protein produced by a naturally-occurring and non-recombinant cell; or it is produced by a genetically-engineered or recombinant cell, and comprise molecules having the amino acid sequence of the native protein, or molecules having deletions from, additions to, and/or substitutions of one or more amino acids of the native sequence. The term also includes amino acid polymers in which one or more amino acids are chemical analogs of a corresponding naturally-occurring amino acid and polymers. The terms "polypeptide" and "protein" encompass antigen binding proteins, antibodies, or sequences that have deletions from, additions to, and/or substitutions of one or more amino acids of antigen-binding protein. The term "polypeptide fragment" refers to a polypeptide that has an amino-terminal deletion, a carboxyl-terminal deletion, and/or an internal deletion as compared with the full-length native protein. Such fragments can also contain modified amino acids as compared with the native protein. In certain embodiments, fragments are about five to 500 amino acids long. For example, fragments can be at least 5, 6, 8, 10, 14, 20, 50, 70, 100, 110, 150, 200, 250, 300, 350, 400, or 450 amino acids long. Useful polypeptide fragments include immunologically functional fragments of antibodies, including binding domains. In the case of a binding antibody, useful fragments include but are not limited to a CDR region, a variable domain of a heavy and/or light chain, a portion of an antibody chain or just its variable region including two CDRs, and the like.

The term "isolated protein" means that a subject protein (1) is free of at least some other proteins with which it would normally be found, (2) is essentially free of other proteins from the same source, e.g., from the same species, (3) is expressed by a cell from a different species, (4) has been separated from at least about 50 percent of polynucleotides, lipids, carbohydrates, or other materials with which it is associated in nature, (5) is operably associated (by covalent or noncovalent interaction) with a polypeptide with which it is not associated in nature, or (6) does not occur in nature. Typically, an "isolated protein" constitutes at least about 5%, at least about 10%, at least about 25%, or at least about 50% of a given sample. Genomic DNA, cDNA, mRNA or other RNA, nucleic acids of synthetic origin, or any combination thereof can encode such an isolated protein. Preferably, the isolated protein is substantially free from proteins or polypeptides or other contaminants that are found in its natural environment that would interfere with its therapeutic, diagnostic, prophylactic, research or other use.

In some aspects, a polypeptide can include an antigen binding protein (ABP). An "antigen binding protein" ("ABP") as used herein means any protein that binds a specified target antigen. "Antigen binding protein" includes but is not limited to antibodies and binding parts thereof, such as immunologically functional fragments. Peptibodies are another example of antigen binding proteins. The term "immunologically functional fragment" (or simply "fragment") of an antibody or immunoglobulin chain (heavy or light chain) antigen binding protein, as used herein, is a species of antigen binding protein comprising a portion (regardless of how that portion is obtained or synthesized) of an antibody that lacks at least some of the amino acids present in a full-length chain but which is still capable of specifically binding to an antigen. Such fragments are biologically active in that they bind to the target antigen and can compete with other antigen binding proteins, including intact antibodies, for binding to a given epitope. In some embodiments, the fragments are neutralizing fragments. These biologically active fragments can be produced by recombinant DNA techniques, or can be produced by enzymatic or chemical cleavage of antigen binding proteins, including intact antibodies. Immunologically functional immunoglobulin fragments include, but are not limited to, Fab, a diabody (heavy chain variable domain on the same polypeptide as a light chain variable domain, connected via a short peptide linker that is too short to permit pairing between the two domains on the same chain), Fab', F(ab')2, Fv, domain antibodies and single-chain antibodies, and can be derived from any mammalian source, including but not limited to human, mouse, rat, camelid or rabbit. It is further contemplated that a functional portion of the antigen binding proteins disclosed herein, for example, one or more CDRs, could be covalently bound to a second protein or to a small molecule to create a therapeutic agent directed to a particular target in the body, possessing bifunctional therapeutic properties, or having a prolonged serum half-life. As will be appreciated by one of skill in the art, an antigen binding protein can include nonprotein components. Additional details about antigen binding proteins and antibodies such as modifications, variants, methods of making, and methods of screening can be found in U.S. Pat. Pub. 20110027287, herein incorporated by reference in its entirety for all purposes.

In some aspects, a polypeptide can include an antibody. The term "antibody" refers to an intact immunoglobulin of any isotype, or a fragment thereof that can compete with the intact antibody for specific binding to the target antigen, and includes, for instance, chimeric, humanized, fully human, and bispecific antibodies. An "antibody" is a species of an antigen binding protein. An intact antibody will generally comprise at least two full-length heavy chains and two full-length light chains, but in some instances can include fewer chains such as antibodies naturally occurring in camelids which can comprise only heavy chains. Antibodies can be derived solely from a single source, or can be "chimeric," that is, different portions of the antibody can be derived from two different antibodies. The antigen binding proteins, antibodies, or binding fragments can be produced in hybridomas, by recombinant DNA techniques, or by enzymatic or chemical cleavage of intact antibodies. Unless otherwise indicated, the term "antibody" includes, in addition to antibodies comprising two full-length heavy chains and two full-length light chains, derivatives, variants, fragments, and muteins thereof. Furthermore, unless explicitly excluded, antibodies include monoclonal antibodies, bispecific antibodies, minibodies, domain antibodies, synthetic antibodies (sometimes referred to herein as "antibody mimetics"), chimeric antibodies, humanized antibodies, human antibodies, antibody fusions (sometimes referred to herein as "antibody conjugates"), and fragments thereof, respectively. In some embodiments, the term also encompasses peptibodies.

A therapeutically effective amount of an ABP can be administered to a subject in need thereof. ABPs can be formulated in pharmaceutical compositions. These compositions can comprise, in addition to one or more of the ABPs, a pharmaceutically acceptable excipient, carrier, buffer, stabilizer or other materials well known to those skilled in the art. Such materials should be non-toxic and should not interfere with the efficacy of the active ingredient. The precise nature of the carrier or other material can depend on the route of administration, e.g. oral, intravenous, cutaneous or subcutaneous, nasal, intramuscular, intraperitoneal routes.

Pharmaceutical compositions for oral administration can be in tablet, capsule, powder or liquid form. A tablet can include a solid carrier such as gelatin or an adjuvant. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol can be included.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilizers, buffers, antioxidants and/or other additives can be included, as required.

ABP administration is preferably in a "therapeutically effective amount" or "prophylactically effective amount" (as the case can be, although prophylaxis can be considered therapy), this being sufficient to show benefit to the individual. The actual amount administered, and rate and timecourse of administration, will depend on the nature and severity of disease being treated. Prescription of treatment, e.g. decisions on dosage etc., is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in Remington's Pharmaceutical Sciences, 16th edition, Osol, A. (ed), 1980.

A composition can be administered alone or in combination with other treatments, either simultaneously or sequentially dependent upon the condition to be treated.

III. IMMUNE CELLS

A sample can include immune cells. The immune cells can include T cells and B cells. T-cells (T lymphocytes) include, for example, cells that express T cell receptors. B-cells include, for example, activated B cells, blasting B cells, plasma cells, plasmablasts, memory B cells, B1 cells, B2 cells, marginal-zone B cells, and follicular B cells. T cells include activated T cells, blasting T cells, Helper T cells (effector T cells or Th cells), cytotoxic T cells (CTLs), memory T cells, central memory T cells, effector memory T cells and regulatory T cells. A sample can include a single cell (e.g., a single T or B cell) or at least 1,000, at least 10,000, at least 100,000, at least 250,000, at least 500,000, at least 750,000, or at least 1,000,000 cells.

A. B Cells

As used herein a "B cell" refers to any cell that has at least one rearranged immunoglobulin gene locus. A B cell can include at least one rearranged immunoglobulin heavy chain locus or at least one rearranged immunoglobulin light chain locus. A B cell can include at least one rearranged immunoglobulin heavy chain locus and at least one rearranged immunoglobulin light chain locus. B cells are lymphocytes that are part of the adaptive immune system. B cells can include any cells that express antibodies either in the membrane-bound form as the B-cell receptor (BCR) on the cell surface or as secreted antibodies. B cells can express immunoglobulins (antibodies, B cell receptor). Antibodies can include heterodimers formed from the heavy and light immunoglobulin chains. The heavy chain is formed from gene rearrangements of the variable, diversity, and junctional (VDJ) genes to form the variable region, which is joined to the constant region. The light chain is formed from gene rearrangements of the variable and junctional (VJ) genes to form the variable region, which is then joined to the constant region. Owing to a large possible number of junctional combinations, the variable regions of the antibody gene (which is also the BCR) have huge diversity, enabling B cells to recognize any foreign antigen and mount a response against it.

B. B-Cell Activation and Differentiation

B cells are activated and differentiate when they recognize an antigen in the context of an inflammatory immune response. They usually include 2 signals to become activated, one signal delivered through BCR (a membrane-bound form of the rearranged immunoglobulin), and another delivered through CD40 or another co-stimulatory molecule. This second signal can be provided through interaction with helper T cells, which express the ligand for CD40 (CD40L) on their surface. B cells then proliferate and may undergo somatic hypermutation, where random changes in the nucleotide sequences of the antibody genes are made, and B cells whose antibodies have a higher affinity B cells are selected. They may also undergo "class-switching", in which the constant region of the heavy chain encoding the IgM isotype is switched to the constant region encoding the IgG, IgA, or IgE isotype. Differentiating B cells may end up as memory B cells, which are usually of higher affinity and classed switched, though some memory B cells are still of the IgM isotype. Memory B cells can also become activated and differentiate into plasmablasts and ultimately, into plasma cells. Differentiating B cells may also first become plasmablasts, which then differentiate to become plasma cells.

C. Affinity Maturation and Clonal Families

A clonal family is generally defined by the use of related immunoglobulin heavy chain and/or light chain V(D)J sequences by 2 or more samples. Related immunoglobulin heavy chain V(D)J sequences can be identified by their shared usage of V(D)J gene segments encoded in the genome. Within a clonal family there are generally subfamilies that vary based on shared mutations within their V(D)J segments, that can arise during B cell gene recombination and somatic hypermutation.

Activated B cells migrate and form germinal centers within lymphoid or other tissues, where they undergo affinity maturation. B cells may also undergo affinity maturation outside of germinal centers. During affinity maturation, B cells undergo random mutations in their antibody genes, concentrated in the complementary determining regions (CDRs) of the genes, which encode the parts of the antibody that directly bind to and recognize the target antigen against which the B cell was activated. This creates sub-clones from the original proliferating B cell that express immunoglobulins that are slightly different from the original clone and from each other. Clones compete for antigen and the higher-affinity clones are selected, while the lower-affinity clones die by apoptosis. This process results in the "affinity maturation" of B cells and consequently in the generation of B cells expressing immunoglobulins that bind to the antigen with higher affinity. All the B cells that originate from the same 'parent' B cell form clonal families, and these clonal families include B cells that recognize the same or similar antigenic epitopes. In some aspects, we expect that clones present at higher frequencies represent clones that bind to antigen with higher affinity, because the highest-affinity clones are selected during affinity maturation. In some aspects, clones with different V(D)J segment usage exhibit different binding characteristics. In some aspects, clones with the same V(D)J segment usage but different mutations exhibit different binding characteristics.

D. Memory B Cells

Memory B cells are usually affinity-matured B cells, and may be class-switched. These are cells that can respond more rapidly to a subsequent antigenic challenge, significantly reducing the time included for affinity-matured antibody secretion against the antigen from ~14 days in a naive organism to ~7 days.

E. Plasmablasts and Plasma Cells

Plasma cells can be either long-lived or short-lived. Long-lived plasma cells may survive for the lifetime of the organism, whereas short-lived plasma cells can last for 3-4 days. Long-lived plasma cells reside either in areas of inflammation, in the mucosal areas (in the case of IgA-secreting plasma cells), in secondary lymphoid tissues (such as the spleen or lymph nodes), or in the bone marrow. To reach these divergent areas, plasmablasts fated to become long-lived plasma cells may first travel through the bloodstream before utilizing various chemokine gradients to traffic to the appropriate areas. Plasmablasts are cells that are affinity matured, are typically classed-switched, and usually secrete antibodies, though generally in lower quantities than the quantity of antibody produced by plasma cells. Plasma cells are dedicated antibody secretors.

F. Characteristics of TCR and BCR Genes

Since identifying recombinations are present in the DNA of each individual adaptive immune cell as well as their associated RNA transcripts, either RNA or DNA can be sequenced. A recombined sequence from a T-cell or B-cell can also be referred to as a clonotype. The DNA or RNA can correspond to sequences from T-cell receptor (TCR) genes or immunoglobulin (Ig) genes that encode antibodies. For example, the DNA and RNA can correspond to sequences encoding alpha, beta, gamma, or delta chains of a TCR. In a majority of T-cells, the TCR is a heterodimer consisting of an alpha-chain and beta-chain. The TCR-alpha chain is generated by VJ recombination, and the beta chain receptor is generated by V(D)J recombination. For the TCR-beta chain, in humans there are 48 V segments, 2 D segments, and 13 J segments. Several bases may be deleted and others added (called N and P nucleotides) at each of the two junctions. In a minority of T-cells, the TCRs consist of gamma and delta chains. The TCR gamma chain is generated by VJ recombination, and the TCR delta chain is generated by V(D)J recombination (Kenneth Murphy, Paul Travers, and Mark Walport, Janeway's Immunology 7th edition, Garland Science, 2007, which is herein incorporated by reference in its entirety).

The DNA and RNA analyzed in the methods can correspond to sequences encoding heavy chain immunoglobulins (IgH) with constant regions (alpha, delta, gamma, epsilon, or mu) or light chain immunoglobulins (IgK or IgL) with constant regions lambda or kappa. Each antibody can have two identical light chains and two identical heavy chains. Each chain is composed of a constant (C) and a variable region. For the heavy chain, the variable region is composed of a variable (V), diversity (D), and joining (J) segments. Several distinct sequences coding for each type of these segments are present in the genome. A specific VDJ recombination event occurs during the development of a B-cell, marking that cell to generate a specific heavy chain. Diversity in the light chain is generated in a similar fashion except that there is no D region so there is only VJ recombination. Somatic mutation often occurs close to the site of the recombination, causing the addition or deletion of several nucleotides, further increasing the diversity of heavy and light chains generated by B-cells. The possible diversity of the antibodies generated by a B-cell is then the product of the different heavy and light chains. The variable regions of the heavy and light chains contribute to form the antigen recognition (or binding) region or site. Added to this diversity is a process of somatic hypermutation which can occur after a specific response is mounted against some epitope. In this process mutations occur in those B-cells that are able to recognize the specific epitope leading to greater diversity in antibodies that may be able to bind the specific epitope more strongly. All these factors contribute to great diversity of antibodies generated by the B-cells. Many billions and maybe more than a trillion distinct antibodies may be generated. The basic premise for generating T-cell diversity is similar to that for generating antibodies by B-cells. An element of T-cell and B-cell activation is their binding to epitopes. The activation of a specific cell leads to the production of more of the same type of cells leading to a clonal expansion.

Complementarity determining regions (CDR), or hypervariable regions, are sequences in the variable domains of antigen receptors (e.g., T cell receptor and immunoglobulin) that can bind an antigen. The chain of each antigen receptor contains three CDRs (CDR1, CDR2, and CDR3). The two polypeptides making T cells (alpha and beta) and immunoglobulin (IgH and IgK or IgL) contribute to the formation of the three CDRs.

The part of CDR1 and CDR2 that is coded for by TCR-beta lies within one of 47 functional V segments. Most of the diversity of CDRs is found in CDR3, with the diversity being generated by somatic recombination events during the development of T lymphocytes.

A great diversity of BCR is present inter and intra-individuals. The BCR is composed of two genes IgH and IgK (or IgL) coding for antibody heavy and light chains. Three Complementarity Determining Region (CDR) sequences that bind antigens and MHC molecules have the most diversity in IgH and IgK (or IgL). The part of CDR1 and CDR2 coded for by IgH lies within one of 44 functional V segments. Most of the diversity in naive B cells emerges in the generation of CDR3 through somatic recombination events during the development of B lymphocytes. The recombination can generate a molecule with one of each of the V, D, and J segments. In humans, there are 44 V, 27 D, and 6 J segments; thus, there is a theoretical possibility of more than 7,000 combinations. In a small fraction of BCRs (about 5%) two D segments are found. Furthermore, several bases may be deleted and others added (called N and P nucleotides) at each of the two junctions generating a great degree of diversity. After B cell activation a process of affinity maturation through somatic hypermutation occurs. In this process progeny cells of the activated B cells accumulate distinct somatic mutations throughout the gene with higher mutation concentration in the CDR regions leading to generating antibodies with higher affinity to the antigens. In addition to somatic hypermutation activated B cells undergo the process of isotype switching. Antibodies with the same variable segments can have different forms (isotypes) depending on the constant segment. Whereas all naive B cells express IgM (or IgD), activated B cells mostly express IgG but also IgM, IgA and IgE. This expression switching from IgM (and/or IgD) to IgG, IgA, or IgE occurs through a recombination event causing one cell to specialize in producing a specific isotype. There is one segment for each IgM, IgD, and IgE, two segments for IgA, and four segments for IgG.

IV. COMPUTER IMPLEMENTATIONS

In some aspects, one or more methods described herein can be implemented on a computer. In one embodiment, a computer comprises at least one processor coupled to a chipset. In some embodiments, the chipset is coupled to a memory, a storage device, a keyboard, a graphics adapter, a pointing device, and/or a network adapter. A display is typically coupled to the graphics adapter. In one embodiment, the functionality of the chipset is provided by a memory controller hub and an I/O controller hub. In another embodiment, the memory is coupled directly to the processor instead of the chipset.

The storage device is any device capable of holding data, like a hard drive, compact disk read-only memory (CD-ROM), DVD, or a solid-state memory device. The memory holds instructions and data used by the processor. The pointing device may be a mouse, track ball, or other type of pointing device, and is used in combination with the keyboard to input data into the computer system. The graphics adapter displays images and other information on the display. The network adapter couples the computer system to a local or wide area network.

As is known in the art, a computer can have different and/or other components than those described previously. In addition, the computer can lack certain components. Moreover, the storage device can be local and/or remote from the computer (such as embodied within a storage area network (SAN)).

As is known in the art, the computer is adapted to execute computer program modules for providing functionality described herein. As used herein, the term "module" refers to computer program logic utilized to provide the specified functionality. Thus, a module can be implemented in hardware, firmware, and/or software. In one embodiment, program modules are stored on the storage device, loaded into the memory, and executed by the processor.

Embodiments of the entities described herein can include other and/or different modules than the ones described here. In addition, the functionality attributed to the modules can be performed by other or different modules in other embodiments. Moreover, this description occasionally omits the term "module" for purposes of clarity and convenience.

V. KITS

Further disclosed herein are kits comprising adapter constructs described herein. A kit can comprise a plurality of solid supports coupled to adapter constructs described herein. In some embodiments, the kit comprises an adapter template library comprising a plurality of adapter templates. In some embodiments, the kit comprises an adapter template library comprising a plurality of adapter templates coupled to a plurality of solid supports. The kit can further comprise enzymes for generating an adapter molecule (e.g., a barcode adapter molecule) described herein from the adapter template construct by an enzymatic reaction. In some embodiments, the kit comprises a cell suspension buffer described herein.

A kit can include a polynucleotide, a polynucleotide library, a vector, and/or a host cell disclosed herein and instructions for use. The kits may comprise, in a suitable container, a polynucleotide, a polynucleotide library, a vector, and/or a host cell disclosed herein, one or more controls, and various buffers, reagents, enzymes and other standard ingredients well known in the art.

The container can include at least one well on a plate comprising one or more wells. The container can include at least one vial, test tube, flask, bottle, syringe, or other container means, into which a polynucleotide, a polynucleotide library, a vector, and/or a host cell may be placed, and in some instances, suitably aliquoted. Where an additional component is provided, the kit can contain additional containers into which this component may be placed. The kits can also include a means for containing the polynucleotide, a polynucleotide library, a vector, and/or a host cell and any other reagent containers in close confinement for commercial sale. Such containers may include injection or blow-molded plastic containers into which the desired vials are retained. Containers can include labeling with instructions for use and/or warnings.

VI. DEVICES

Embodiments of the present invention include devices for generating and transporting reaction volumes. These volumes can occur on a microfluidic scale and can be phase-separated from a carrier fluid. Examples of reaction volumes that can be handled by the devices include aqueous droplets in an inverse emulsion (i.e., a water/oil emulsion). The devices allow barcode adapter templates, barcode adapter molecules, samples (e.g., cells), and/or RNAs obtained from these samples to be encapsulated in droplets, separately or together. The devices also allow reagents to be introduced into droplets, so that barcode adapter molecules can be enzymatically generated and the RNAs from individual samples can be barcoded.

Non-limiting examples of devices as used and claimed herein are depicted in FIGS. 17-19. A skilled artisan will recognize that variations of these devices can also be constructed and used in the present methods. A device generally includes three microfluidic pathways, each coupled to a pressure source and a flow sensor. The pressure source for a microfluidic pathway drives fluid through the pathway, and the flow sensor, which occurs downstream of the pressure source, can be used to measure the rate of flow through the pathway. In some embodiments, the first pathway 101 and second pathway 102 merge at a first junction 104 to form a combined pathway, which then merges with the third pathway 103 at a second junction 105. The second junction occurs in a microfluidic droplet chip and can be a site where microfluidic droplets are generated.

Devices as described herein can be assembled from tubing and fluidics components available from IDEX Corporation (Lake Forest, Ill., U.S.A.), and using a microfluidic droplet chip available from Dolomite Microfluidics (Charlestown, Mass., U.S.A.). Some features of the microfluidic droplet chip are described in U.S. Pat. Nos. 7,268,167, 7,375,140, 7,717,615, 7,772,287, 8,741,192, and 8,883,864, which are incorporated herein by reference. Suitable pressure sources include syringe pumps and pressure pumps. Pressure pumps are available from Dolomite Microfluidics. The pressure sources can be controlled independently.

In some embodiments, the first and second microfluidic pathways transport aqueous solutions. Each pathway can include an injection port and a valve (e.g., a four-way valve) to bring a solution introduced in the injection port in-line with the pathway. In some embodiments, a reservoir holding an aqueous carrier fluid is disposed upstream of each four-way valve. The aqueous carrier fluid can mix with an aqueous solution in the four-way valve as the carrier fluid is driven downstream, or push a plug of the aqueous solution downstream toward the first junction. In some embodiments, a flow resistor is disposed in each microfluidic pathway.

Once an aqueous solution is introduced into the first or second microfluidic pathway, it can pass through a sample loop that meters the flow of the solution toward the first junction. Metering can be achieved as desired, for example using fluidic resistance or valves disposed along the sample loop. In some embodiments, one sample loop is associated with each of the first and second microfluidic pathways, and the sample loops are in contact with a thermal cooling unit. The thermal cooling unit can be included to prevent thermal denaturation of enzymes, nucleic acids, or other biological components in the aqueous solutions, or to establish optimal temperatures for enzymatic reactions. Portions of the thermal cooling unit in contact with the sample loops for the first and second microfluidic pathways can be controlled independently or jointly. Any substance or apparatus can be used as a thermal cooling unit provided that it can cause the temperatures of aqueous solutions passing through the sample loops to deviate from the ambient temperature. Examples of suitable thermal cooling devices are Peltier devices and ice bins.

In some embodiments, the aqueous solution transported through the first microfluidic pathway contains cells and barcode adapter template beads. In some embodiments, the aqueous solution transported through the second microfluidic pathway contains reagents for cell lysis and reagents for producing polynucleotides of interest (e.g., enzymes for generating barcode adapter molecules). The injection port, valve, and/or sample loop associated with each microfluidic pathway can be configured or customized to accommodate the contents of the aqueous solution passing through that pathway. For example, the sample loop associated with the first microfluidic pathway can have an enlarged interior diameter to accommodate cells and beads. It will be recognized many other options exist for allocating cells, beads, and reagents between the first and second microfluidic pathways, so that all of these components are combined at the first junction. For example, cells can be transported through the first microfluidic pathway and beads can be transported through the second microfluidic pathway. Each pathway can be configured as desired, in view of the contents of the aqueous solution it carries.

The combined pathway resulting from the merger of the first microfluidic pathway and the second microfluidic pathway is in turn merged with the third microfluidic pathway in the microfluidic droplet chip. This occurs at the second junction, which is downstream from the first junction. Any desired distance can be established between the first junction and second junction. In some embodiments, the first junction is also located within the microfluidic droplet chip. In some embodiments, the first junction is immediately upstream of the second junction, so that fluid in the combined pathway travels a negligible distance (for example, less than 10, 3, 1, 0.3, or 0.1 cm) before being combined with fluid from the third microfluidic pathway. This arrangement can reduce the mixing of components in the combined pathway. In some embodiments, the dimensions of the microfluidic pathways in the device, inside and/or outside the microfluidic droplet chip, are such that the movement of fluids is governed by laminar flow.

The third microfluidic pathway can be configured to deliver an oil/surfactant mixture to the microfluidic droplet chip. Thus, at the second junction in the device, aqueous and hydrophobic phases can mix and microfluidic droplets can form. The geometry of the second junction can be selected to ensure that these droplets have desired characteristics. For example, a geometry can be selected to facilitate the formation of monodisperse droplets, having desired sizes and spaced apart from each other by desired distances, at suitable flow rates in the microfluidic pathways. In some embodiments, the third microfluidic pathway is split into two subpathways upstream of the microfluidic droplet chip, which then merge together along with the combined (aqueous) pathway at the second junction. The two subpathways can approach each other at an large angle (for example, approximately or at least 30, 60, 90, 120, 150, or 180 degrees), so that the oil/surfactant mixture forms a sheath around the aqueous mixture as it enters the second junction. With this geometry, aqueous droplets are 'pinched off' from the aqueous mixture and flow in approximately the same direction as the aqueous mixture as they exit the junction. This approach to generating droplets is known in the art as flow focusing. In other embodiments, the combined aqueous pathway intersects the third microfluidic pathway at a right angle, thus giving the second junction a t-junction geometry. In these embodiments, an oil/surfactant mixture flows straight through the junction. The aqueous mixture approaches the junction in a direction perpendicular to that at which droplets formed from this mixture get carried away from the junction. The physics of droplet formation in various microfluidic geometries is described in Thorsen et al., *Phys. Rev. Lett.* 86, 4163-4166, 2001, and elsewhere.

The fluid pathway containing droplets, which results from the merger of the combined pathway containing an aqueous mixture and the third microfluidic pathway containing an oil/surfactant mixture, constitutes a sample pathway. The sample pathway is delivered to a sample collection container, which occurs downstream of the second junction. In the sample collection container, droplets can be subjected to thermal cycling. The droplets can also be broken open and barcoded nucleic acids can be harvested.

In operation, the device described herein can be used to encapsulate barcode adapter template beads and cells into aqueous microfluidic droplets, so that each droplet contains approximately one bead and one cell on average. The number of beads and cells in each droplet can be tuned as desired, for example by adjusting the concentrations of beads or cells in solutions loaded into the device, or by adjusting the flow rates in the three microfluidic pathways. The reagents included in each droplet allow barcode adapter molecules to be enzymatically generated from the one bead in the droplet. These reagents also allow the one cell to be lysed and RNAs from the cell to undergo barcoding reactions. Thus, the RNAs from the cell can be barcoded within the droplet, and nucleic acids derived from these RNAs (and containing a barcode sequence) can be later traced to one cell when the nucleic acids from multiple cells are mixed.

VII. EXAMPLES

A. Example 1

Making Barcode Adapter Template Bead Library in a Single Reaction

The method described below was used to create a barcode adapter template bead library using emulsion PCR, where polymerase chain reaction (PCR) was performed to attach unique barcode adapter templates to each bead (see FIG. 15).

TABLE 4

Oligos used to make barcode adapter template bead library in a single reaction

| Primer name | Sequence (SEQ ID NO:) |
|---|---|
| emB-T7bridge2 | dual-biotin-C18spacer-C18spacer-TAA TAC GAC TCA CTA TAG GAT AAA GCG GCC GCA AAT (1) |
| emB-BCbridge2 | mCmCC CCT GTT TAA ACC THH HTH HHH THH HHT HHH THH HHA TTT GCG GCC GCT TTA T (2) (random combination of HH HTH HHH THH HHT HHH THH HH (3), has $3^{18}$ or $387 \times 10^6$ possibilities, giving 387 million unique barcodes) |
| emB-T7bridgefree | TAA TAC GAC TCA CTA TAG GAT AAA GCG GCC GCA AAT (4) |
| emB-Rv3 | AlexaFluor647-C18spacer-mCmCC CCT GTT TAA ACC T (5) |

Streptavidin-coated M-270 Dynabeads® (Life Technologies) were coupled with biotinylated oligonucleotide ("emB_T7bridge2"):

1. Beads were resuspended by gently swirling
2. 1 mL of M270 beads (approx. $6.7 \times 10^8$ beads) were placed into each of three 1.5 mL microfuge tubes, for a total of 3 mL
3. Placed on magnet for 3 minutes.
4. Supernatant was removed from each tube and resuspended in 1 mL (1× vol) Bind/Wash Buffer (BWB; 1M NaCl, 5 mM Tris, 0.5 mM EDTA)
5. Step 4 was repeated twice more followed by final resuspension in 540 μL volume BWB
6. 60 μL of 100 μM emB_T7bridge2 was added to beads and incubated for 15 minutes with gentle rotation
7. Following incubation, beads were washed 3× with 1 mL BWB buffer, and combined into a single tube
8. Beads were stored at 4° C. with 0.01% sodium azide
9. Beads were washed 3× with 10 mM Tris before use Barcode oligonucleotides and forward and reverse primers were added to the coupled beads from above in an emulsion-based PCR:

1. The following PCR mix (3 mL total volume) was prepared in three 1.5 mL microcentrifuge tubes (VWR Cat. No. 20170-650):

| | |
|---|---|
| ddH₂O | 715.9 μL |
| 10X HiFi PCR buffer | 100 μL |
| 50 mM MgSO₄ | 50 μL |
| 10 mM dNTP mix | 20 μL |
| emB_T7bridge2-labeled Dynabeads (1.2 × 10⁷ beads/μL) | 50 μL |
| emB_T7bridgefree (10 μM) | 4 μL |
| emB_BCandbridge2 (1 pM) | 16.6 μL |
| emB_Rv3 (100 μM) | 30 μL |
| Thermostable inorganic pyrophosphatase (NEB 2,000 units/mL) | 1.5 μL |
| Platinum Taq Hifi (Life Technologies, 5 units/μL) | 12 μL |
| Total volume | 1000 μL |

2. An oil-surfactant mix was prepared (1 mL total volume):

| | | |
|---|---|---|
| a. | Mineral oil (Sigma) | 900 μL |
| b. | EM90 (Evonik) | 100 uL |

3. 800 μL of oil-surfactant mix and 200 μL of PCR mix were combined into each of 15 Axygen 2.0 mL Maxymum Recovery conical-bottom microcentrifuge tubes (MCT-200-L-C). Tubes were sealed and shaken for 3 seconds
4. Tubes were placed into a Qiagen TissueLyzer II, and shaken for 5 minutes at 14 Hz
5. The emulsion was divided among the wells of a VWR 96-well PCR plate (83007-374), with 160 μL of emulsion added per well
6. Tubes were thermocycled using the following program:

| Initial: | |
|---|---|
| 94° C. | 2' |
| 35 Cycles: | |
| 94° C. | 20" |
| 42° C. | 30" |
| 68° C. | 15" |
| 50 Cycles: | |
| 55° C. | 5.5' |
| 72° C. | 30" |
| Final extension: | |
| 68° C. | 5' |
| Hold: | |
| 10° C. | hold |

The emulsion was broken and beads were recovered:

1. The contents of the PCR plate was transferred into 1.5 mL microcentrifuge tubes (VWR 20170-650), with no more than 0.5 mL of emulsion volume per tube
2. 100 uL of 1 uM emB_T7bridgefree primer was added to each tube 3. Tubes were topped off with isobutanol, sealed and shaken to mix thoroughly
4. Tubes were centrifuged for 1 min at 14,000 rpm
5. Tubes were placed on a magnetic strip to draw the beads to the side of the tubes, then as much of the supernatant as possible was aspirated as possible while leaving the pelleted beads behind
6. 1 mL of isobutanol was added, mixed well by pipetting up and down until the remaining oil/emulsion volume had dispersed into the isobutanol
7. Tubes were placed on a magnetic strip to draw the beads to the side of the tubes, then the isobutanol was aspirated. Beads from all of the tubes were combined into a single tube by first aspirating the supernatant from the tube into which the beads will be combined and then transferring the full volume from another tube, allowing time for the beads to collect at the magnet, then aspirating the supernatant and repeating
8. 1 mL of fresh isobutanol was added, mixed well and let rest for 60 seconds
9. Isobutanol was aspirated
10. 1 mL of 100% ethanol was added, mixed well and let rest for 60 seconds
11. Ethanol was aspirated
12. Steps 10 and 11 were repeated
13. 1 mL of 70% ethanol was added, mixed well and let rest for 60 seconds
14. Ethanol was aspirated
15. Steps 13 and 14 were repeated
16. 1 mL PBS was added, mixed well and let rest for 60 seconds.
17. PBS was aspirated
18. Steps 16 and 17 were repeated Beads that incorporated barcode adapter templates were then sorted from non-barcoded beads using a Becton Dickenson FACS Aria III, utilizing the fluorescence from the Alexa Fluor 647 dye incorporated into the emB_Rv3 reverse primer.

Beads were stored in 0.01% sodium azide at 4° C. for storage.

Note that this example makes barcode adapter template beads with a T7 RNAP promoter sequence for amplification of barcode adapters by T7 RNAP. By replacing the T7 RNAP promoter sequence "TAA TAC GAC TCA CTA TAG G" (SEQ ID NO:6) in emB-T7bridge2 with other RNAP promoter sequences, barcode adapters can be amplified using other RNAPs. Also by replacing the promoter sequence with a nicking endonuclease site, such as Nt.BbvCI's "CCT CAG C", barcode adapters can be amplified using a nicking endonuclease (e.g. Nt.BbvCI) and a stranddisplacing DNAP such as Klenow exo-.

Also, "HH HTH HHH THH HHT HHH THH HH" (SEQ ID NO:3) in emB-BCbridge2 gives ~387 million unique barcodes. When this barcode library is used to barcode even, for example, 10 million cells, only 2.5% of the unique barcodes are used. It is expected that the majority of the barcodes are of sufficient distance from one another that the majority of barcode sequence reads from NextGen sequencing are easily distinguishable from one another (with a proportion of reads being discarded), regardless of PCR and sequencing errors.

The emulsion can be made using a variety of methods known to the field, and in this case was made using a shaking method and the resulting droplets were polydisperse with an average droplet diameter of ~25 µm. Barcode oligonucleotides were amplified with forward and reverse primers and the reverse primer was labeled with a fluorescent tag, which in this example was Alexa Fluor 647—so that beads that incorporated barcode adapter template were distinguishable from unlabeled beads. Bright fluorescent beads that incorporated barcode adapter template were then FACS sorted from dim unlabeled beads.

At the specified concentrations of beads and barcode oligonucleotide in this example, by Poisson distribution beads were loaded into droplets at an average of ~7 beads per droplet, and we observed that roughly 28% of droplets contained one or more copies of a unique barcode oligonucleotide, while the rest of the droplets contained no barcode oligonucleotide at all. Of the droplets that contained at least one barcode oligonucleotide, ~70% should contain exactly one barcode oligonucleotide while the remaining ~30% should contain two or more barcodes. Therefore ~70% of the barcode template adapter bead library was monoclonal (one unique barcode sequence per bead) and ~30% was polyclonal.

The end yield of the method described below was roughly 12 million barcode adapter template beads of which ~8.4 million are monoclonal barcode adapter template beads. And although droplets were filled with ~7 beads per droplet on average, after breaking the emulsion the yield of beads was ~2%. Based on a binomial distribution, ~7.7 million unique barcode sequences were present in this barcode adapter template bead library.

The concentrations of beads and barcode oligonucleotide can be adjusted to obtain a barcode adapter template bead library with differing proportions of monoclonal and polyclonal beads and a different number of unique barcode sequences present. This will allow for barcoding nucleic acids from single cells to achieve differing proportions of nucleic acids associated to a single cell via a unique barcode, or a set of unique barcodes, and also to change the percentage of barcoded nucleic acids discarded from further analysis.

This barcode adapter template bead making process can be optimized to achieve a ratio of monoclonal:polyclonal beads of, e.g., 90%:10%, 99%:1%, or any other ratio. This improvement over the current ~70%:30% ratio can be achieved by several different methods, including further diluting the oligo containing the barcode sequence (emB-BCbridge2 in this case) so that fewer copies are divided among the droplets in the emulsion, resulting in a reduced incidence of multiple barcode sequences being encapsulated in any given droplet.

B. Example 2

Making Barcode Adapter Template Bead Library in a Single Reaction II

The method described below was used to create a barcode adapter template bead library using emulsion PCR, where polymerase chain reaction (PCR) was performed to attach unique barcode adapter templates to each bead (see FIG. 15).

TABLE 5

Oligos used to make barcode adapter template bead library in a single reaction II

| Primer name | Sequence (SEQ ID NO:) |
|---|---|
| emB-T7bridgeIsceI | dual-biotin-C18spacer-C18spacer-TAA TAC GAC TCA CTA TAG GAT AGG GAT AAC AGG GTA ATA GGA (7) |
| emB_BCbridgeIScel_2 | mCmCC CCA GTT TAA ACT CCTH HHT HHH HTH HHH THH HTH HHH TCC TAT TAC CCT GTT ATC CC (8) (random combination of HH HTH HHH THH HHT HHH THH HH (3), has $3^{18}$ or 387 × $10^6$ possibilities, giving 387 million unique barcodes) |
| emB-T7bridgefreeIscel_2 | TAA TAC GAC TCA CTA TAG GAT AG GGATAACAGGGTAATAGGA (9) |
| emB_IsceI_RV | AlexaFluor647-C18spacer-mCmCC CCA GTT TAA ACT CCT (10) |

Streptavidin-coated M-270 Dynabeads® (Life Technologies) were coupled with biotinylated oligonucleotide ("emB_T7bridgeIsceI"):
1. Beads were resuspended by gently swirling
2. 1 mL of M270 beads (approx. $6.7 \times 10^8$ beads) were placed into each of three 1.5 mL microfuge tubes, for a total of 3 mL
3. Placed on magnet for 3 minutes.
4. Supernatant was removed from each tube and resuspended in 1 mL (1× vol) Bind/Wash Buffer (BWB; 1M NaCl, 5 mM Tris, 0.5 mM EDTA)
5. Step 4 was repeated twice more followed by final resuspension in 540 µL volume BWB
6. 60 µL of 100 µM emB_T7bridgeIsceI was added to beads and incubated for 15 minutes with gentle rotation
7. Following incubation, beads were washed 3× with 1 mL BWB buffer, and combined into a single tube
8. Beads were stored at 4° C. with 0.01% sodium azide
9. Beads were washed 3× with 10 mM Tris before use Barcode oligonucleotides and forward and reverse primers were added to the coupled beads from above in an emulsion-based PCR:
1. The following PCR mix (3 mL total volume) was prepared in three 1.5 mL microcentrifuge tubes (VWR Cat. No. 20170-650):

| | |
|---|---|
| ddH2O | 715.9 µL |
| 10X HiFi PCR buffer | 100 µL |
| 50 mM MgSO4 | 50 µL |
| 10 mM dNTP mix | 20 µL |
| emB_T7bridgeIsceI-labeled Dynabeads ($1.2 \times 10^7$ beads/µL) | 50 µL |
| emB_T7bridgefreeIscel_2 (10 µM) | 4 µL |
| emB_BCbridgeIScel_2 (1 pM) | 16.6 µL |
| emB_IsceI_RV (100 µM) | 30 µL |
| Thermostable inorganic pyrophosphatase (NEB 2,000 units/mL) | 1.5 µL |
| Platinum Taq Hifi (Life Technologies, 5 units/µL) | 12 µL |
| Total volume | 1000 µL |

2. An oil-surfactant mix was prepared (1 mL total volume):

| | | |
|---|---|---|
| a. | Mineral oil (Sigma) | 900 µL |
| b. | EM90 (Evonik) | 100 µL |

3. 800 µL of oil-surfactant mix and 200 µL of PCR mix were combined into each of 15 Axygen 2.0 mL Maxymum Recovery conical-bottom microcentrifuge tubes (MCT-200-L-C). Tubes were sealed and shaken for 3 seconds
4. Tubes were placed into a Qiagen TissueLyzer II, and shaken for 5 minutes at 14 Hz
5. The emulsion was divided among the wells of a VWR 96-well PCR plate (83007-374), with 160 µL of emulsion added per well
6. Tubes were thermocycled using the following program:

| Initial: | |
|---|---|
| 94° C. | 2' |
| 35 Cycles: | |
| 94° C. | 20" |
| 42° C. | 30" |
| 68° C. | 15" |
| 50 Cycles: | |
| 55° C. | 5.5' |
| 72° C. | 30" |
| Final extension: | |
| 68° C. | 5' |
| Hold: | |
| 10° C. | hold |

The emulsion was broken and beads were recovered:
1. The contents of the PCR plate was transferred into 1.5 mL microcentrifuge tubes (VWR 20170-650), with no more than 0.5 mL of emulsion volume per tube
2. 100 uL of 1 uM emB_T7bridgefreeIscel_2 primer was added to each tube
3. Tubes were topped off with isobutanol, sealed and shaken to mix thoroughly
4. Tubes were centrifuged for 1 min at 14,000 rpm
5. Tubes were placed on a magnetic strip to draw the beads to the side of the tubes, then as much of the supernatant as possible was aspirated as possible while leaving the pelleted beads behind
6. 1 mL of isobutanol was added, mixed well by pipetting up and down until the remaining oil/emulsion volume had dispersed into the isobutanol
7. Tubes were placed on a magnetic strip to draw the beads to the side of the tubes, then the isobutanol was aspirated. Beads from all of the tubes were combined into a single tube by first aspirating the supernatant from the tube into which the beads will be combined and then transferring the full volume from another tube, allowing time for the beads to collect at the magnet, then aspirating the supernatant and repeating
8. 1 mL of fresh isobutanol was added, mixed well and let rest for 60 seconds 9. Isobutanol was aspirated
10. 1 mL of 100% ethanol was added, mixed well and let rest for 60 seconds
11. Ethanol was aspirated
12. Steps 10 and 11 were repeated
13. 1 mL of 70% ethanol was added, mixed well and let rest for 60 seconds
14. Ethanol was aspirated
15. Steps 13 and 14 were repeated
16. 1 mL PBS was added, mixed well and let rest for 60 seconds.
17. PBS was aspirated
18. Steps 16 and 17 were repeated Beads that incorporated barcode adapter templates were then sorted from non-barcoded beads using a Becton Dickenson FACS Aria III, utilizing the fluorescence from the Alexa Fluor 647 dye incorporated into the emB_IsceI_RV reverse primer.

Beads were stored in 0.01% sodium azide at 4° C. for storage.

Note that this example makes barcode adapter template beads with a T7 RNAP promoter sequence for amplification of barcode adapters by T7 RNAP. By replacing the T7 RNAP promoter sequence "TAA TAC GAC TCA CTA TAG G" (SEQ ID NO:6) in emB-T7bridgeIsceI with other RNAP promoter sequences, barcode adapters can be amplified using other RNAPs. Also by replacing the promoter sequence with a nicking endonuclease site, such as Nt.BbvCI's "CCT CAG C", barcode adapters can be amplified using a nicking endonuclease (e.g. Nt.BbvCI) and a strand-displacing DNAP such as Klenow exo-.

Also, "HH HTH HHH THH HHT HHH THH HH" (SEQ ID NO:3) in emB-BCbridgeIsceI_2 gives ~387 million unique barcodes. When this barcode library is used to barcode even, for e.g., 10 million cells, only 2.5% of the unique barcodes are used. It is expected that the majority of the barcodes are of sufficient distance from one another that the majority of barcode sequence reads from NextGen sequencing are easily distinguishable from one another (with a proportion of reads being discarded), regardless of PCR and sequencing errors.

At the specified concentrations of beads and barcode oligonucleotide in this example, by Poisson distribution beads were loaded into droplets at an average of ~7 beads per droplet, and we observed that roughly 25% of droplets contained one or more copies of a unique barcode oligonucleotide, while the rest of the droplets contained no barcode oligonucleotide at all. Of the droplets that contained at least one barcode oligonucleotide, ~75% contained exactly one barcode oligonucleotide while the remaining ~25% contained two or more barcodes. Therefore ~75% of the barcode template adapter bead library was monoclonal (one unique barcode sequence per bead) and ~25% was polyclonal.

The end yield of the method described below was roughly 50 million barcode adapter template beads of which ~37.5 million were monoclonal beads. Although droplets were filled with ~7 beads per droplet on average, after breaking the emulsion the yield of beads was ~11%. Based on binomial distribution, ~28 million monoclonal beads with unique barcode sequences were present.

The concentrations of beads and barcode oligonucleotide can be adjusted to obtain a barcode adapter template bead library with differing proportions of monoclonal and polyclonal beads and a different number of unique barcode sequences present. This will allow for barcoding nucleic acids from single cells to achieve differing proportions of nucleic acids associated to a single cell via a unique barcode, or a set of unique barcodes, and also to change the percentage of barcoded nucleic acids discarded from further analysis.

C. Example 3

Making Barcode Adapter Template Bead Library in Multi-Steps

In this example reactions as per FIG. 16 were done, except that only one S1, one W, and one S2 barcode sequence used. Therefore, pooling of beads coupled to different S1 sequences did not occur, and similarly, beads were not pooled after the polymerase extension reaction to add W sequences to the S1 oligo.

This example can be easily extended to be done as per FIG. 16 simply by having multiple S1-oligo, W-oligo and S2-oligo with unique barcode sequences.

TABLE 6

Oligos used to make barcode adapter template bead library in a single reaction

| Primer name | Sequence (SEQ ID NO:) |
|---|---|
| S1-oligo | Desthiobiotin-C18spacer-ATA TTA ATA CGA CTC ACT ATA GGC ATA GGG ATA ACA GGG TAA TGA [S1] AG (11), where S1 = GATGGAT |
| W-oligo-a | CCT CCT CCT CCT CCC [W] CTI III III TCA TTA CCC TGT TAT CCC TAT GCC (12), where W = AGTGAGCTGCGT |
| W-oligo-b | CT CCT CCT CCC [W] CTI III III TCA TTA CCC TGT TAT CCC TAT GCC (13), where W = AGTGAGCTGCGT |
| S2-oligo-a | mCmCC CT [S2] TCC TCC TCC TCC TCC C (14), where S2 = CCTAACC |
| S2-oligo-b | mCmCC CT [S2] CTC CTC CTC CC (15), where S2 = CCTAACC |

Streptavidin-coated M-270 Dynabeads® (Life Technologies) were coupled with biotinylated oligonucleotides containing S1 sequence in individual reactions:
1. Beads were resuspended by gently swirling
2. M270 beads (Life Technologies) were placed on magnet for 3 minutes.
3. Supernatant was removed from each tube and resuspended in (1× vol) 0.5× Bind/Wash Buffer (BWB; 1M NaCl, 5 mM Tris, 0.5 mM EDTA)
4. Step 4 was repeated twice more followed by final resuspension in BWB buffer
5. 10 µM S1-oligo was added to beads and incubated for 15 minutes with gentle rotation 6. Following incubation, beads were washed 3× with BWB buffer
7. Beads were stored at 4° C. with 0.01% sodium azide
8. Beads were washed 3× with 10 mM Tris before use Coupled beads were then pooled together, and an extension reaction using w-oligo was performed.

For w extension reaction:

| | |
|---|---|
| ddH₂O | 26.1 μL |
| 10× Taq buffer | 5 μL |
| 100 mM MgCl₂ | 4.25 μL |
| 20% Tween 20 | 0.125 μL |
| 100× BSA | 5 μL |
| S1-coupled beads (1 mg in 20 μL) | 5 μL |
| dNTP | 1 μL |
| Taq (NEB) | 0.5 μL |
| TIPP (NEB) | 0.025 μL |
| 100 μM W-oligo-a OR W-oligo-b | 3 μL |

Incubated at 55° C. overnight in an shaking incubator, shaking at 800 rpm.

Beads were pooled and washed thrice with 1×BWB buffer. The anti-sense strand was then melted in 70° C. melt buffer (50 mM NaCl, 10 mM Tris pH 8.0). Beads were pelleted with a magnet and supernatant removed entirely, then beads are washed thrice in 1 mL TE0.1 and then resuspended in TE0.1 at 1 mg/20 uL.

For s2 extension reaction (per 250 μg beads):

| | |
|---|---|
| ddH₂O | 24.5 μL |
| 10× Taq buffer | 5 μL |
| 100 mM MgCl₂ | 4.25 μL |
| 20% Tween 20 | 0.125 μL |
| 100× BSA | 5 μL |
| S1 + w-a or S1 + w-b Beads | 5 μL |
| dNTP | 1 μL |
| 100 μM S2-oligo-a OR S2-oligo-b | 3 μL |

S2-oligo-a was used with S1+w-a beads, and S2-oligo-b was used with S1+w-b beads. Incubated at 60° C. for 10 min then slowly cooled to 37° C. Incubated at 37° C. for 2 hours, shaken at 800 rpm. Reaction was then allowed to cool to room temperature.
Then the following was added:

| | |
|---|---|
| dNTP (NEB) | 1 μL |
| *Ecoli* pyrophosphatase (NEB) | 0.1 μL |
| Klenow fragment (NEB) | 1 μL |

Reaction was incubated at 25° C. for 3 hours, shaking at 800 rpm. Every hour reaction was refreshed with 1 μL dNTP.

Beads were pooled and washed thrice with 1×BWB buffer. Beads were stored at 4° C. with 0.01% sodium azide and were washed 3× with 10 mM Tris before use.

A small aliquot of barcode adapter template beads were also used in an in vitro transcription reaction using T7 RNAP to determine if making of the beads was successful. If successful, T7 RNAP would be able to transcribe RNA off the double stranded T7 promoter present in the s1-oligo sequence. Megascript T7 kit (Life Technologies) was used and manufacturer's instructions were followed. 5 μL of reaction was run on an RNA Flashgel (Lonza). See FIG. 20.

The number of unique barcode sequences as formed from the combination of S1, W, and S2 sequences can be increased or decreased as desired. For example, as can be seen in Table 1, if the number of unique barcodes is ~10× greater than the number of cells to be barcoded, as determined by the binomial distribution, we can expect ~10% of cells to share identical barcodes and thus discarded during bioinformatic linking of nucleic acids to one another (this is detectable as more than one variable gene nucleic acid, such as two immunoglobulin heavy chains or two TCR alpha chains being associated with each other) Therefore, from such a library we can expect ~90% of barcoded cells to be successfully barcoded with a unique sequence enabling proper informatics linkage of nucleic acids to one another.

Therefore, the number of $S1_x$, W, and $S2_y$ sequences required is dependent on the desired number of cells to be barcoded. In Table 7, the W-extension reaction is envisioned to occur in 96-well plates, and an identical number of $S1_x$ and $S2_y$ sequences are used. As can be seen, to barcode 10 million cells, at most 323 $S1_x$ and $S2_y$ oligos and 960 $W_z$ oligos are required. These are manageable numbers, especially if the reactions are done in 96-well plates, necessitating a total of only 18 96-well plates to perform the reactions to make a barcode adapter template bead library of the desired size.

TABLE 7

Number of $S1_x$, $W_z$, and $S2_y$ sequences required to obtain a barcode adapter template library of sufficient size to barcode nucleic acids from a desired number of cells

| | # cells to be barcoded | | | | |
|---|---|---|---|---|---|
| | 1,000 | 10,000 | 100,000 | 1,000,000 | 10,000,000 |
| # unique beads required | 10,000 | 100,000 | 1,000,000 | 10,000,000 | 100,000,000 |
| # S1/S2 required if 96 w | 11 | 33 | 103 | 323 | 1021 |
| # S1/S2 required if 960 w | 4 | 11 | 33 | 103 | 323 |
| # S1/S2 required if 9600 w | 2 | 4 | 11 | 33 | 103 |

Also, it is desirable for the barcodes in $S1_x$, $S2_y$, and $W_z$ to be designed to be a minimum Hamming distance apart, with this minimum being 2. With this minimum, only barcode sequence reads from NextGen sequencing with an exact match to the barcode sequence are used; barcode sequence reads with errors are discarded. If the Hamming distance or edit distance used is increased to a minimum of 3, then error-correction is possible.

Note that this example makes barcode adapter template beads with a T7 RNAP promoter sequence for amplification of barcode adapters by T7 RNAP. By replacing the T7 RNAP promoter sequence "TAA TAC GAC TCA CTA TAG G" (SEQ ID NO:6) in emB-T7bridge2 with other RNAP promoter sequences, barcode adapters can be amplified using other RNAPs. Also by replacing the promoter sequence with a nicking endonuclease site, such as Nt.B-bvCI's "CCT CAG C", barcode adapters can be amplified using a nicking endonuclease (e.g. Nt.BbvCI) and a strand-displacing DNAP such as Klenow exo-.

D. Example 4

Making Aqueous Barcode Adapter Template

In this example, aqueous barcode adapter templates that were not coupled to beads were synthesized to demonstrate the broad applicability of the present methods.

A reaction mix was prepared as described below:

| | |
|---|---|
| ddH2O | 353 µL |
| 10x HiFi Buffer | 50 µL |
| 50 mM MgSO₄ | 20 µL |
| 10 mM dNTP mix | 10 µL |
| 10 µM emB_T7bridge2 (Refer to Table 4) | 25 µL |
| 1 pM emB_BCbridge2 (Refer to Table 4) | 13 µL |
| 10 µM emB_RV3 (Refer to Table 4) | 25 µL |
| Platinum Taq HiFi (Life Technologies) | 4 µL |
| Total Volume | 500 µL |

The reaction mix was then aliquoted into a 96-well PCR plate at 25 µL per well and thermocycled as follows:

| Initial: | |
|---|---|
| 95° C. | 1' |
| 22 Cycles: | |
| 95° C. | 20" |
| 46° C. | 30" |
| 68° C. | 30" |
| Final extension: | |
| 68° C. | 5' |
| Hold: | |
| 10° C. | hold |

The resulting PCR product, which is the barcode adapter template, was then blunted to remove A overhangs:

| | |
|---|---|
| NEBuffer 2 | 162 µL |
| 10 mM dNTPs | 30 µL |
| T4 DNA polymerase (New England Biolabs) | 2 µL |

2.5 µL of the blunting mix was added to each 25 µL reaction volume, and incubated at 12° C. for 15 minutes. 1 µL of 250 mM EDTA was then added to each 25 µL reaction volume and heated to 75° C. for 20 minutes to inactivate the enzyme.

The reaction was cleaned up and quantitated:
1. Reactions were then pooled and cleaned up using Zymo Research RNA Clean and Concentrator kit following manufacturer instructions
2. Picogreen quantitation kit (Life Technologies) was used to quantify the DNA and barcode adapter template concentration adjusted to 55 ng/uL Note that this example makes barcode adapter template beads with a T7 RNAP promoter sequence for amplification of barcode adapters by T7 RNAP. By replacing the T7 RNAP promoter sequence "TAA TAC GAC TCA CTA TAG G" (SEQ ID NO:6) in emB-T7bridge2 with other RNAP promoter sequences, barcode adapters can be amplified using other RNAPs. Also by replacing the promoter sequence with a nicking endonuclease site, such as Nt.B-bvCI's "CCT CAG C", barcode adapters can be amplified using a nicking endonuclease (e.g. Nt.BbvCI) and a strand-displacing DNAP such as Klenow exo-.

E. Example 5

Adding Barcodes from Barcode Adapter Templates to mRNA in Different Reaction Buffers This example shows that the present methods are useable in a variety of different buffers. Barcode adapter templates were made as described above in Example 4.

TABLE 8

| Composition of reaction buffers | |
|---|---|
| Buffer name | Composition |
| 1x MMLV | 50 mM Tris-HCl |
| | 75 mM KCl |
| | 3 mM MgCl2 |
| | 10 mM DTT |
| | pH 8.3 @ 25° C. |
| 1x Thermopol DF | 20 mM Tris-HCl |
| | 10 mM (NH4)2SO4 |
| | 10 mM KCl |
| | 2 mM MgSO4 |
| | pH 8.8@25° C. |
| 1x TAE | 40 mM Tris |
| | 20 mM acetic acid |
| | 1 mM EDTA |

The following reactions were set up:

| Using 0.5x MMLV buffer | |
|---|---|
| ddH2O | 4.8 µL |
| 10x MMLV buffer (NEB) | 1.25 µL |
| 100X BSA (NEB) | 1.25 µL |
| 100 mM MgCl2 | 1.75 µL |
| 50 µM oligo(dT)₂₀VN (SEQ ID NO: 16) | 0.5 µL |
| NTP mix (from Life Technologies Megascript SP6 kit) | 2 µL |
| dNTP (NEB) | 1.25 µL |
| barcode adapter template (55 ng/µL) | 0.6 µL |
| Ribolock (Thermo Scientific) | 0.6 µL |
| Total PBMC RNA (50 ng/ul) | 4 µL |

The above was heated to 55° C. for 3 minutes, then the following was added:

| | |
|---|---|
| Ribolock (Thermo Scientific) | 0.4 µL |
| E. coli inorganic pyrophosphatase (NEB) | 2 µL |
| T7 RNAP (NEB) | 1 µL |
| T4gp32 (NEB) | 0.6 µL |
| Maxima H- RTase (Thermo Scientific) | 3 µL |

T7 RNAP linear amplification of barcode adapters from barcode adapter template, reverse transcription and addition of barcodes to $1^{st}$ strand cDNA was performed at 42° C. for 2 hours.

| Using Thermopol buffer: | |
|---|---|
| ddH2O | 3.3 µL |
| 10x Thermopol DF (NEB) | 2.5 µL |
| 1M DTT | 0.25 µL |
| 100X BSA (NEB) | 1.25 µL |
| 100 mM MgCl2 | 1.75 µL |
| 50 µM oligo(dT)₂₀VN (SEQ ID NO: 16) | 0.5 µL |
| NTP mix (from Life Technologies Megascript SP6 kit) | 2 µL |
| dNTP (NEB) | 1.25 µL |
| barcode adapter template (55 ng/µL) | 0.6 µL |
| Ribolock (Thermo Scientific) | 0.6 µL |
| Total PBMC RNA (50 ng/µL) | 4 µL |

The above was heated to 55° C. for 3 minutes, then the following was added:

| | |
|---|---|
| Ribolock (Thermo Scientific) | 0.4 µL |
| E. coli inorganic pyrophosphatase (NEB) | 2 µL |
| T7 RNAP (NEB) | 1 µL |
| T4gp32 (NEB) | 0.6 µL |
| Maxima H- RTase (Thermo Scientific) | 3 µL |

T7 RNAP linear amplification of barcode adapters from barcode adapter template, reverse transcription and addition of barcodes to 1$^{st}$ strand cDNA was performed at 42° C. for 2 hours.

| USING TAE BUFFER: | |
|---|---|
| ddH2O | 4.55 μL |
| 5x TAE | 1.25 μL |
| 1M DTT | 0.25 μL |
| 100X BSA (NEB) | 1.25 μL |
| 100 mM MgCl2 | 1.75 μL |
| 50 nM oligo(dT)$_{20}$VN (SEQ ID NO: 16) | 0.5 μL |
| NTP mix (from Life Technologies Megascript SP6 kit) | 2 μL |
| dNTP (NEB) | 1.25 μL |
| barcode adapter template (55 ng/μL) | 0.6 μL |
| Ribolock (Thermo Scientific) | 0.6 μL |
| Total PBMC RNA (50 ng/μL) | 4 μL |

The above was heated to 55° C. for 3 minutes, then the following was added:

| Ribolock (Thermo Scientific) | 0.4 μL |
|---|---|
| E. coli inorganic pyrophosphatase (NEB) | 2 μL |
| T7 RNAP (NEB) | 1 μL |
| T4gp32 (NEB) | 0.6 μL |
| Maxima H- RTase (Thermo Scientific) | 3 μL |

T7 RNAP linear amplification of barcode adapters from barcode adapter template, reverse transcription, and addition of barcodes to 1$^{st}$ strand cDNA was performed at 42° C. for 2 hours.

The reaction was then cleaned up using a modified traditional phenol/chloroform method:

1. 200 μL of TE0.1 (10 mM Tris pH 8.0, 0.1 mM EDTA) was added to each reaction mix
2. 200 μL of Phenol/chloroform/isoamyl alcohol (Sigma) was added to each reaction mix and shaken vigorously in pre-spun Gel Phase Lock tubes (5Prime)
3. Gel Phase Lock tubes were centrifuged at 14,000 g for 3 minutes and the top aqueous fraction was pipetted into Amicon 100 kDa columns (Millipore) and spun at 14,000 g for 3 minutes
4. 450 μL TE (10 mM Tris, pH 8.0, 1 mM EDTA) was then pipetted into the Amicon column, and spun at 14,000 g for 3 minutes
5. 450 μL of 10 mM Tris (pH8.0) was then pipetted into the Amicon column and spun at 14,000 g for 5 minutes
6. The Amicon column was inverted into a new collection tube and spun at 1000 g for 2 minutes to collect the elute which contained the purified mRNA/1st strand cDNA duplex Two rounds of PCR (PCR1 and PCR2) were then performed:

TABLE 9

PCR1 and PCR2 primer sequences

| Primer name | Sequence (SEQ ID NO:) |
|---|---|
| L_GSP1 | TYT GTG GGA CTT CCA CTG CTC (17) |
| G_GSP1 | TCT TGT CCA CCT TGG TGT TGC TG (18) |
| K_GSP1 | CGA TTG GAG GGC GTT ATC CAC (19) |
| K_GSP2 | CTA TGC GCC TTG CCA GCC CGC TCA GTC AGA TGG CGG GAA GAT GAA GAC (20) |
| L_GSP2 | CTA TGC GCC TTG CCA GCC CGC TCA GGA GGA GGG YGG GAA CAG AGT GAC (21) |
| G_GSP2 | CTA TGC GCC TTG CCA GCC CGC TCA GGG GAA GTA GTC CTT GAC CAG GCA G (22) |
| BC_Long | GAG AGA CTG ACA GCG TAT CGC CTC CCT CGC GCC ATC AGA CGA GTG CGT GGA TAA AGC GGC CGC AAA T (23) |
| FW_1short | GAG AGA CTG ACA GCG TAT CGC CTC (24) |
| 2FR | CGT ATC GCC TCC CTC GCG (25) and CTA TGC GCC TTG CCA GCC C (26) mixed 1:1 |

The following PCR1 Phusion (Thermo Scientific) reaction mix was set up per RT reaction:

| H2O | 11.28 μL |
|---|---|
| 5x GC buffer | 5 μL |
| MgCl2 | 0.15 μL |
| DMSO | 1 μL |
| dNTP | 0.5 μL |
| 10 μM FW1-short | 1 μL |
| 10 μM BC-Long | 1 μL |
| 10 μM K-GSP1 | 0.56 μL |
| 10 μM L-GSP1 | 1.25 μL |
| 10 μM G-GSP1 | 0.56 μL |
| ET-SSB (NEB) | 0.25 μL |
| BSA | 0.25 μL |
| Phusion | 0.2 μL |
| cDNA template | 2 μL |

Initial:

| | |
|---|---|
| 95° C. | 5' |

18 Cycles:

| | |
|---|---|
| 98° C. | 30" |
| 62° C. | 30" |
| 72° C. | 45" |

Final extension:

| | |
|---|---|
| 72° C. | 5' |

Hold:

| | |
|---|---|
| 10° C. | hold |

The reactions from PCR1 were then diluted 50× and used as a template in 3 separate PCR2 reactions, one for kappa light chain, one for lambda light chain and one for gamma heavy chain.

The following PCR2 Phusion (Thermo Scientific) reaction mixes were set up per RT reaction:

| | |
|---|---|
| H2O | 17.82 µL |
| 5x GC buffer | 6 µL |
| MgCl2 | 0.18 µL |
| DMSO | 1 µL |
| dNTP | 0.6 µL |
| 10 µM 2FW | 1.2 µL |
| 10 µM K or L or G-GSP2 | 0.6 µL |
| BSA | 0.3 µL |
| Phusion | 0.3 µL |
| Dil. PCR1 template | 2 µL |

Initial:

| | |
|---|---|
| 95° C. | 5' |

28 cycles:

| | |
|---|---|
| 98° C. | 30" |
| 65° C. | 30" |
| 72° C. | 45" |

Final extension:

| | |
|---|---|
| 72° C. | 5' |

Hold:

| | |
|---|---|
| 10° C. | hold |

5 µL of product was run on a gel (FIG. 21). As can be seen, the barcoding reaction works well in a variety of different buffers that contain a variety of different ions such as potassium, ammonium, chloride, sulphate, and acetate ions.

F. Example 6

RNA Barcode Adapters Amplified from Barcode Adapter Templates Work Better than Unamplified DNA Barcode Adapters This example shows that the present methods are useable in a variety of different buffers with different salt concentrations. Also, using amplified RNA barcode adapters generated from barcode adapter templates works better (i.e., produces the desired amplified reaction product) than just adding DNA barcode adapters into the reaction, presumably because the reaction with RNA barcode adapters results in lower background (see FIG. 4). Barcode adapter templates were made as described above in Example 4.

TABLE 10

Additional oligo sequences

| Primer name | Sequence (SEQ ID NO:) |
|---|---|
| DNA barcode adapter w24 | TYT GTG GGA CTT CCA CTG CTC (17) |
| FW1_Long | GAG AGA CTG ACA GCG TAT CGC CTC CCT CGC GCC ATC AGA CGA GTG CGT CAC GAC CGG TGC TCG ATT TAG (27) |

The following reactions were set up and buffer compositions are as in Table 8:

| Using 1x MMLV buffer | |
|---|---|
| ddH$_2$O | 3.55 µL |
| 10x MMLV buffer (NEB) | 2.5 µL |
| 100X BSA (NEB) | 1.25 µL |
| 100 mM MgCl$_2$ | 1.75 µL |
| 50 µM oligo(dT)$_{20}$ VN (SEQ ID NO: 16) | 0.5 µL |
| NTP mix (from Life Technologies Megascript SP6 kit) | 2 µL |
| dNTP (NEB) | 1.25 µL |
| barcode adapter template (55 ng/µL) | 0.6 µL |
| Ribolock (Thermo Scientific) | 0.6 µL |
| Total PBMC RNA (50 ng/ul) | 4 µL |

The above was heated to 55° C. for 3 minutes, then the following was added:

| | |
|---|---|
| Ribolock (Thermo Scientific) | 0.4 µL |
| E. coli inorganic pyrophosphatase (NEB) | 2 µL |
| T7 RNAP (NEB) | 1 µL |
| T4gp32 (NEB) | 0.6 µL |
| Maxima H-RTase (Thermo Scientific) | 3 µL |

T7 RNAP linear amplification of barcode adapters from barcode adapter template, reverse transcription, and addition of barcodes to 1st strand cDNA was performed at 42° C. for 2 hours.

| Using 0.5x MMLV buffer | |
|---|---|
| ddH$_2$O | 4.8 µL |
| 10x MMLV buffer (NEB) | 1.25 µL |
| 100X BSA(NEB) | 1.25 µL |
| 100 mM MgCl$_2$ | 1.75 µL |
| 50 µM oligo(dT)$_{20}$ VN (SEQ ID NO: 16) | 0.5 µL |
| NTP mix (from Life Technologies Megascript SP6 kit) | 2 µL |
| dNTP (NEB) | 1.25 µL |
| barcode adapter template (55 ng/µL) | 0.6 µL |
| Ribolock (Thermo Scientific) | 0.6 µL |
| Total PBMC RNA (50 ng/ul) | 4 µL |

The above was heated to 55° C. for 3 minutes, then the following was added:

| | |
|---|---|
| Ribolock (Thermo Scientific) | 0.4 µL |
| E. coli inorganic pyrophosphatase (NEB) | 2 µL |
| T7 RNAP (NEB) | 1 µL |
| T4gp32 (NEB) | 0.6 µL |
| Maxima H-RTase (Thermo Scientific) | 3 µL |

T7 RNAP linear amplification of barcode adapters from barcode adapter template, reverse transcription, and addition of barcodes to 1st strand cDNA was performed at 42° C. for 2 hours.

| Using DNA barcode adapter | |
|---|---|
| ddH₂O | 13 µL |
| 10x MMLV buffer (NEB) | 2.5 µL |
| 100X BSA (NEB) | 0.25 µL |
| 100 mM MgCl₂ | 0.75 µL |
| 50 µM oligo(dT)₂₀ VN (SEQ ID NO: 16) | 1 µL |
| 10 µM DNA barcode adapter w24 | 2.5 µL |
| Ribolock (Thermo Scientific) | 0.6 |
| Total PBMC RNA (50 ng/ul) | 2 µL |

The above was heated to 55° C. for 3 minutes, then the following was added:

| Ribolock (Thermo Scientific) | 0.4 µL |
|---|---|
| T4gp32 (NEB) | 1 µL |
| Maxima H-RTase (Thermo Scientific) | 1 µL |

Reverse transcription and addition of barcodes to 1st strand cDNA was performed at 42° C. for 2 hours.

The reaction was then cleaned up using a modified traditional phenol/chloroform method:

1. 200 µL of TE0.1 (10 mM Tris pH 8.0, 0.1 mM EDTA) was added to each reaction mix
2. 200 µL of Phenol/chloroform/isoamyl alcohol (Sigma) was added to each reaction mix and shaken vigorously in pre-spun Gel Phase Lock tubes (5Prime)
3. Gel Phase Lock tubes were centrifuged at 14,000 g for 3 minutes and the top aqueous fraction was pipetted into Amicon 100 kDa columns (Millipore) and spun at 14,000 g for 3 minutes
4. 450 µL TE (10 mM Tris, pH 8.0, 1 mM EDTA) was then pipetted into the Amicon column, and spun at 14,000 g for 3 minutes
5. 450 µL of 10 mM Tris (pH8.0) was then pipetted into the Amicon column and spun at 14,000 g for 5 minutes
6. The Amicon column was inverted into a new collection tube and spun at 1000 g for 2 minutes to collect the elute which contained the purified mRNA/1ˢᵗ strand cDNA duplex Two rounds of PCR (PCR1 and PCR2) were then performed:

The following PCR1 Phusion (Thermo Scientific) reaction mix was set up per RT reaction that used a barcode adapter template:

| H₂O | 11.28 µL |
|---|---|
| 5x GC buffer | 5 µL |
| MgCl₂ | 0.15 µL |
| DMSO | 1 µL |
| dNTP | 0.5 µL |
| 10 µM FW1-short | 1 µL |
| 10 µM BC-Long | 1 µL |
| 10 µM K-GSP1 | 0.56 µL |
| 10 µM L-GSP1 | 1.25 µL |
| 10 µM G-GSP1 | 0.56 µL |
| ET-SSB (NEB) | 0.25 µL |
| BSA | 0.25 µL |
| Phusion | 0.2 µL |
| cDNA template | 2 µL |

The following PCR1 Phusion (Thermo Scientific) reaction mix was set up per RT reaction that used a DNA barcode adapter:

| H₂O | 11.28 µL |
|---|---|
| 5x GC buffer | 5 µL |
| MgCl₂ | 0.15 µL |
| DMSO | 1 µL |
| dNTP | 0.5 µL |
| 10 µM FW1-short | 1 µL |
| 10 µM FW-Long | 1 µL |
| 10 µM K-GSP1 | 0.56 µL |
| 10 µM L-GSP1 | 1.25 µL |
| 10 µM G-GSP1 | 0.56 µL |
| ET-SSB (NEB) | 0.25 µL |
| BSA | 0.25 µL |
| Phusion | 0.2 µL |
| cDNA template | 2 µL |

| Initial: | |
|---|---|
| 95° C. | 5' |
| 18 Cycles: | |
| 98° C. | 30" |
| 62° C. | 30" |
| 72° C. | 45" |
| Final extension: | |
| 72° C. | 5' |
| Hold: | |
| 10° C. | hold |

The reactions from PCR1 were then diluted 50x and used as a template in 3 separate PCR2 reactions, one for kappa light chain, one for lambda light chain, and one for gamma heavy chain.

The following PCR2 Phusion (Thermo Scientific) reaction mixes were set up per PCR1 reaction:

| H₂O | 17.82 µL |
|---|---|
| 5x GC buffer | 6 µL |
| MgCl₂ | 0.18 µL |
| DMSO | 1 µL |
| dNTP | 0.6 µL |
| 10 µM 2FW | 1.2 µL |
| 10 µM K or L or G-GSP2 | 0.6 µL |
| BSA | 0.3 µL |
| Phusion | 0.3 µL |
| Dil. PCR1 template | 2 µL |

| Initial: | |
|---|---|
| 95° C. | 5' |
| 28 cycles: | |
| 98° C. | 30" |
| 65° C. | 30" |
| 72° C. | 45" |
| Final extension: | |
| 72° C. | 5" |
| Hold: | |
| 10° C. | hold |

5 µL of product was run on a gel (FIG. 22). As can be seen, the barcoding reaction works well in buffers with differing salt concentrations. While the reaction works better in a low salt buffer (0.5xMMLV) due to the salt sensitivity of the T7 RNAP, it also works in a higher salt buffer (1xMMLV). Note that due to non-specific priming during the RT step when using DNA barcode adapters (refer to FIG. 4), there was exceptionally high background and the desired bands were obscured.

G. Example 7

Barcoding Nucleic Acids from Cells Using Aqueous Barcode Adapter Templates in Droplets Made Using a Microfluidic Droplet Device A device for creating monodisperse emulsions was used to encapsulate single cells along with barcoded beads and other reagents necessary for the barcoding assay. Three Dolomite P-Pumps were equipped with flow sensors (Dolomite 3200016, 3200095, and 3200098). The first P-Pump was connected directly to a 2-Reagent Droplet Chip (Dolomite 3200287) via microfluidic tubing that incorporated a T-junction to split the line into two inputs. This was the oil input line. The other two P-Pumps were connected via fluidic tubing to PEEK sample loops that coiled around an ice bin that served to keep samples chilled while the device was operating, and each of these loops were connected to the 2-Reagent Droplet Chip. Each sample loop incorporated a four-way valve at its front end so that sample could be loaded into the loop by means of a syringe. The first sample loop was filled with cells while the second loop was filled with RT/barcoding/lysis mix. An example of the device configuration is as shown in FIGS. 17-19. The ice bin was filled with ice prior to use.

A murine B220+ B cell population was FACS sorted and a cell suspension was prepared using 300 mM betaine with 10 mM NaCl and 0.5 mg/ml BSA as a suspension buffer. Cells were used at a concentration of 4,500 cells/µL. An RT/aqueous barcode mix was prepared as follows:

| | |
|---|---|
| 10X Thermopol DF | 30 µL |
| 1M DTT | 3 µL |
| 1M MgCl$_2$ | 3.6 µL |
| 50 µM oligo(dT)$_{20}$ VN (SEQ ID NO: 16) | 6 µL |
| NTP mix (from Life Technologies Megascript SP6 kit) | 48 µL |
| dNTP (NEB) | 15 µL |
| barcode adapter template (55 ng/µL) | 7.2 µL |
| 10% Tween-20 | 1 µL |
| Ribolock (Thermo Scientific) | 12 µL |
| E. coli inorganic pyrophosphatase (NEB) | 24 µL |
| T7 RNAP (NEB) | 12 µL |

-continued

| | |
|---|---|
| T4gp32 (NEB) | 7.2 µL |
| Maxima H-RTase (Thermo Scientific) | 36 µL |
| Total volume | 205 µL |

The cell suspension was loaded into one sample loop and the RT/barcoding/lysis mix was loaded into the other sample loop using syringes. Cell and barcode concentrations were chosen in such a way as to minimize the occurrence of multiple cells or barcodes in a single droplet, while keeping those concentrations high enough so that a large enough number of cells were encapsulated with barcodes. The 4-way valves were switched so that the sample loops were in line with the pump, and all three pumps were activated. The two aqueous inputs were flowed at rates so that they mixed at a 1:2 (cell suspension:RT/barcoding/lysis mix) ratio. The aqueous and oil inputs were flowed at rates so that droplets that were ~50 µm in diameter are formed, and at a high enough flow rate so that cells flowed through the device. The emulsion was collected in a Sorenson Bioscience 0.2 mL PCR tube. After the sample had been created, it was first given a pre-heat step (3 minutes at 55° C.) and then incubated for 2 hours at 42° C. to allow the reaction to proceed. Following the reaction, the emulsion was broken using the "breaking non-bead emulsion" process described below. This produced a purified sample of cDNA for subsequent PCR amplification and sequencing.

Non-bead emulsions were broken as follows:
1. 200 µL TE, 400 µL phenol/chloroform/isoamyl alcohol, 800 µL chloroform were pipetted into pre-spun Gel Phase Lock tubes
2. Each sample was pipetted into a corresponding Gel Phase Lock tube
3. Tubes were spun down for 3 minutes at 14,000 g
4. The aqueous layers were pipetted into 100 kDa Amicon tubes (Millipore).
5. Tubes were spun down for 3 minutes at 14,000 g
6. 450 µL of TE was pipetted into the Amicon tubes
7. Tubes were spun down for 3 minutes at 14,000 g
8. 450 µL of 10 mM Tris was added to the Amicon tubes
9. Tubes were spun down for 5 minutes at 14,000 g
10. Amicon tubes were placed inverted into fresh collection tubes
11. Tubes were spun down for 2 minutes at 1,000 g Two rounds of PCR (PCR1 and PCR2) were then performed, using the following primers in addition to some primer sequences listed in Table 9.

TABLE 11

Additional primers for PCR of murine immunoglobulin genes

| Primer name | Sequence (SEQ ID NO:) |
|---|---|
| L_GSP1_murine | ACT CTT CTC CAC AGT GTC CCC TTC ATG (28) and<br>ACT CTT CTC CAC AGT GTG ACC TTC ATG (29) mixed 50:50 |
| G_GSP1_murine | CTG GAC AGG GAT CCA GAG TTC C (30) and<br>CTG GAC AGG GCT CCA TAG TTC C (31) mixed 50:50 |
| K_GSP1_murine | CCA TTT TGT CGT TCA CTG CCA TC (32) |
| M_GSP1_murine | CCA GAG AAG CCA TCC CGT GGT (33) |
| K_GSP2_murine | CTA TGC GCC TTG CCA GCC CGC TCA GCA CTG GAT GGT GGG AAG ATG GA (34) |
| L_GSP2_murine | CTA TGC GCC TTG CCA GCC CGC TCA GGG CCT TGT AGT CT CGA GCT CTT C (35) and |

TABLE 11-continued

Additional primers for PCR of murine immunoglobulin genes

| Primer name | Sequence (SEQ ID NO:) |
|---|---|
| | CTA TGC GCC TTG CCA GCC CGC TCA GGG CTT TGT TTT CCT KGA GCT CCT C (36) mixed 50:50 |
| G_GSP2_murine | CTA TGC GCC TTG CCA GCC CGC TCA GGG GGC CAG TGG ATA GAC HGA TG (37) and CTA TGC GCC TTG CCA GCC CGC TCA GCA GGG ACC AAG GGA TAG ACA GAT G (38) mixed 50:50 |
| M_GSP2 murine | CTA TGC GCC TTG CCA GCC CGC TCA GGR AAG ACA TTT GGG RAG GAC TGA CTC (39) |

The following PCR1 Phusion (Thermo Scientific) reaction mix was set up per RT reaction that used a barcode adapter template:

| | |
|---|---|
| H$_2$O | 10.53 μL |
| 5x GC buffer | 5 μL |
| MgCl$_2$ | 0.15 μL |
| DMSO | 1 μL |
| dNTP | 0.5 μL |
| 10 μM FW1-short | 1 μL |
| 10 μM BC-Long | 1 μL |
| 10 μM mK-GSP1 | 0.5 μL |
| 10 μM mL-GSP1 | 0.5 μL |
| 10 μM mG-GSP1 | 0.56 μL |
| 10 μM mM-GSP1 | 0.56 μL |
| ET-SSB (NEB) | 0.25 μL |
| BSA | 0.25 μL |
| Phusion | 0.2 μL |
| cDNA template | 2 μL |

| Initial: | |
|---|---|
| 95° C. | 5' |
| 18 Cycles: | |
| 98° C. | 30" |
| 62° C. | 30" |
| 72° C. | 45" |
| Final extension: | |
| 72° C. | 5' |
| Hold: | |
| 10° C. | hold |

The reactions from PCR1 were then diluted 50× and used as a template in 3 separate PCR2 reactions, one for kappa and lambda light chains, one for mu heavy chain, and one for gamma heavy chain.

The following PCR2 Phusion (Thermo Scientific) reaction mixes were set up per PCR1 reaction:

| | |
|---|---|
| H$_2$O | to 30 μL |
| 5x GC buffer | 6 μL |
| MgCl$_2$ | 0.18 μL |
| DMSO | 1 μL |
| dNTP | 0.6 μL |
| 10 μM 2FW | 1.2 μL |
| 10 μM mK and mL or mM-GSP2 | 0.6 μL |
| BSA | 0.3 μL |
| Phusion | 0.3 μL |
| Dil. PCR1 template | 2 μL |

| Initial: | |
|---|---|
| 95° C. | 5' |
| 28 cycles: | |
| 98° C. | 30" |
| 65° C. | 30" |
| 72° C. | 45" |
| Final extension: | |
| 72° C. | 5' |
| Hold: | |
| 10° C. | hold |

5 μL of PCR product was run on a gel (FIG. 23). Bands corresponding to kappa and lambda light chain, and to mu heavy chain were clearly seen. Only the mu heavy chain was amplified as the majority of B220+ B cells were expected to be naïve B cells which are IgM+.

The immunoglobulin heavy and light chains thus amplified can be purified and prepared for next generation sequencing, such as, but not limited to, 454 sequencing. As this example used barcode adapter templates at concentrations of >1 copy per reaction container, a unique set of barcodes are incorporated into the nucleic acids in each reaction container rather than a unique barcode. Paired immunoglobulin heavy and light chains can be associated with each other by them sharing a unique set of barcodes, rather than by a unique barcode.

Barcode adapter templates can also be used at a concentration such that by limiting dilution the majority of reaction containers that contain a barcode adapter template will contain it at 1 copy per reaction container. In this case, paired immunoglobulin heavy and light chains can be associated with each other by them sharing a unique barcode sequence.

H. Example 8

Barcoding Nucleic Acids from Cells Using Barcode Adapter Template Beads in Droplets Made Using a Microfluidic Droplet Device This example describes an embodiment of the invention based on predicted results rather than results actually achieved. A microfluidic device to generate droplets as described in Example 7 is used, with the only difference being that the first sample loop contained both cells and barcode adapter template beads as made in Examples 1, 2 or 3.

A murine B220+ B cell population is FACS sorted and a cell and barcode adapter template bead suspension is prepared using 300 mM betaine with 10 mM NaCl and 0.5 mg/ml BSA as a suspension buffer. Cells are included at a concentration of 4,500 cells/µL and beads are used at a concentration of 60,000 beads/µL.

An RT mix is prepared as follows:

| | |
|---|---|
| ddH$_2$O | 7.4 µL |
| 10X Thermopol DF | 36 µL |
| 1M DTT | 3.6 µL |
| 1M MgCl$_2$ | 4.3 µL |
| 50 µM oligo(dT) | 7.2 µL |
| NTP mix (from Life Technologies Megascript SP6 kit) | 57.6 µL |
| dNTP (NEB) | 18 µL |
| 10% Tween-20 | 1.2 µL |
| Ribolock (Thermo Scientific) | 14.4 µL |
| E. coli inorganic pyrophosphatase (NEB) | 28.8 µL |
| T7 RNAP (NEB) | 14.4 µL |
| T4gp32 (NEB) | 8.6 µL |
| Maxima H- RTase (Thermo Scientific) | 43.2 µL |
| Total volume | 244.8 µL |

The cell and barcoded bead suspension is loaded into one sample loop and the RT/barcoding/lysis mix is loaded into the other sample loop using syringes. The 4-way valves are switched so that the sample loops are in line with the pump, and all three pumps are activated. The two aqueous inputs are flowed at rates so that they mix at a 1:2 (cell and bead suspension:RT/barcoding/lysis mix) ratio. The aqueous and oil inputs are flowed at rates so that droplets that are ~50 um in diameter are formed, and at a high enough flow rate so that cells and beads flow through the device. The emulsion is collected in a Sorenson Bioscience 0.2 mL PCR tube. After the sample has been created, it is first given a heat step (3 minutes at 55° C.) and then incubated for 2 hours at 42° C. to allow the RT/barcoding reaction to proceed. Following the barcoding reaction, the emulsion is broken using the "breaking non-bead emulsion" process described in Example 7. Subsequent PCR reactions are performed as in Example 7.

The immunoglobulin heavy and light chains thus amplified are purified and prepared for next generation sequencing, such as, but not limited to, 454 sequencing. As this example uses barcode adapter templates beads at ~1 bead per reaction container, paired immunoglobulin heavy and light chains are paired by their shared use of a unique barcode sequence.

I. Example 9

Barcoding Nucleic Acids from Cells Using Barcode Adapters Amplified from Barcode Adapter Templates Beads with a DNA Polymerase This example describes an embodiment of the invention based on predicted results rather than results actually achieved. A microfluidic device to generate droplets as described in Example 7 is used, with the only difference being that the first sample loop contained both cells and barcode adapter template beads as made in Examples 1, 2 or 3. In this example, the barcode adapter template beads comprise a 5' Nt.BbvCI nicking endonuclease sequence rather than a T7 RNAP promoter sequence to allow for amplification of barcode adapters by a DNA polymerase.

A murine B220+ B cell population was FACS sorted and a cell and barcode adapter template bead suspension was prepared using 300 mM betaine with 10 mM NaCl and 0.5 mg/ml BSA as a suspension buffer. Cells are included at a concentration of 4,500 cells/uL and beads are used at a concentration of 60,000 beads/µL.

An RT mix is prepared as follows:

| | |
|---|---|
| ddH$_2$O | 32.7 µL |
| 10X Thermopol DF | 36 µL |
| 1M DTT | 3.6 µL |
| 1M MgCl$_2$ | 4.3 µL |
| 50 µM oligo(dT) | 7.2 µL |
| dNTP (NEB) | 36 µL |
| 10% Tween-20 | 1.2 µL |
| Ribolock (Thermo Scientific) | 14.4 µL |
| E. coli inorganic pyrophosphatase (NEB) | 28.8 µL |
| Nt.BbvCI (NEB) | 14.4 µL |
| Klenow exo- (NEB) | 14.4 µL |
| T4gp32 (NEB) | 8.6 µL |
| Maxima H- RTase (Thermo Scientific) | 43.2 µL |
| Total volume | 244.8 µL |

The cell and barcoded bead suspension is loaded into one sample loop and the RT/barcoding/lysis mix is loaded into the other sample loop using syringes. The 4-way valves are switched so that the sample loops are in line with the pump, and all three pumps are activated. The two aqueous inputs are flowed at rates so that they mix at a 1:2 (cell and bead suspension:RT/barcoding/lysis mix) ratio. The aqueous and oil inputs are flowed at rates so that droplets that are ~50 um in diameter are formed, and at a high enough flow rate so that cells and beads flow through the device. The emulsion is collected in a Sorenson Bioscience 0.2 mL PCR tube. After the sample has been created, it is first given a heat step (3 minutes at 55° C.) and then incubated for 2 hours at 42° C. to allow the RT/barcoding reaction to proceed. Following the barcoding reaction, the emulsion is broken using the "breaking non-bead emulsion" process described in Example 7. Subsequent PCR reactions are performed as in Example 7.

The immunoglobulin heavy and light chains thus amplified are purified and prepared for next generation sequencing, such as, but not limited to, 454 sequencing. As this example uses barcode adapter templates beads at ~1 bead per reaction container, paired immunoglobulin heavy and light chains are paired by their shared use of a unique barcode sequence.

J. Example 10

Barcoding Nucleic Acids from Cells Using Barcode Adapter Templates in Multi-Well Reaction Containers This example describes an embodiment of the invention based on predicted results rather than results actually achieved. Barcode adapter templates with a composition as in FIG. 1 are synthesized as duplex oligos from a vendor such as IDT. Each unique barcode adapter template is kept in a different storage container such that there is no mixing or cross-contamination of barcode sequences. Activated B cells (plasmablasts) are single cell sorted using a FACS Aria II (Becton Dickenson) into 10 µL of a lysis buffer into all wells of a 96-well plate. The composition of the buffer in each well is:

| | |
|---|---|
| 10 mM Tris pH 8.0 | to 10 µL |
| 10x MMLV buffer | 1 µL |
| 100 mM MgCl$_2$ | 0.3 µL |

| | |
|---|---|
| 1M DTT | 0.015 μL |
| 100x BSA (NEB) | 0.075 μL |
| dNTP | 0.5 μL |
| 10 μM oligo(dT)$_{25}$ (SEQ ID NO: 40) | 0.5 μL |
| 20% IGEPAL-630 (Sigma) | 0.15 μL |
| 1 μM barcode adapter template | 0.25 μL |
| Ribolock (Thermo Scientific) | 0.4 μL |
| Maxima H- RTase (Thermo Scientific) | 0.25 μL |

The plate is then incubated at 55° C. for 3 minutes, then incubated at 42° C. for 2 hours for the RT/barcoding reaction to occur. The reactions in all wells of a 96-well plate were then pooled together and cleanup is performed using a modified traditional phenol/chloroform method:

1. 400 μL of Phenol/chloroform/isoamyl alcohol (Sigma) is added to and shaken vigorously in pre-spun Gel Phase Lock tubes (5Prime)
2. Gel Phase Lock tubes are centrifuged at 14,000 g for 3 minutes and the top aqueous fraction is pipetted into Amicon 100 kDa columns (Millipore) and spun at 14,000 g for 3 minutes
3. Step 2 is repeated as necessary to get the entire aqueous volume spun through the Amicon column
4. 450 μL TE (10 mM Tris, pH 8.0, 1 mM EDTA) is then pipetted into the Amicon column, and spun at 14,000 g for 3 minutes
5. 450 μL of 10 mM Tris (pH8.0) is then pipetted into the Amicon column and spun at 14,000 g for 5 minutes
6. The Amicon column is inverted into a new collection tube and spun at 1000 g for 2 minutes to collect the elute which contained the purified mRNA/1$^{st}$ strand cDNA duplex The following PCR1 Phusion (Thermo Scientific) reaction mix is set up:

| | |
|---|---|
| H2O | 11.28 μL |
| 5x GC buffer | 5 μL |
| MgCl$_2$ | 0.15 μL |
| DMSO | 1 μL |
| dNTP | 0.5 μL |
| 10 μM FW1-short | 1 μL |
| 10 μM FW-Long | 1 μL |
| 10 μM K-GSP1 | 0.56 μL |
| 10 μM L-GSP1 | 1.25 μL |
| 10 μM G-GSP1 | 0.56 μL |
| ET-SSB (NEB) | 0.25 μL |
| BSA | 0.25 μL |
| Phusion | 0.2 μL |
| cDNA template | 2 μL |

| Initial: | |
|---|---|
| 95° C. | 5' |
| 18 Cycles: | |
| 98° C. | 30" |
| 62° C. | 30" |
| 72° C. | 45" |

| Final extension: | |
|---|---|
| 72° C. | 5' |
| Hold: | |
| 10° C. | hold |

The reaction from PCR1 is then diluted 50× and used as a template in 3 separate PCR2 reactions, one for kappa light chain, one for lambda light chain and one for gamma heavy chain.

The following PCR2 Phusion (Thermo Scientific) reaction mixes are set up:

| | |
|---|---|
| H2O | 17.82 μL |
| 5x GC buffer | 6 μL |
| MgCl$_2$ | 0.18 μL |
| DMSO | 1 μL |
| dNTP | 0.6 μL |
| 10 μM 2FW | 1.2 μL |
| 10 μM K or L or G-GSP2 | 0.6 μL |
| BSA | 0.3 μL |
| Phusion | 0.3 μL |
| Dil. PCR1 template | 2 μL |

| Initial: | |
|---|---|
| 95° C. | 5' |
| 23 or 28 cycles: | |
| 98° C. | 30" |
| 65° C. | 30" |
| 72° C. | 45" |
| Final extension: | |
| 72° C. | 5' |
| Hold: | |
| 10° C. | hold |

The immunoglobulin heavy and light chains thus amplified are purified and prepared for next generation sequencing, such as, but not limited to, 454 sequencing. As this example uses a unique barcode adapter templates individually pipetted into each reaction container (in this case wells of a 96-well plate), paired immunoglobulin heavy and light chains are bioinformatically paired by their shared use of a unique barcode sequence.

K. Example 11

Barcoding Nucleic Acids from Cells Using Barcode Adapter Template Beads in Droplets Made Using a Microfluidic Droplet Device The method described below was used to create a barcode adapter template bead library using emulsion PCR, where polymerase chain reaction (PCR) was performed to attach unique barcode adapter templates to each bead (see FIG. 15).

TABLE 12

Oligos used to make barcode adapter template bead library in a single reaction

| Primer name | Sequence (SEQ ID NO:) |
|---|---|
| emB-T7bridgeIsceI | dual-biotin-C18spacer-C18spacer- TAA TAC GAC TCA CTA TAG GAT AGG GAT AAC AGG GTA ATA GGA (7) |
| emB-BCbridgeIsceI2 | mCmCC CCA GTT TAA ACT CCTH HHT HHH HTH HHH THH HTH HHH TCC TAT TAC CCT GTT ATC CC (8) (random combination of HH HTH HHH THH HHT HHH THH HH (3), has $3^{18}$ or 387 × $10^6$ possibilities, giving 387 million unique barcodes) |
| emB-T7bridgefreeIsceI_2 | TAA TAC GAC TCA CTA TAG GAT AGG GAT AAC AGG GTA ATA GGA (9) |
| emB_Iscel_RV | AlexaFluor647-C18spacer-mCmCC CCA GTT TAA ACT CCT (10) |

Streptavidin-coated M-270 Dynabeads® (Life Technologies) were coupled with biotinylated oligonucleotide ("emB_T7bridgeIsceI"):
1. Beads were resuspended by gently swirling
2. 1 ml of M270 beads (approx. 2×$10^9$ beads) were placed into each of three 1.5 mL microfuge tubes, for a total of 3 mL
3. Placed on magnet for 3 minutes.
4. Supernatant was removed from each tube and resuspended in 1 mL (1× vol) Bind/Wash Buffer (BWB; 1M NaCl, 5 mM Tris, 0.5 mM EDTA)
5. Step 4 was repeated twice more followed by final resuspension in 540 µL volume BWB
6. 60 µL of 100 µM emB_T7bridge2 was added to beads and incubated for 15 minutes with gentle rotation
7. Following incubation, beads were washed 3× with 1 mL BWB buffer, and combined into a single tube
8. Beads were stored at 4° C. with 0.01% sodium azide
9. Beads were washed 3× with 10 mM Tris before use Added barcode oligonucleotides and forward and reverse primers to the coupled beads from above in an emulsion-based PCR:
1. The following PCR mix (3 mL total volume) was prepared in three 1.5 mL microcentrifuge tubes (VWR Cat. No. 20170-650):

| | |
|---|---|
| ddH$_2$O | 572.7 µL |
| 10X HiFi PCR buffer | 80 µL |
| 50 mM MgSO$_4$ | 40 µL |
| 10 mM dNTP mix | 16 µL |
| emB_T7bridgeIsceI-labeled Dynabeads (2 × $10^5$ beads/µL) | 40 µL |
| emB_T7bridgefreeIsceI_2 (10 µM) | 3.2 µL |
| emB_BCbridgeIsceI_2 (1 pM) | 13.3 µL |
| emB_IsceI_RV (100 µM) | 24 µL |
| Thermostable inorganic pyrophosphatase (NEB 2,000 units/mL) | 1.2 µL |
| Platinum Taq Hifi (Life Technologies, 5 units/µL) | 9.6 µL |
| Total volume | 800 µL |

2. An oil-surfactant mix was prepared (20 mL total volume):

| | |
|---|---|
| a. Mineral oil (Sigma) | 18.4 mL |
| b. EM90 (Evonik) | 1.6 mL |

3. 800 µL of oil-surfactant mix and 200 µL of PCR mix were combined into each of 12 Axygen 2.0 mL Maxymum Recovery conical-bottom microcentrifuge tubes (MCT-200-L-C). Tubes were sealed and shaken for 3 seconds 4. Tubes were placed into a Qiagen TissueLyzer II, and shaken for 5 minutes at 14 Hz
5. The emulsion was divided among the wells of a VWR 96-well PCR plate (83007-374), with 160 µL of emulsion added per well
6. Tubes were thermocycled using the following program:

| Initial: | |
|---|---|
| 94° C. | 2' |
| 35 Cycles: | |
| 94° C. | 20" |
| 42° C. | 30" |
| 68° C. | 15" |
| 50 Cycles: | |
| 55° C. | 5.5' |
| 72° C. | 30" |
| Final extension: | |
| 68° C. | 5' |
| Hold: | |
| 10° C. | hold |

The emulsion was broken and beads recovered:
1. The contents of the PCR plate was transferred into 1.5 mL microcentrifuge tubes (VWR 20170-650), with no more than 0.5 mL of emulsion volume per tube
2. 100 uL of 1 uM emB_T7bridgefreeIsceI_2 primer was added to each tube
3. Tubes were topped off with isobutanol, sealed and shaken to mix thoroughly
4. Tubes were centrifuged for 1 min at 14,000 rpm
5. Tubes were placed on a magnetic strip to draw the beads to the side of the tubes, then as much of the supernatant as possible was aspirated as possible while leaving the pelleted beads behind
6. 1 mL of isobutanol was added, mixed well by pipetting up and down until the remaining oil/emulsion volume had dispersed into the isobutanol
7. Tubes were placed on a magnetic strip to draw the beads to the side of the tubes, then the isobutanol was aspirated. Beads from all of the tubes were combined into a single tube by first aspirating the supernatant from the tube into which the beads will be combined and then transferring the full volume from another tube, allowing time for the beads to collect at the magnet, then aspirating the supernatant and repeating
8. 1 mL of fresh isobutanol was added, mixed well and let rest for 60 seconds 9. Isobutanol was aspirated
10. 1 mL of 100% ethanol was added, mixed well and let rest for 60 seconds
11. Ethanol was aspirated
12. Steps 10 and 11 were repeated
13. 1 mL of 70% ethanol was added, mixed well and let rest for 60 seconds
14. Ethanol was aspirated
15. Steps 13 and 14 were repeated
16. 1 mL PBS was added, mixed well and let rest for 60 seconds.
17. PBS was aspirated
18. Steps 16 and 17 were repeated.

Beads that incorporated barcode adapter templates were then sorted from non-barcoded beads using a Becton Dickenson FACS Aria III, utilizing the fluorescence from the Alexa Fluor 647 dye incorporated into the emB_IsceI_RV reverse primer.

Beads were stored in 0.01% sodium azide at 4° C. for storage. The microfluidic device shown in FIGS. 17-19 and described in Example 7 was used encapsulate single cells along with barcoded beads and the other reagents necessary for the barcoding assay. A CD19+IgG+ memory B cell population was FACS sorted and cultured for 6 days in complete IMDM medium (IMDM+10% FBS+100 U/mL IL-2, 50 ng/mL IL-21, 50 ng/mL CD40L, 5 µg/mL anti-CD40L mAb and 1× Normocin) before a cell suspension was prepared using 300 mM betaine with 10 mM NaCl and 0.5 mg/ml BSA as a suspension buffer. Cells were used at a concentration of 2,500 cells/µL and barcoded beads at a concentration of 100,000 beads/uL.

An RT/aqueous barcode mix was prepared as follows:

| | |
|---|---|
| 10X Thermopol DF | 24 µL |
| H$_2$O | 10.6 µL |
| 200X BSA | 4 µL |
| 1M DTT | 2.4 µL |
| 1M MgCl$_2$ | 2.9 µL |
| 50 µM oligo(dT) | 4.8 µL |
| NTP mix (from Life Technologies Megascript T7 kit) | 25.4 µL |
| dNTP (NEB) | 11.9 µL |
| 10% Tween-20 | 0.8 µL |
| Ribolock (Thermo Scientific) | 9.5 µL |
| E. coli inorganic pyrophosphatase (NEB) | 19.1 µL |
| T7 RNAP (NEB) | 9.5 µL |
| T4gp32 (NEB) | 5.7 µL |
| Maxima H- RTase (Thermo Scientific) | 28.6 µL |
| Total volume | 159.1 µL |

The cell and bead suspension was loaded into one sample loop and the RT/barcoding/lysis mix was loaded into the other sample loop using syringes. Cell and bead concentrations were chosen in such a way as to minimize the occurrence of multiple cells or barcodes in a single droplet, while keeping those concentrations high enough so that a large enough number of cells were encapsulated with beads, keeping in mind that cells and beads do not migrate through the tubing at the same rate as the suspension fluid, effectively leading to a dilution. The 4-way valves were switched so that the sample loops were in line with the pump, and all three pumps were activated. The two aqueous inputs were flowed at rates so that they mixed at a 1:2 (cell suspension: RT/barcoding/lysis mix) ratio. The aqueous and oil inputs were flowed at rates so that droplets that were ~150 µm in diameter are formed, specifically 1 µL/min (cell/bead suspension line), 2 µL/min (RT mix line), 3 µL/min (oil line). The emulsion was collected in a Sorenson Bioscience 0.2 mL PCR tube. After the sample had been created, it was first given a pre-heat step (3 minutes at 50° C.) and then incubated for 2 hours at 42° C. to allow the reaction to proceed. Following the reaction, the emulsion was broken using the protocol described below. This produced a purified sample of cDNA for subsequent PCR amplification and sequencing.

The following procedure was used to break the emulsion and recover the product:
1. Phase lock tubes (5Prime) were spun down to push the gel to the bottom.
2. Samples and 200 µL TE buffer, 400 µL phenol chloroform mix, 800 µL chloroform were added to each phase lock tube.
3. Tubes were spun down for 3 minutes at 14,000 g
4. The aqueous layer was transferred to a second pre-spun phase lock tube and an equal volume of phenol chloroform was added
5. Tubes were spun down for 3 minutes at 14,000 g
6. 450 µL of TE was added to the Amicon filter
7. Steps 5 and 6 were repeated
8. 450 µL of 10 mM Tris was added to the Amicon filter
9. Step 5 was repeated
10. Each filter unit was then placed inverted into a new collection tube
11. Tubes were spun at 1000 g for 2 minutes, and the cleaned up sample was spun into the collection tube Two rounds of PCR (PCR1 and PCR2) were then performed, using the following primers in addition to some primer sequences listed in Table 13.

TABLE 13

| Primer name | Sequence (SEQ ID NO:) |
|---|---|
| bc_fwlong_ISceI | GAG AGA CTG ACA GCG TAT CGC CTC CCT CGC GCC ATC AGA CGA GTG CGT GGA TAG GGA TAA CAG GGT AAT AGG A (41) |
| FW_1short | GAG AGA CTG ACA GCG TAT CGC CTC (24) |
| L_GSP1 | TYT GTG GGA CTT CCA CTG CTC (17) |
| G_GSP1 | TCT TGT CCA CCT TGG TGT TGC TG (18) |
| K_GSP1 | CGA TTG GAG GGC GTT ATC CAC (19) |
| 2FR | 50:50 mix of: CGT ATC GCC TCC CTC GCG (25) and CTA TGC GCC TTG CCA GCC C (26) |

TABLE 13-continued

| Primer name | Sequence (SEQ ID NO:) |
|---|---|
| K_GSP2s | CTA TGC GCC TTG CCA GCC CGC TCA GTC AGA TGG CGG GAA GAT GAA GAC (20) |
| L_GSP2s | CTA TGC GCC TTG CCA GCC CGC TCA GGA GGA GGG YGG GAA CAG AGT GAC (21) |
| G_GSP2s | CTA TGC GCC TTG CCA GCC CGC TCA GGG GAA GTA GTC CTT GAC CAG GCA G (22) |

The following PCR1 Q5 (NEB) reaction mix was set up per RT reaction that used a barcode adapter template:

| | |
|---|---|
| H₂O | 11 μL |
| 5x Q5 buffer | 5 μL |
| 50 mM MgCl₂ | 0.15 μL |
| DMSO | 1 μL |
| dNTP | 0.5 μL |
| 10 μM FW1-short | 1 μL |
| 2.5 μM BCfw_longIsceI | 1 μL |
| 10 μM K-GSP1 | 0.56 μL |
| 10 μM L-GSP1 | 0.5 μL |
| 10 μM G-GSP1 | 0.56 μL |
| ET-SSB (NEB) | 0.25 μL |
| 100X BSA | 0.25 μL |
| Q5 enzyme | 0.2 μL |
| cDNA template | 2 μL |

| Initial: | |
|---|---|
| 95° C. | 5' |
| 18 Cycles: | |
| 98° C. | 30" |
| 56° C. | 30" |
| 72° C. | 45" |
| Final extension: | |
| 72° C. | 5' |
| Hold: | |
| 10° C. | hold |

The reactions from PCR1 were then diluted 25× in 10 mM Tris-HCl (pH 8.0) and used as a template in two separate PCR2 reactions, one for kappa and lambda light chains and one for gamma heavy chain.

The following PCR2 Q5 (NEB) reaction mixes were set up per PCR1 reaction:

| | |
|---|---|
| H2O | to 20 μL |
| 5x Q5 buffer | 4 μL |
| 50 mM MgCl₂ | 0.12 μL |
| DMSO | 0.67 μL |
| dNTP | 0.4 μL |
| 10 μM 2FW | 0.8 μL |
| 10 μM K- and L- or G-GSP2 | 0.4 μL |
| BSA | 0.2 μL |
| Phusion | 0.2 μL |
| Dil. PCR1 template | 1.33 μL |

| Initial: | |
|---|---|
| 95° C. | 5' |
| 25 cycles: | |
| 98° C. | 30" |
| 65° C. | 30" |
| 72° C. | 45" |
| Final extension: | |
| 72° C. | 5' |
| Hold: | |
| 10° C. | hold |

10 μL of PCR product was run on a gel (FIG. 24). Bands corresponding to kappa and lambda light chain, and to gamma heavy chain were clearly seen.

Two 4-cycle PCR reactions were performed separately on the heavy and the light chain amplicons to add 454 LibA sequencing adapters. In LibPCR1, "A" adapter was added to the 5' end of the amplicons, and "B" adapter added to the 3' end; and vice versa in LibPCR2. The LibPCR details were as follows, with Lib1-FR primer mix used in LibPCR1 and Lib2-FR mix used in LibPCR2, and the primers are listed in Table 14.

| | |
|---|---|
| H2O | to 20 μL |
| 5x Q5 buffer | 6 μL |
| 50 mM MgCl₂ | 0.18 μL |
| DMSO | 1.2 μL |
| dNTP | 0.6 μL |
| 10 μM Lib1-FR or Lib2-FR mix | 1.2 μL |
| BSA | 0.3 μL |
| Q5 | 0.3 μL |
| Template | 2 μL |

| Initial: | |
|---|---|
| 95° C. | 5' |
| 25 cycles: | |
| 98° C. | 30" |
| 65° C. | 30" |
| 72° C. | 45" |
| Final extension: | |
| 72° C. | 5' |
| Hold: | |
| 10° C. | hold |

TABLE 14

| Primer mix name | Sequence (SEQ ID NO:) |
|---|---|
| Lib1-FR | CCA TCT CAT CCC TGC GTG TCT CCG ACT CAG NNNN CGT ATC GCC TCC CTC GCG CCA T (42) and CCT ATC CCC TGT GTG CCT TGG CAG TCT CAG NNNN CTA TGC GCC TTG CCA GCC CGC TCA (43) mixed 1:1 |
| Lib2-FR | CCT ATC CCC TGT GTG CCT TGG CAG TCT CAG NNNN CGT ATC GCC TCC CTC GCG CCA T (44) and CCA TCT CAT CCC TGC GTG TCT CCG ACT CAG NNNN CTA TGC GCC TTG CCA GCC CGC TCA (45) mixed 1:1 |

Amplicons were then purified using both Ampure (Beckman Coulter) beads cleanup according to manufacturer's instructions using a bead:DNA ratio of 0.68:1 and gel purification using Flashgel Recovery gel (Lonza) according to the manufacturer's instructions.

Amplicons were then quantified using Kapa qPCR library quantification (KAPA) according to the manufacturer's instructions, and the appropriate amounts of the heavy and light chain amplicon libraries were then used in 454 emulsion PCR, and the emulsions broken and clonally amplified 454 beads loaded onto the 454 sequencer for sequencing as per manufacturer's instructions. As both A and B adapters are added to both the 5' and 3' ends of the amplicons, we were able to sequence from both directions and obtain both forward and reverse reads.

Sequences were generated from a standard 454 run, and the resulting sequences were analyzed, though other next generation sequencing platforms could have been used as well.

Sequences were analyzed by writing a computer program. The computer program performed the following steps on the sequence reads from the regions of the 454 pico titer plate. Region 1 sequences were derived from the heavy chain library created as described above. Region 2 sequences were derived from the light chain library created as described above. For each read, two global-local alignments were computed to determine the strand having subsequence matching to the sequences T2' and T1 from Table 15. The global-local alignment scored a match as 0, a mismatch as −1 and used a gap open penalty and gap extension penalty of −1. Scores were required to be greater than −4 or the read was discarded. For the heavy chain region, 611×10³ reads of 841×10³ reads satisfied the alignment score constraint. For the light chain region, 617×10³ reads of 856×10³ reads satisfied the alignment score constraint. Based on the global-local alignments, the sequence of the DNA barcode was extracted from the read. For the heavy chain region reads satisfying the alignment score constraint, 397×10³ reads had a barcode sequence consistent with the expected pattern and were assigned to have the observed barcode. For the light chain region reads satisfying the alignment score constraint, 437×10³ reads had a barcode sequence consistent with the expected pattern and were assigned to have the observed barcode.

Reads with identical DNA barcode sequences were grouped together for assembly. The groups of reads with identical barcodes were assembled using newbler, the 454 assembler. The assembly consensus sequences for region 1 sequences which had identical barcode sequences to region 2 sequences were grouped into heavy and light chain pair sets.

The heavy and light chain pair sets contained heavy and light chain sequences derived from the B cell or B cells present in the emulsion RT bubble.

Among the heavy and light chain read pair sets, 2,551 had at least 10 reads from the heavy chain region and at least 10 reads from the light chain region. Of the 2,551 such pairs, 1,820 had assembled to exactly one heavy chain and exactly one light chain. 61 of those pairs were found to have a heavy and light chain which were unique across the entire data set of sequences produced.

An example of paired heavy and light chain sequences produced from barcoded heavy and light chain reads having shared barcode "GCCGACCACGGCACAAGCGC-CGAAAAT" (SEQ ID NO:124) is (SEQ ID NO: 125)
"MEFGLSWLFLVAILKGVQCGVQLLESGGGLVQPGGSLRLSCAGSQFTFS

TYAMNWVRQAPGKGLEWVSGISGDGYRIQYADSVEGRFSISRDNSNNMVY

LQMTSLRAEDTAVYFCAKDLFPRTIGYFDYWGQGTRVTVSS" (heavy chain amino acid sequence)
and (SEQ ID NO: 126)
"MEAPAQLLFLLLLWLPDTTGKIVMTQSPATLSVSPGERATLSCRASQSI

SINLAWYQHKPGQAPRLLIYGASTRATAIPARFSGSVSGTEFTLTISSLQ

SEDFAVYYCQQYDDWPRTFGQGTKVEI" (light chain amino acid sequence).

The analysis demonstrates the ability to associate the heavy chain sequence from a B cell with the corresponding light chain sequence from a B cell.

TABLE 15

Sequences used to identify DNA barcodes in reads from B cells

| Sequence name | Sequence (SEQ ID NO:) |
|---|---|
| T2' | GGGATAACAGGGTAATAGGA (46) |
| T1 | AGGAGTTTAAACTGGGGG (47) |

L. Example 12

Barcoding Nucleic Acids from Cells Using Barcode Adapter Template Beads in Droplets Made Using a Microfluidic Droplet Device This example describes an embodiment of the invention based on predicted results rather than results actually achieved. A barcode adapter template bead library is prepared as in Example 11, except that emB_BCbridgeISceI_2 is replaced with emB_BCbridgeISceI_N and emB_IsceI_RV is replaced with emB_IScel_RV_n. emB_IS-ceI_RV_n contains unique molecular identifiers (UMI), such that when prepared, the barcode adapter template bead library will comprise beads each with a unique sample barcode and a random H (A,C,T nucleotides) octomer UMI to barcode individual mRNA molecules with different UMIs.

TABLE 16

Additional oligos used to make barcode adapter template bead library with sample barcodes and UMIs in a single reaction

| Primer name | Sequence (SEQ ID NO:) |
| --- | --- |
| emB_BCbridgeIScel_N | ACC CAG TTT AAA CCT CCT HHH THH HHT HHH HTH HHT HHH HTC CTA TTA CCC TGT TAT CCC (48) |
| emB_IScel_RV_n | AlexaFluor647-C18spacer-mCmCC CHH HHH HHH ACC AGT TTA AAC CTC CT (49) |

Cells along with beads are encapsulated in droplets for the barcoding reaction as described in Example 11, with the only difference being PBMCs are used rather than activated memory B cells, and the oligo(dT) used is oligodT_n, with the sequence being CAC GAC CGG TGC TCG ATT TAG TTT TTT TTT TTT TTT TTT TTT TTT T (SEQ ID NO:50). The emulsion is then broken as described in Example 11.

One round of PCR is then performed, using the following primers:

TABLE 17

| Primer name | Sequence |
| --- | --- |
| bc_fwlong_IScel | GAG AGA CTG ACA GCG TAT CGC CTC CCT CGC GCC ATC AGA CGA GTG CGT GGA TAG GGA TAA CAG GGT AAT AGG A (41) |
| FW_1short | GAG AGA CTG ACA GCG TAT CGC CTC (24) |
| RV_1 | CAC GAC CGG TGC TCG ATT TAG (51) |

The following PCR Q5 (NEB) reaction mix is used per reaction, and multiple reactions are set up, and each reaction is cycled for a different number of cycles from 15-26 cycles to find the optimal cycle number to use:

| | |
| --- | --- |
| H$_2$O | 9.65 µL |
| 5x Q5 buffer | 5 µL |
| 50 mM MgCl$_2$ | 0.15 µL |
| DMSO | 1 µL |
| dNTP | 0.5 µL |
| 10 µM FW1-short | 1 µL |
| 2.5 µM BCfw_longIscel | 1 µL |
| 10 µM RV_1 | 1 µL |
| ET-SSB (NEB) | 0.25 µL |
| 100X BSA | 0.25 µL |
| Q5 enzyme | 0.2 µL |
| cDNA template | 5 µL |

| Initial: | |
| --- | --- |
| 95° C. | 5' |
| 15-25 Cycles, in 2 cycle increments: | |
| 98° C. | 30" |
| 56° C. | 30" |
| 72° C. | 45" |
| Final extension: | |
| 72° C. | 5' |
| Hold: | |
| 10° C. | hold |

5 µL of PCR product is run on a gel and the cycle number that gives a good amount of product but is not over cycled is used in subsequent downstream steps.

Product is then prepared according to Illumina's paired end sequencing kit and the forward end sequenced on an Illumina high-throughput sequencer, though other sequencing platforms could have been used as well. Sequences are generated and analyzed. Sample barcodes are then used to assign reads to individual cells, and UMIs are then used to perform single-cell RNA sequencing analysis using methods well established in the field (Nat Methods. 2014 February; 11(2):163-6. doi: 10.1038/nmeth.2772. Epub 2013 Dec. 22).

M. Example 13

Barcode Adapter Template Synthesis Using Combinatorial-Generated Barcodes

A barcode adapter template bead library was synthesized in this example.

Barcode-containing oligos (as in FIG. 15) were combinatorially generated from two oligos, BC_part1_sense and BC_part2 type(1, 2, or 3)_antisense. Each BC_part1_sense and BC_part2_type(1, 2, or 3)_antisense oligos contains a unique sequence, "barcode part1" and "barcode part2", respectively. These sequences combined create a unique barcode sequence. "Barcode part1" and "barcode part2" are (16,11) and (12,7) Hamming codes respectively, following the method of *Generalized DNA barcode design based on Hamming codes, Bystrykh* 2012 *PLoS One.* 2012 7: e36852. Therefore, the barcodes thus designed are error-correcting.

BC_part2 oligos are also divided into three types, BC_part2_type1_antisense, BC_part2_type2_antisense and BC_part2 type3_antisense. This allows for amplification to generate barcode adapter templates with 3 different non-mispriming reverse primers (Rv_type1, Rv_type2 and Rv_type3). When each of those reverse primers is covalently coupled to a different fluorophore, generated barcode adapter template beads can be identified via fluorescence in different colors. In addition, barcode adapter template beads that have more than one type of barcode type will fluoresce in more than one color. As barcode adapter template beads in this example are made in emPCR utilizing limiting dilution to put beads with one barcode-containing oligo with the required primers in a droplet. Poisson statistics indicate that a small percentage of droplets will contain more than one barcode-containing oligo, in effect generating a non-monocode barcode adapter template bead. By having different types of barcode adapter template beads fluorescing in different colors, followed by FACS sorting of monocolor beads will greatly increase the percentage of monocode beads obtained via emPCR generation of barcode adapter template beads.

TABLE 18

Combinatorially generated barcodes - sequences

| Name | Sequence (SEQ ID NO:) |
|---|---|
| Barcode adapter template | Dual-biotin-C18spacer-C18spacer-<br>ATATTAATACGACTCACTATAGGAAGATAGGGATAACAGGGTAATG<br>[barcode part1]*GCTGAGACATGTGAAGAGG*[barcode part2][X]<br>*GAGGGA* DDDD DDDD GCGGG<br>Where [X] = GCTCTTCG (52), TCGTCTCG (53) or ACCTCAGC,<br>(54), the italicized portions are called "fixed sequence 1" and "fixed sequence 2", respectively, and the underlined portion is the molecular barcode, also known as the UMI. |
| | Barcode adapter template sequence is generated from: |
| SAV_bead_linker | Dual-biotin-C18spacer-C18spacer-<br>ATATTAATACGACTCACTATAGGAAGATAGGGATAACAGGGTAATG<br>(55) |
| Linker_free | ATATTAATACGACTCACTATAGGAAGATAGGGATAACAGGGTAATG<br>(56) |
| Barcode-containing oligo | ATATTAATACGACTCACTATAGGAAGATAGGGATAACAGGGTAATG<br>[barcode part1]GCTGAGACATGTGAAGAGG[barcode part2][X]<br>GAGGGA<br>Where [X] = GCTCTTCG (57), TCGTCTCG (58) or ACCTCAGC<br>(59) |
| Rv_type1 | 6-FAM-mCmCCGC HHHH HHHH TCCCTC CGAAGAGC (60) |
| Rv_type2 | Cy3-mCmCCGC HHHH HHHH TCCCTC CGAGACGA (61) |
| Rv_type3 | AlexaFluor647-mCmCCGC HHHH HHHH TCCCTC GCTGAGGT (62) |
| | Barcode-containing oligo is generated from: |
| Make_longbc_fw | GATAGGGATAACAGGGTAATG (63) |
| BC_part1_sense | GATAGGGATAACAGGGTAATG[barcode part1]<br>GCTGAGACATGTGAAGAGG (64) |
| BC_part2_type1_antisense | TCCCTC CGAAGAGC[barcode part2]CCTCTTCACATGTCTCAGC<br>(65) |
| Make_longbc_rv1 | TCCCTC CGAAGAGC (66) |
| BC_part2_type2_antisense | TCCCTC CGAGACGA[barcode part2]CCTCTTCACATGTCTCAGC<br>(67) |
| Make_longbc_rv2 | TCCCTC CGAGACGA (68) |
| BCpart2_type3_antisense | TCCCTC GCTGAGGT[barcode part2]CCTCTTCACATGTCTCAGC<br>(69) |
| Make_longbc_rv3 | TCCCTC GCTGAGGT (70) |

[barcode part1] = SEQ ID NOS: 127-45126;
[barcode part2] = SEQ ID NOS: 45127-47561.

Barcode-containing oligo was PCR generated using the conditions in Table 19 and the following thermocycling conditions: 94° C. for 2 min, followed by 53° C. for 2 hours, 7 cycles of 94° C. for 15 s, 53° C. for 30 s and 68° C. for 20 s, which is then followed by 68° C. for 1 min and a 10° C. hold. The reaction was cleaned up using Zymo DNA cleanup and concentration kit and concentrations quantified with Qubit (Life Technologies).

TABLE 19

Mastermix for making barcode-containing oligos

| | |
|---|---|
| H$_2$O | 14.675 μL |
| 10x buffer | 2.5 μL |
| 50 mM MgSO4 | 0.25 μL |
| 10 mM dNTP | 0.5 μL |

TABLE 19-continued

Mastermix for making barcode-containing oligos

| | |
|---|---|
| BC_part1 (50 nM) | 2 μL |
| BC_part2_type1, 2 or 3_antisense (50 nM) | 2 μL |
| Make_longbc_fw (10 μM) | 1.25 μL |
| Make_longbc_rv_1, 2 or 3 (10 μM) | 1.25 μL |
| Taq polymerase DNA (5 U/μL) | 0.2 μL |
| 3x BSA (0.3 ug/ul) | 0.375 μL |

The size of 82 bp for barcode-containing oligos was confirmed on a gel (FIG. 25, upper left).

9.8 μm SuperAvidin microsphere beads (Bang's Lab) were coupled with biotinylated SAV-bead-linker oligo. 15 million beads were incubated with 60 μL of 10 μM oligo for 1 hour, and then washed 3× with BWB buffer (1M NaCl in TE), followed by 3 washes in 10 mM Tris to generate coupled SAV_ beads_ linker beads.

An emPCR to generate barcode adapter template beads proceeded as follows:

TABLE 20

Mastermix for making barcode adapter template beads

| | |
|---|---|
| $H_2O$ | to 50 µL |
| One Taq 5x buffer | 10 µL |
| SAV-bead-linker coupled beads (50 K/µL) | 10 µL |
| 10 mM dNTP | 1 µL |
| Barcode-containing oligo type1 (10 fg/µL) | 0.3 µL |
| Barcode-containing oligo type2 (10 fg/µL) | 0.3 µL |
| Barcode-containing oligo type3 (10 fg/µL) | 0.3 µL |
| Linker_free (10 µM) | 1 µL |
| Rv_type 1 (100 µM) | 0.6 µL |
| Rv_type2 (100 µM) | 0 µL |
| Rv_type3 (100 µM) | 0.6 µL |
| One Taq 5 U/µL | 0.6 µL |
| TIPP 2 U/µL | 0.075 µL |
| 3x BSA (0.3 µg/µL) | 0.75 µL |

The emulsion was creating by shaking emulsion oil with the mastermix in Table 20. The emulsion oil formulation was 10 mL AR20 silicone oil (Sigma), 7.5 mL 7225C Formulation Aid (Dow Corning), 7.5 mL 0749 Resin (Dow Corning) and 0.1% Triton X-100 (Sigma). 12 mL of emulsion oil was shaken with 4 mL of mock mix (without oligos, primers and enzymes of the mastermix in Table 20) at 30 Hz for 5 min in TissueLyser (Qiagen), and then shaken at 12 Hz for 5 min after adding 4 mL of mastermix. This gave the majority of larger droplets between 30-80 um in diameter. The thermocycling conditions were:

| Initial: | |
|---|---|
| 94° C. | 2' |
| 35 cycles: | |
| 94° C. | 30" |
| 53° C. | 60" |
| 68° C. | 90" |
| 50 cycles: | |
| 94° C. | 30" |
| 59° C. | 6' |
| Hold | |
| 10° C. | |

Emulsion were broken by washing with breaking mix 1 followed by breaking mix 2, followed by 70% ethanol washes, and TE washes. Beads were resuspended in TE with 0.001% Tween 20.

| Breaking Mix 1 | µL |
|---|---|
| Isobutanol | 1200 |
| Isopropanol | 800 |
| AR-20 | 500 |
| TE | 187.8 |
| Linker_free (100 µM) | 12.2 |
| Total volume | 2700 |

| Breaking Mix 2 | µL |
|---|---|
| Isobutanol | 9000 |
| Isopropanol | 9000 |
| TE | 1800 |
| 10% Tween 20 in TE | 200 |
| Total volume | 20000 |

Beads were run on a BD FACS Jazz and bright, monocolor beads were sorted (FIG. 25, right). A barcoding reaction performed as in Example 14 was done to verify that the beads were useable as barcode adapters for barcoding RNA, except that the reaction was done in open PCR with multiple beads in a PCR tube and with purified PBMC RNA. As in FIG. 25, lower left, bands were obtained showing that beads were indeed useable as barcode adapter templates for barcoding RNA.

N. Example 14

Barcoding Nucleic Acids from T Cells Using Barcode Adapter Template Beads in Droplets of Varying Volumes Cryopreserved PBMCs were thawed and incubated in AIM V media (Life Technology) overnight at a density of 3 million cells per mL. T cells were then isolated with magnetic-activated cell sorting (MACS) using CD3 microbeads (Miltenyi Biotec) according to manufacturer' instructions. In brief, T cells were centrifuged at 300 g for 10 minutes, and suspended in MACS buffer (2% fetal bovine serum and 2 mM EDTA in 1xPBS) containing 20% CD3 microbeads for 15 minutes at 4° C. Magnetically labeled T cells were then separated using magnetic separation column, followed by co-stimulation with 1x ionomycin, and 1x phorbol 12-myristate 13-acetate (PMA) for 3 hours. After removing the media containing both stimuli, cells were incubated with 1x of DNAse (Sigma) as anti-clumping agent for 15 minutes.

Cells were centrifuged to remove the supernatant containing DNAse, and washed 3 times with cell suspension buffer (CSB) containing 5% of 1M NaCl, 1.5% of 500 mM EDTA, 33.8% of 4M Betaine, and 7.5% of 20 mg/ml bovine serum albumin (BSA). Cells were also filtered with 40 µm cell strainer (BD Falcon) to remove cell clumps after resuspending in 1mL CSB. Cell suspensions were then run on a droplet generator device as in Example 8 to encapsulate cells and barcode adapter template beads into droplets, where the beads were generated as in Example 13. In this example, cells and beads were encapsulated into droplets of different sizes: 1.4, 3.1 and 5.6 nL.

Droplets containing both cells and barcodes underwent reverse transcription by incubating at 50° C. for 3 minutes followed by 42° C. for 3 hours in the following final reaction buffer composition:

| RT reaction mix | |
|---|---|
| Tris-HCl pH 8 | 20 mM |
| NaCl | 3.33 mM |
| KCl | 10 mM |
| $(NH_4)_2SO_4$ | 10 mM |
| $MgSO_4$ | 15 mM |
| EDTA | 0.5 mM |
| Betaine | 90 mM |
| BSA | 0.4 mg/ml |

-continued

| RT reaction mix | |
|---|---|
| DTT | 4 mM |
| Tween 20 | 0.30% |
| dNTPs | 2 mM mM |
| NTPs | 8 mM mM |
| Ribolock | 1.6 U/μL |
| T7 RNAP | 4 U/μL |
| *E. coli* IPP | 0.001 U/μL |
| T4gp32 | 0.25 μg/μL |
| Maxima H- | 3 U/μL |
| Oligo(dT) | 0.1 μM |
| Random hexamer and octomers | 25 nM |
| Random pentadecamer | 6.25 nM |

The emulsion was then broken with a phenol/chloroform mixture and concentrated in an Amicon 100 kDa column (Millipore) as in Example 8. cDNA were subjected to 18 cycles of PCR1, followed by PCR2 using the reaction mix per RT reaction listed below and thermocycling conditions listed in Table 21. Primers used are in Table 22.

| Reaction mix for PCR1 | | Reaction mix for PCR2 | |
|---|---|---|---|
| H$_2$O | 15.64 μL | H$_2$O | 17.82 μL |
| 5X Q5 Buffer | 6.00 μL | 5X Q5 Buffer | 6.00 μL |
| MgCl$_2$ | 0.19 μL | MgCl$_2$ | 0.18 μL |
| DMSO | 1.20 μL | DMSO | 1.00 μL |
| dNTP | 0.63 μL | dNTP | 0.60 μL |
| Index_sID | 0.63 μL | FW2-N-V2 | 0.60 μL |
| PCR1_short_n_v2 | 0.63 μL | RV2-n | 0.60 μL |
| TRAC 53-78/ TRBC 37-60 | 0.63 μL | TRAC GSP2/ TRBC GSP2 | 0.60 μL |
| ET-SSB | 0.31 μL | BSA | 0.30 μL |
| BSA | 0.31 μL | Q5 Enzyme | 0.30 μL |
| Tipp | 0.60 μL | Template | 2.00 μL |
| Q5 Enzyme | 0.25 μL | Total | 30.00 μL |
| Template | 3.00 μL | | |
| Total | 30.00 μL | | |

TABLE 21

Thermocycling condition of PCR1 and PCR2

| PCR1 | | | PCR2 | | |
|---|---|---|---|---|---|
| 95° C. | 5 minutes | | 95° C. | 5 minutes | |
| 98° C. | 30 seconds | 18 cycles | 98° C. | 30 seconds | 24 cycles |
| 62° C. | 30 seconds | | 65° C. | 30 seconds | |
| 72° C. | 45 seconds | | 72° C. | 35 seconds | |
| 72° C. | 5 minutes | | 72° C. | 5 minutes | |
| 10° C. | Hold | | 10° C. | Hold | |

TABLE 22

Primer sequences for PCR 1 and PCR2

| Name | Sequence (SEQ ID NO:) |
|---|---|
| FW2-N-V2 | CTATGCGCCTTGCCAG AATGATACGGCGACC CCGAGATCTACA (71) |
| Index_sID | GGCGACCACCGAGATCTACAC[i5 index primers]TCG TCG GCA GC GGAAGATAGGGATAACAGGGTAATG (72) |
| PCR1_short_n_v2 | GGCGACCACCGAGATCT ACA (73) |
| PCR1-RV-N v2 | ATTAGGAGACACAATAGGGAGGCA (74) |

TABLE 22-continued

Primer sequences for PCR 1 and PCR2

| Name | Sequence (SEQ ID NO:) |
|---|---|
| RV2-n | GTGGGCTCGGAGATGTGTATAAGAGA (75) |
| TRAC 53-78 | GGTGAATAGGCAGACAGACTTGTCAC (76) |
| TRAC GSP2 | GTGGGCTCGGAGATGTGTATAAGAGACAG N TACACGGCAGGGTCAGGGT (77) and GTGGGCTCGGAGATGTGTATAAGAGACAG NN TACACGGCAGGGTCAGGGT (78) and GTGGGCTCGGAGATGTGTATAAGAGACAG NNN TACACGGCAGGGTCAGGGT (79) and GTGGGCTCGGAGATGTGTATAAGAGACAG NNNN TACACGGCAGGGTCAGGGT (80) (2.5 μM each, pooled and mixed to yield 10 μM) |
| TRBC 37-60 | CTCTGCTTCTGATGGCTCAAACAC (81) |
| TRBC GSP2 | GTGGGCTCGGAGATGTGTATAAGAGACAG N ATGGCTCAAACACAGCGACCTC (82) and GTGGGCTCGGAGATGTGTATAAGAGACAG NN ATGGCTCAAACACAGCGACCTC (83) and GTGGGCTCGGAGATGTGTATAAGAGACAG NNN ATGGCTCAAACACAGCGACCTC (84) and GTGGGCTCGGAGATGTGTATAAGAGACAG NNNN ATGGCTCAAACACAGCGACCTC (85) (2.5 μM each, pooled and mixed to yield 10 μM) |

[i5 index primers] = SEQ ID NOS: 47562-47605.

As can be seen from FIG. 26, at the 3 droplet volumes tested, the reaction was successfully completed.

O. Example 15

Amplifying and Sequencing TCR Alpha and Beta Genes from Barcoded Nucleic Acids

Barcoded T cells cDNA were generated as described in Example 14. In brief, PBMCs were co-stimulated with 1× of ionomycin and PMA in AIM V media for 3 hours. CD3, CD4 or CD8-expressing T cells were magnetically labeled and isolated separately using MACS kits (Miltenyi Biotec) and ran through a droplet device to encapsulate cells with barcode adapter template beads, which were generated as in Example 13. Emulsion containing both cells and barcodes were reverse transcribed at 50° C. for 3 minutes and 42° C. for 3 hours. The emulsion was then broken with a phenol/chloroform mixture and concentrated using an Amicon 100 kDa column (Millipore).

Reverse transcription and PCR1 and PCR2 were performed as in Example 14, with different index_sID primers, each with a unique index ID barcode, used for each sample. This allows for pooling and multiplexing of samples in the same next-gen sequencing run, where different samples are distinguished from one another via the index ID barcode.

PCR2 products were then concentrated with AMPure magnetic beads (Roche) according to manufacturer instruction at a ratio of 1 μl PCR 2 products to 1.8 μl magnetic beads. Samples were then prepared for Illumina sequencing using an additional library PCR to add adapters for Illumina sequencing. Primers used are listed in Table 23.

| H$_2$O | 16.22 μL |
|---|---|
| 5X GC Buffer | 6.00 μL |
| MgCl$_2$ | 0.18 μL |
| DMSO | 1.20 μL |

-continued

| | |
|---|---|
| dNTP | 0.60 μL |
| 10 μM Next i5 n | 0.60 μL |
| 10 μM Next i7 FULL n | 0.60 μL |
| BSA | 0.30 μL |
| Phusion DNA Polymerase | 0.30 μL |
| Template | 4.00 μL |
| Total | 30.00 μL |

Thermocycling Condition for Library PCR

| | | |
|---|---|---|
| 95° C. | 5 minutes | |
| 98° C. | 30 seconds | 4 cycles |
| 65° C. | 30 seconds | |
| 72° C. | 35 seconds | |
| 72° C. | 5 minutes | |
| 10° C. | Hold | |

TABLE 23

Primer sequence used in library PCR Amplification

| Name | Sequence (SEQ ID NO:) |
|---|---|
| Next_i5_n | AATGATACGGCGACCACCGAGATCTA (86) |
| Next i7_FULL_n | CAAGCAGAAGACGGCATACGAGAT TCGCCTTA GTCTCGTGGGCTCGGAGATGTGTATAAG (87) |

Amplified product were cleaned with Pippin Prep and DNA Purification and Concentrator kit (Zymo Research) to remove small fragments and analyzed with agarose gel electrophoresis (FIG. 27), and sequenced using Illumina sequencing.

Paired end reads from Illumina sequencing were analyzed to determine T cell receptor (TCR) germline, TCR CDR3, and infer full length sequence. Sequencing generated 21,207,225 filtered, paired end reads. The DNA barcodes were used to assign paired reads to the transcript of a TCR within individual T cells on the basis of the forward read sequence. The identification of the DNA barcodes within the forward reads was done using a python script. For each forward read, the edit distance to fixed sequence 1 was computed using a global/local alignment. An edit distance of 2 or less was required or the read pair was discarded. From the location of fixed sequence 1 and the known lengths of barcode part1 (BC1) and barcode part2 (BC2), candidate BC1 and BC2 sequences were extracted from the forward read. BC1 and BC2 were checked to verify that they satisfied the Hamming condition for a Hamming(16, 11) or Hamming (12, 7) DNA barcode, respectively (see Table 18 for the sequence and relative positions of the named sequences to one another). On the basis of BC1 and BC2 a paired read was assigned to a specific T cell. As a result 3,712,013 read pairs were assigned to T cells.

Paired reads assigned to T cells were then compared to known variants of V, J and constant germline TCR sequences using the program blastn with an e-value cutoff of $10^{-5}$. If either read of the pair was scored as a hit to a germline by blast, the count of that germline and associated allele was incremented by one for the corresponding TCR alpha or beta chain (of the cell identified by BC1, BC2). In addition for each germline allele combination and specific cell a list of sequences that had a hit to it was stored.

For each cell identified by a unique combination of BC1 and BC2, the v, j and/or constant germline allele composition for alpha and beta chains was then assigned based on the majority of the counts indicated above, and for each germline the sequence that had the longest HSP associated with it was selected as a representative portion of the transcript for that germline.

Next the composition of the CDR3 region was determined using the following steps. For each j germline the location of the sequence of 4 amino acids (AA) satisfying the pattern FG*G was determined when possible, and the list of v germlines that had the combination of CA in the last 10 AA of its sequence was identified. For each cell, the 4 AA pattern of the j germline and the CA combination were sought in all three frames of the translated representative sequence for j. The CDR3 was determined to be the sequence of AA between CA and the 4 AA pattern. The putative AA sequence of the TCR was obtained by combining the AA sequence of the v germline up to CA followed by the CDR3 sequence followed by the AA sequence of the j germline beginning with the 4 AA pattern. Using a similar approach the nucleotide sequence of the CDR3 and the putative full length nucleotide sequence of the TCR were determined.

The D germline and D allele were assessed by evaluating the edit distance based on a global-local alignment between the D germlines and the nucleotide sequence of the CDR3. A D germline/allele was assigned to the TCR provided the edit distance to the closest germline sequence was less than or equal to 2.

Table 24 shows summary statistics for the samples that were processed, including estimated number of cells barcoded, cells with a TCR alpha or beta chain assigned, cells with both a TCR alpha and beta assigned, and number of inferred full length alpha or beta chains.

TABLE 24

TCR alpha and beta chains

| Subject | Estimated number of cells | Cells detected (unique BC1/BC2) | Cells with TCR alpha and/ or beta detected | Cells with beta detected | Cells with alpha detected | Cells with both alpha and beta detected |
|---|---|---|---|---|---|---|
| SBJCT3 | 20800 | 6682 | 6226 | 5159 | 1172 | 105 |
| SBJCT4 | 24046 | 3988 | 3722 | 2772 | 998 | 48 |
| SBJCT5 | 22652 | 3664 | 3435 | 2726 | 751 | 42 |

P. Example 16

Amplifying and Sequencing Cell Subtypes-Specific Genes from Barcoded Nucleic Acids Barcoded T cells cDNA were generated as described in Example 15. In brief, PBMCs were co-stimulated with 1× of ionomycin and PMA in AIM V media for 3 hours. CD3, CD4 or CD8-expressing T cells were magnetically labeled and isolated separately using MACS kits (Miltenyi Biotec) and ran through a droplet device. Emulsion containing both cells and barcodes were reverse transcribed at 50° C. for 3 minutes and 42° C. for 3 hours as in Example 14. The emulsion was then broken with a phenol/chloroform mixture and concentrated using an Amicon 100 kDa column (Millipore). PCR1 and PCR2 at different cycles were then performed using the thermocycling conditions in Table 21, along with the specific primers for T cells targeted subset genes, e.g. CD4, CD8, and interferon gamma (IFNγ) as listed in Table 25. Reaction mixes were prepared as follows:

| Reaction mix for PCR1 | | Reaction mix for PCR2 | |
|---|---|---|---|
| H₂O | 10.61 µL | H₂O | 12.42 µL |
| 5X Q5 Buffer | 6.00 µL | 5X Q5 Buffer | 6.00 µL |
| MgCl₂ | 0.19 µL | MgCl₂ | 0.18 µL |
| DMSO | 1.20 µL | DMSO | 1.00 µL |
| dNTP | 0.63 µL | dNTP | 0.60 µL |
| 2.5 µM index sample ID | 0.63 µL | 10 µM FW2-N-V2 | 0.60 µL |
| 10 µM PCR1_short_n_v2 | 0.63 µL | 1 µM Gene specific primer | 6.00 µL |
| 1 µM Gene specific primer | 6.30 µL | BSA | 0.30 µL |
| ET-SSB | 0.31 µL | Q5 Enzyme | 0.30 µL |
| BSA | 0.31 µL | Template | 2.00 µL |
| Tipp | 0.60 µL | Total | 30.00 µL |
| Q5 Enzyme | 0.25 µL | | |
| Template | 3.00 µL | | |
| Total | 30.00 µL | | |

TABLE 25

T cells targeted gene reverse primer sequence for PCR1 and PCR2 in addition to the sequence used in PCR 1 and PCR 2.

| Name | Sequence (SEQ ID NO:) |
|---|---|
| IFNγ (PCR1) | GCTTCCCTGTTTTAGCTGCTGG (88) |
| IFNγ (PCR2) | GTGGGCTCGGAGATGTGTATAAGAGACAG N CGACAGTTCAGCCATCACTTGG (89) and GTGGGCTCGGAGATGTGTATAAGAGACAG NN CGACAGTTCAGCCATCACTTGG (90) and GTGGGCTCGGAGATGTGTATAAGAGACAG NNN CGACAGTTCAGCCATCACTTGG (91) and GTGGGCTCGGAGATGTGTATAAGAGACAG NNNN CGACAGTTCAGCCATCACTTGG (92) (2.5 µM each, pooled and mixed to yield 10 µM) |
| CD4 (PCR1) | GCTGAGACACGGAGAGGGTC (93) |
| CD4 (PCR2) | GTGGGCTCGGAGATGTGTATAAGAGACAG N AGCAGGTGGGTGTCAGAGTT (94) and GTGGGCTCGGAGATGTGTATAAGAGACAG NN AGCAGGTGGGTGTCAGAGTT (95) and GTGGGCTCGGAGATGTGTATAAGAGACAG NNN AGCAGGTGGGTGTCAGAGTT (96) and GTGGGCTCGGAGATGTGTATAAGAGACAG NNNN AGCAGGTGGGTGTCAGAGTT (97) (2.5 µM each, pooled and mixed to yield 10 µM) |
| CD8 (PCR1) | GTGAGGGCGAGAGTAGGCAG (98) |
| CD8 (PCR2) | GTGGGCTCGGAGATGTGTATAAGAGACAG N TCACCGAGGAAGGACCCTCT (99) and GTGGGCTCGGAGATGTGTATAAGAGACAG NN TCACCGAGGAAGGACCCTCT (100) and GTGGGCTCGGAGATGTGTATAAGAGACAG NNN TCACCGAGGAAGGACCCTCT (101) and GTGGGCTCGGAGATGTGTATAAGAGACAG NNNN TCACCGAGGAAGGACCCTCT (102) (2.5 µM each, pooled and mixed to yield 10 µM) |

PCR2 products were then prepared for Illumina sequencing as in Example 15, and the products were analyzed with agarose gel electrophoresis (FIG. 27) before Illumina sequencing.

Paired end reads from Illumina sequencing were analyzed to determine T cell subtype based on the gene specific markers. Sequencing generated 19,205,611 filtered, paired end reads. The DNA barcodes were used to assign paired reads to transcripts within individual T cells on the basis of the forward read sequence. The identification of the DNA barcodes within the forward reads was done using a python script. For each forward read, the edit distance to fixed sequence 1 was computed using a global/local alignment. An edit distance of 2 or less was required or the read pair was discarded. From the location of fixed sequence 1 and the known lengths of barcode part1 (BC1) and barcode part 2 (BC2), candidate BC1 and BC2 sequences were extracted from the forward read. BC1 and BC2 were checked to verify that they satisfied the Hamming condition for a Hamming (16, 11) or Hamming(12, 7) DNA barcode, respectively. For forward reads satisfying the Hamming condition, a candidate molecular barcode was extracted based on the known lengths of X, fixed sequence 2 and the molecular barcode (see Table 18 for the sequence and relative positions of the named sequences to one another). If the molecular barcode sequence had no "C" nucleotides, the paired reads were assigned to a T cell (on the basis of BC1 and BC2) and a specific transcript within the T cell (on the basis of the molecular barcode). 3,902,569 read pairs were assigned to transcripts within individual T cells.

Paired reads assigned to T cell transcripts were then compared to known splice variants of the marker genes using the program blastn with an e-value cutoff of $10^{-6}$ and setting perc_identity to 98. If either read of the pair was scored as a hit by blast, the corresponding transcript from the T cell (identified by BC1, BC2 and the molecular barcode) was associated with the marker gene.

For each cell identified by a unique combination of BC1 and BC2, the number of distinct times a transcript from a given marker gene was seen was determined by counting the number of distinct molecular barcodes observed from read pairs associated with the given marker gene.

The number of each type of T cell detected was determined on the basis of the marker genes. T cells where it was determined that at least one CD4 transcript and one IFNγ transcript were assigned were counted as Th1 cells. T cells where it was determined that at least one CD4 transcript was assigned and no IFNγ transcript was assigned were counted as non-Th1 CD4 samples. T cells where it was determined that at least one CD8 transcript and one IFNγ transcript were identified were counted as IFNγ+ cytotoxic T cells. T cells where it was determined that at least one CD8 transcript and no IFNγ transcript was assigned were counted as IFNγ cytotoxic T cells.

Table 26 shows the total number of CD4 T cells detected, the number of Th1 CD4 T cells, total cytotoxic T cells and IFNγ+ cytotoxic T cells resulting from processing three different samples using the procedure described here.

TABLE 26

Subset summary.

| Subject | CD4 | CD4 Th1 | IFNγ– CD8 | IFNγ+ CD8 |
|---|---|---|---|---|
| SBJCT3 | 19 | 0 | 31 | 0 |
| SBJCT4 | 26 | 1 | 43 | 1 |
| SBJCT5 | 28 | 0 | 26 | 2 |

Q. Example 17

Performing Single Cell Transcriptomics

Barcoded T cells cDNA were generated as described in Example 15. In brief, PBMCs were co-stimulated with 1× of ionomycin and PMA in AIM V media for 3 hours. CD3, CD4 or CD8-expressing T cells were magnetically labeled and isolated separately using MACS kits (Miltenyi Biotec) and ran through a droplet device. Emulsion containing both cells and barcodes were reverse transcribed at 50° C. for 3 minutes and 42° C. for 3 hours as in Example 14. The emulsion was then broken with a phenol/chloroform mixture and concentrated using an Amicon 100 kDa column (Millipore). A single round of PCR was performed to amplify the entire transcriptome, conditions shown below:

| Whole transcriptome PCR conditions | |
|---|---|
| H$_2$O | 28.525 µL |
| 5X Q5 buffer | 12 µL |
| Mg++ | 0.375 µL |
| DMSO | 2.4 µL |
| dNTP | 1.25 µL |
| index sID (2.5 µM) | 5.00 µL |
| PCR1_short_n_v2 (10 µM) | 1.25 µL |
| PCR1-RV-N-v2 (10 µM) | 1.25 µL |
| ET-SSB | 0.625 µL |
| BSA | 0.625 µL |
| Tipp | 1.2 µL |
| Q5 enzyme | 0.5 µL |
| Template | 5 µL |
| total | 60 µL |

| Thermocycling conditions | | |
|---|---|---|
| 95° C. | 5 minutes | |
| 98° C. | 30 seconds | 15 cycles |
| 62° C. | 30 seconds | |
| 72° C. | 10 minutes | |
| 72° C. | 5 minutes | |
| 10° C. | Hold | |

An adapter was added to the library using 5 cycles of PCR, with the same PCR conditions and thermocycling conditions as above, but using FW2-n-V2 as the forward primer instead. Samples were then pooled, cleaned using Ampure beads and prepared for Illumina sequencing using Nextera XT DNA Preparation kit (Illumina), which tagmented DNA into smaller fragments, using manufacturer's instructions, except that 5 ng of DNA template was used, and custom in-house primers were used instead during the amplification step. The house primers used, Next_i5_n_v2 and Next_i7_n ensured that only tagmented fragments containing the barcode would be amplified. A gel was run, and shown in FIG. 29.

TABLE 27

| Additional primers used for whole transcriptomic amplification and library prep | |
|---|---|
| Name | Sequence (SEQ ID NO:) |
| v2_PCR1_RV_n | ATTAGGAGACACAATAGGGAGGCA (103) |
| Next_i5_n_v2 | CTATGCGCCTTGCCAG AATGATAC (104) |
| Next_i7_n | CAAGCAGAAGACGGCATACGAGAT TCGCCTTA GTCTCGTGGGCTCGG (105) |

The barcoded amplicon library was sequenced using an Illumina NextSeq instrument. Paired end reads were analyzed to associate paired reads with individual cells, and to identify the genes that were expressed in those cells. Sequencing generated 371,918,220 filtered, paired end reads. The DNA barcodes were used to assign paired reads to transcripts within individual cells on the basis of the forward read sequence. The identification of the DNA barcodes within the forward reads was done using a python script. For each forward read, the edit distance to fixed sequence 1 was computed using a global/local alignment. An edit distance of 2 or less was required or the read pair was discarded. From the location of fixed sequence 1 and the known lengths of BC1 and BC2, candidate BC1 and BC2 sequences were extracted from the forward read. BC1 and BC2 were checked to verify that they satisfied the Hamming condition for a Hamming(16, 11) or Hamming(12, 7) DNA barcode, respectively. For forward reads satisfying the Hamming condition, a candidate molecular barcode was extracted based on the known lengths of X, fixed sequence 2 and the molecular barcode. If the molecular barcode sequence had no "C" nucleotides, the paired reads were assigned to a cell (on the basis of BC1 and BC2) and a specific transcript within the cell (on the basis of the molecular barcode). 37,110.172 read pairs were assigned to transcripts within individual cells.

Paired reads assigned to cellular transcripts were then compared to known splice variants of genes as reported in release 78 of Ensembl (www.ensembl.org) using the program blastn with an e-value cutoff of $10^{-6}$ and setting perc_identity to 98. If either read of the pair was scored as a hit by blast, the corresponding transcript from the cell (identified by BC1, BC2 and the molecular barcode) was associated with gene If there was more than one blast hit, the best match was selected by finding the gene having the largest sum of lengths of HSPs for forward and reverse reads. In case of a tie between two different genes, assignment of the read pair to a gene was considered ambiguous and not considered further.

For each cell identified by a unique combination of BC1 and BC2, the number of distinct times a transcript from a given gene was seen was determined by counting the number of distinct molecular barcodes observed from read pairs associated with the given gene.

Table 33 show the genes most frequently detected after processing four samples using this procedure. The table shows the Ensembl gene ID, the Ensembl description of the gene and the number of cells the gene was detected in.

R. Example 18

Incorporating Barcode Adapter into 5' End of 1st Strand cDNA

This example describes an embodiment of the invention based on predicted results rather than results actually achieved. Cells and barcode adapter template are put together in reaction containers whereby the majority of reaction containers have only one cell and one template molecule, or one cell and one barcode adapter template bead, for example, by a droplet generator device and the reaction containers are water-in-oil droplets, such as in example 14. The barcode adapter sequence comprises a fixed sequence, a barcode sequence, optionally a UMI, and either oligo(dT) or a random or semi-random sequence (Barcode_adapter_5c_oligodT and Barcode_adapter_5c_randomer respectively in Table 28), or in combination. The template switching oligo (TSO) comprises a fixed sequence, optionally a UMI, and a 1$^{st}$ strand cDNA complementary sequence (5'adapter in Table 28).

The reverse transcription reaction is performed at 50° C. for 3 minutes, followed by 42° C. for 3 hours, in the following reaction conditions:

| RT reaction mix | |
|---|---|
| Tris-HCl pH 8 | 20 mM |
| NaCl | 3.33 mM |
| KCl | 10 mM |
| $(NH_4)_2SO_4$ | 10 mM |
| $MgSO_4$ | 15 mM |
| EDTA | 0.5 mM |
| Betaine | 90 mM |
| BSA | 0.4 mg/ml |
| DTT | 4 mM |
| Tween 20 | 0.30% |
| dNTPs | 2 mM mM |
| NTPs | 8 mM mM |
| Ribolock | 1.6 U/μL |
| T7 RNAP | 4 U/μL |
| E.coli IPP | 0.001 U/μL |
| T4gp32 | 0.25 μg/μL |
| Maxima H- | 3 U/μL |
| Oligo(dT) or random primer | 0.1 μM |

Barcoding occurs during the RT reaction as the barcode adapter primes the reaction and is incorporated into the 5' end of 1$^{st}$ strand cDNA. Barcode adapters are generated off either an RNAP or DNAP (with the appropriate RNA promoter or strand-displacing DNAP recognition site, such as a nick created by a nicking enzyme, on the barcode adapter template) as reverse transcription is able to utilize both DNA and RNA as primers (FIGS. 8 and 9).

The emulsion is broken as in Example 14, and the resulting barcoded nucleic acid library is then pooled and amplified using forward and reverses primers that comprise sequences complementary to the fixed sequences added by 5'adapter and barcode_adapter_5c_oligodT or barcode_adapter_5c_randomer in the barcoding reaction respectively, such as in Example 17. The reaction conditions are shown below:

| | | |
|---|---|---|
| $H_2O$ | 28.525 | μL |
| 5x Q5 buffer | 12 | μL |
| Mg++ | 0.375 | μL |
| DMSO | 2.4 | μL |
| dNTP | 1.25 | μL |
| index sID (2.5 μM) | 5.00 | μL |
| PCR1_short_n_v2 (10 μM) | 1.25 | μL |
| PCR1-RV-N-v2 (10 μM) | 1.25 | μL |
| ET-SSB | 0.625 | μL |
| BSA | 0.625 | μL |
| Tipp | 1.2 | μL |

| -continued | |
|---|---|
| Q5 enzyme | 0.5 μL |
| Template | 5 μL |
| total | 60 μL |

| Thermo cycling conditions | | |
|---|---|---|
| 95° C. | 5 minutes | |
| 98° C. | 30 seconds | 15 cycles |
| 62° C. | 30 seconds | |
| 72° C. | 10 minutes | |
| 72° C. | 5 minutes | |
| 10° C. | Hold | |

Target genes of interest can also be amplified by performing amplification using forward primers comprising gene-specific sequences and using a reverse primer comprising sequences complementary to the fixed sequence added by barcode_adapter_5c_oligodT or barcode_adapter_5c_randomer in the barcoding reaction, such as in Examples 14 and 16. The reaction conditions for amplifying TCR alpha and beta chains in two successive PCR reactions are shown below, where the products of PCR1 were diluted 50× before being used in PCR2:

| Reaction mix for PCR1 | | Reaction mix for PCR2 | |
|---|---|---|---|
| $H_2O$ | 15.64 μL | $H_2O$ | 17.82 μL |
| 5X Q5 Buffer | 6.00 μL | 5X Q5 Buffer | 6.00 μL |
| $MgCl_2$ | 0.19 μL | $MgCl_2$ | 0.18 μL |
| DMSO | 1.20 μL | DMSO | 1.00 μL |
| dNTP | 0.63 μL | dNTP | 0.60 μL |
| PCR1_i5_new | 0.63 μL | FW2-N-V2 | 0.60 μL |
| PCR1_short_n_v2 | 0.63 μL | RV2-n | 0.60 μL |
| TRAC 53-78/TRBC 37-60 | 0.63 μL | TRAC GSP2/TRBC GSP2 | 0.60 μL |
| ET-SSB | 0.31 μL | BSA | 0.30 μL |
| BSA | 0.31 μL | Q5 Enzyme | 0.30 μL |
| Tipp | 0.60 μL | Template | 2.00 μL |
| Q5 Enzyme | 0.25 μL | Total | 30.00 μL |
| Template | 3.00 μL | | |
| Total | 30.00 μL | | |

| Thermocycling condition of PCR1 and PCR2 | | | | | |
|---|---|---|---|---|---|
| PCR1 | | | PCR2 | | |
| 95° C. | 5 minutes | | 95° C. | 5 minutes | |
| 98° C. | 30 seconds | 18 cycles | 98° C. | 30 seconds | 24 cycles |
| 62° C. | 30 seconds | | 65° C. | 30 seconds | |
| 72° C. | 45 seconds | | 72° C. | 35 seconds | |
| 72° C. | 5 minutes | | 72° C. | 5 minutes | |
| 10° C. | Hold | | 10° C. | Hold | |

The library is then prepared for next-gen sequencing, such as on the Illumina or Ion Torrent platform.

TABLE 28

| Primer sequences | |
|---|---|
| Primers | Sequence (SEQ ID NO:) |
| 5' adapter | GGAAGATAGGGATAACAGGGTAATG [UMI] GCGGG (106 ) |
| Barcode_adapter_5c_oligodT | ATTAGGAGACACAATAGGGAGGCA [barcode part1] GCTGAGACATGTGAAGAGG [barcode part2][X] GAGGGA [UMI] TTTTT TTTTT TTTTT TTTTT TTTTT, |

TABLE 28-continued

Primer sequences

| Primers | Sequence (SEQ ID NO:) |
|---|---|
| | Where [X] = GCTCTTCG (107), TCGTCTCG (108) or ACCTCAGC, (109) and the barcode comprises [barcode part1] and [barcode part2] |
| Barcode_adapter_5c_randomer | ATTAGGAGACACAATAGGGAGGCA [barcode part1] GCTGAGACATGTGAAGAGG [barcode part2][X]GAGGGA [UMI] N$_x$, Where x ranges from 6 to 15, [X] = GCTCTTCG (110), TCGTCTCG (111) or ACCTCAGC, (112), and the barcode comprises [barcode part1] and [barcode part2] |

S. Example 19

Incorporating Barcode_Adapter into 5' End During PCR

This example describes an embodiment of the invention based on predicted results rather than results actually achieved. Cells and barcode_adapter template are put together in reaction containers whereby the majority of reaction containers have only one cell and one template molecule, or one cell and one barcode_adapter template bead, for example, by a droplet generator device and the reaction containers are water-in-oil droplets, such as in example 14. The template switching oligo (TSO) comprises a fixed sequence, optionally a UMI, and a $1^{st}$ strand cDNA complementary sequence (5'adapter in Table 29). The 3' adapter sequence comprises a fixed sequence, optionally a UMI, and either oligo(dT) or a random or semi-random sequence (3'_adapter_oligodT and 3'_adapter_randomer respectively in Table 29), or in combination.

The reverse transcription reaction with a cell and a barcode_adapter template bead is performed at 50° C. for 3 minutes, followed by 42° C. for 3 hours, followed by standard PCR cycling conditions, in the following reaction conditions:

| RT reaction mix | |
|---|---|
| Tris-HCl pH 8 | 20 mM |
| NaCl | 3.33 mM |
| KCl | 10 mM |
| (NH$_4$)$_2$SO$_4$ | 10 mM |
| MgSO$_4$ | 7 mM |
| EDTA | 0.5 mM |
| Betaine | 90 mM |
| BSA | 0.4 mg/ml |
| DTT | 4 mM |
| Tween 20 | 0.30% |
| dNTPs | 2 mM |
| Ribolock | 1.6 U/μL |
| Klenow fragment | 0.4 U/μL |
| Nt.BbvCI | 0.3 U/μL |
| E. coli IPP | 0.001 U/μL |
| T4gp32 | 0.25 μg/μL |
| Maxima H- | 3 U/μL |
| 5' adapter | 1 μM |
| 3'_adapter_PCR_oligodT and/or 3'_adapter_PCR_randomer | 0.1 μM (each) |
| 3'_PCR_primer | 0.5 μM |

5'_PCR_barcode_adapter_primer is generated off a barcode_adapter_template using either a DNAP (with the appropriate strand-displacing DNAP recognition site, such as a nick created by a nicking enzyme, on the barcode_adapter_template). Here, Klenow fragment is used as the DNAP and Nt.BbvCI is used as the nicking endonuclease, and the recognition site is "CCTCAGC". After reverse transcription, primers with their 3'end complementary to the adapter sequences added to the $1^{st}$ strand cDNA are used for amplification, with the forward primer being 5'_PCR_barcode_adapter_primer, which is generated from barcode adapter templates, and reverse primer being 3'_PCR_primer.

Barcoding occurs during the PCR reaction as the barcode_adapter (5'_PCR_barcode_adapter_primer) is the forward primer, and the barcode adapter is incorporated into the 5' end of $1^{st}$ strand cDNA (FIG. 11).

Target genes of interest can also be amplified by performing amplification using 5'_PCR_barcode_adapter_primer as the forward primer, and reverse primers comprising gene-specific sequences.

The library is then pooled and prepared for next-gen sequencing, such as on the Illumina or Ion Torrent platform.

TABLE 29

Primer sequences

| Primers | Sequence (SEQ ID NO:) |
|---|---|
| 5'adapter | GGAAGATAGGGATAACAGGGTAATG [UMI] GCGGG (106) |
| 3'_adapter_PCR_oligodT | ATTAGGAGACACAATAGGGAGGCA [UMI] TTTTT TTTTT TTTTT TTTTT TTTTT (113) |
| 3'_adapter_PCR_randomer | ATTAGGAGACACAATAGGGAGGCA [UMI] N$_x$ (114), where x ranges from 6-15 |
| 5'_PCR_barcode_adapter_primer | GGCGACCACCGAGATCTACAC [barcode part1] GCTGAGACATGTGAAGAGG [barcode part2] |

TABLE 29-continued

Primer sequences

| Primers | Sequence (SEQ ID NO:) |
|---|---|
| | GGAAGATAGGGATAACAGGGTAATG (115), the barcode comprises [barcode part1] and [barcode part2] |
| 3'_PCR_primer | ATTAGGAGACACAATAGGGAGGCA (116) |

T. Example 20

Incorporating Barcode_Adapter into 3' End During PCR

This example describes an embodiment of the invention based on predicted results rather than results actually achieved. This example is similar to Example 19, except that the barcode adapter generated from barcode adapter templates is used as the reverse primer in PCR. Reverse transcription is performed as in Example 19, and in PCR 5'_PCR_primer is the forward primer, and 3'_PCR_barcode_adapter_primer is generated from barcode_adapter_template and used as the reverse primer (FIG. 12). The reverse transcription reaction with a cell and a barcode adapter template bead is performed at 50° C. for 3 minutes, followed by 42° C. for 3 hours, followed by standard PCR cycling conditions, in the following reaction conditions:

| RT reaction mix | |
|---|---|
| Tris-HCl pH 8 | 20 mM |
| NaCl | 3.33 mM |
| KCl | 10 mM |
| $(NH_4)_2SO_4$ | 10 mM |
| $MgSO_4$ | 7 mM |
| EDTA | 0.5 mM |
| Betaine | 90 mM |
| BSA | 0.4 mg/ml |
| DTT | 4 mM |
| Tween 20 | 0.30% |
| dNTPs | 2 mM |
| Ribolock | 1.6 U/μL |
| Klenow fragment | 0.4 U/μL |
| Nt.BbvCI | 0.3 U/μL |
| *E. coli* IPP | 0.001 U/μL |
| T4gp32 | 0.25 μg/μL |
| Maxima H- | 3 U/μL |
| 5' adapter | 1 μM |
| 3'_adapter_PCR_oligodT and/or 3'_adapter_PCR_randomer | 0.1 μM (each) |
| 5'_PCR_primer | 0.5 μM |

Target genes of interest can also be amplified by performing amplification using and reverse forward primers comprising gene-specific sequences, and 3'_PCR_barcode_adapter_primer as the reverse primer.

The library is then pooled and prepared for next-gen sequencing, such as on the Illumina or Ion Torrent platform.

TABLE 30

Primer sequences

| Primers | Sequence (SEQ ID NO:) |
|---|---|
| 5'_PCR_primer | GGAAGATAGGGATAACAGGGTAATG (117) |
| 3'_PCR_barcode_adapter_primer | GTGGGCTCGGAGATGTGTATAAGAGA [barcode part1] GCTGAGACATGTGAAGAGG [barcode part2] ATTAGGAGACACAATAGGGAGGCA (118), the barcode comprises [barcode part1] and [barcode part2] |

U. Example 21

Barcoding RNA from Non-Cell Sources

In embodiments of the current invention, all RNA in the reaction container are barcoded, provided that the primer used in the reaction can bind to and initiate reverse transcription for a particular RNA. Therefore, exogenously introduced RNA can also be barcoded. In this example, RNA generated using in vitro transcription was barcoded.

SpikeIn sequence was ordered from IDT and PCR amplified with Phusion DNA polymerase using SPIKEIN-FW and SPIKEIN-RV as primers to obtain double stranded material with a 5' T7 RNAP promoter sequence and a 3' poly A tail. The product was then cleaned up with Qiagen MinElute kit and the DNA product was used for in vitro transcription with Life Technologies' T7 MEGAScript kit. The RNA thus obtained was then cleaned up by washing and concentrating with 10 mM Tris using Amicon 30 kDA columns (Millipore).

In each well of eight 96-well plates, a single memory B cell along with 0.5 ng yeast tRNA (Life Technologies) and 0.1 pg of Spike-In RNA were reverse transcribed. In a 10 μL reaction per well, the reaction was:

| | |
|---|---|
| 10x MMLV buffer (NEB) | 1 μL |
| 10 mM Tris pH 8.0 | To 10 μL |
| 1 μM biotinylated oligo(dT)$_{25}$ (SEQ ID NO: 40) | 0.003 μL |
| 100 mM $MgCl_2$ | 0.3 μL |
| Ribolock | 0.025 μL |
| T4gp32 (NEB) | 0.006 μL |
| MaxH- (Fisher Scientific) | 0.04 μL |
| wellID-adapter | 1 μL |

The reaction was incubated at 55° C. for 3 minutes, and then at 42° C. for 2 hours. Each well in a 96-well plate had a different well barcode in the wellID-adapter. The reaction was then cleaned up by binding $1^{st}$ strand cDNA with streptavidin paramagnetic C1 Dynabeads (Life Technologies) that binds to the biotinylated oligodT, and then using a magnet to pull down the $1^{st}$ strand cDNA, and washing them 3× with BWB buffer (2M NaCl in TE) and then 3× with 10 mM Tris, and resuspended in 15 μL of 10 mM Tris.

Two rounds of PCR amplification was done to amplify up heavy and light chain immunoglobulin genes. A different plate barcode sequence was added to all pooled barcoded cDNA in a different plate.

Per Well for PCR1:

| | |
|---|---|
| H₂O | 27.575 μL |
| 5x Q5 Buffer | 12.5 μL |
| MgCl2 | 0.375 μL |
| DMSO | 2.5 μL |
| dNTP | 1.25 μL |
| FW1-short | 2.5 μL |
| K-GSP1 | 1.4 μL |
| L-GSP1 | 1.25 μL |
| G-GSP1 | 1.4 μL |
| ET-SSB (NEB) | 0.625 μL |
| BSA | 0.625 μL |
| Q5 Enzyme | 0.5 μL |
| Plate-ID | 5 μL |
| Template | 5 μL |

Product from PCR1 was diluted 50× and used in PCR2. Reaction per well for PCR2:

| | |
|---|---|
| H₂O | 18.42 μL |
| 5x Q5 buffer | 6 μL |
| MgCl₂ | 0.18 μL |
| DMSO | 1 μL |
| dNTP | 0.6 μL |
| 2FR | 0.6 μL |
| G-GSP2 or K-GSP2 and L-GSP2 | 0.6 μL |
| BSA | 0.3 μL |
| Q5 | 0.3 μL |
| Template | 2 μL |

The amounts of resulting amplified material was normalized and prepared as in Example 11 for 454 sequencing. Primers used in this example may be found in Tables 13, 14 and 32.

454 reads obtained were binned based on plate- and well-ID barcodes. Therefore, reads can be binned back to the original well in a specific plate. Reads were assembled with Newbler after clipping off the barcode sequences. For each contig, we performed a Smith-Waterman alignment of the contig with the Spike-In sequence using a scoring matrix of 2 for a match, −1 for a mismatch, −1 for a gap open and −1 for a gap extension. Any contig with a score >800 was considered a match. We counted the number of wells on each plate for which a match was observed. The Spike-In sequence was detected in the large majority of the wells (Table 31).

TABLE 31

Wells in which Spike-In sequence was detected

| RT Plate physical barcode | Plate-ID barcode | Wells in which sequence was present | Percent (%) |
|---|---|---|---|
| F041172 | p029 | 87 | 90.6 |
| F041173 | p061 | 76 | 79.2 |
| F041174 | p066 | 90 | 93.8 |
| F041189 | p069 | 93 | 96.9 |
| F041056 | p103 | 92 | 95.8 |
| F041170 | p149 | 87 | 90.6 |
| F041175 | p158 | 94 | 97.9 |
| F041171 | p193 | 82 | 85.4 |

TABLE 32

Sequences used

| Primers/ Oligos | Sequence (SEQ ID NO:) |
|---|---|
| Spike-In | ATCGTCTAAT ACGACTCACT ATAGGGTCCC TGAGCTGAAC GGGAAGGAAG GCTGGGGCTC ATTTGAGGTG CAGCTGTTGG AGATGACCCA GTCTCCAGCC TCCCTGCGTC ATGGGTGTGA ACCATTAGCT GTGCTCGCGC TACTCTCTCT TTCTGGCCTG GAGGCTATCC AGCACAGCGA CACCCACTCC TCCGTACTCC AAAGATTCAG GTTTACTCAC GTCATCCAGC AGAGAATGGA AAGTCAAATT TCCTGAATTG CTATGTGTCT GGGTTTCATC CATCCGACAT TGAAGTTGAC TTACTGAAGA ATGGAGAGAG AATTGAAAAA GTGGAGCATT CAGACTTGTC TTTCAGCAAG GACTGGTCTT TCTATCTCTT GTACTACACT GAATTCACCC CCACTGAAAA AGATGAGTAT GCCTGCCGTG TGAACCATGT GACTTTGTCA CAGCCCAAGA TAGTTAAGTG GGCACAAAGA GCTTCAACAG GGGAGAATCG AGACATGTAA GCAGCATCAT GGAGCTGGGC TGCCTGGTCA AGGAC (119) |
| SPIKEIN-FW | ATCGTCTAATACGACTCACTATAGGGTCC (120) |
| SPIKEIN-RV | TTTTT TTTTT TTTTT TTTTT TTTTT TTTTT TTTTT GTC CTT GAC CAG GCA GCC CAG (121) |
| wellID-adapter | CACGACCGGUGCTCGATTTAG[well-barcode]AGGAGGG (122) |
| Plate-ID | GAGAGACTGACAGCGTATCGCCTCCCTCGCGCCATCAG [plate-barcode] CACGACCGGTGCTCGATTTAG (123) |

[well-barcode] = SEQ ID NOS: 47606-47711;
[plate-barcode] = SEQ ID NOS: 47712-47719.

V. Example 22

Barcoding RNA from Non-Cell Sources to Identify Cell Populations

This example describes an embodiment of the invention based on predicted results rather than results actually achieved. As shown in Example 21, exogenously introduced RNA can be barcoded. In this example, barcoded RNA is used to identify specific cell populations. Spike-In DNA is generated as in Example 21, except that SPIKEIN-FW has a 5' NH2 modification. It is conjugated to an anti-CD4 antibody using All-in-One Antibody-Oligonucleotide Conjugation Kit (Solulink). RNA generated from Spike-In DNA using in vitro transcription may also be conjugated instead to anti-CD4 antibody.

T cells are prepared and sequenced as in Example 15, with an additional step being the T cells are incubated with the Spike-In conjugated anti-CD4 antibody before running the T cells on a droplet generator and subsequently barcoding the RNA. Reads obtained are binned based on index-ID and barcodes added by barcode adapters. Therefore, reads can be binned back to the original reaction container. Smith-Waterman alignment of the contig with the Spike-In sequence using a scoring matrix of 2 for a match, −1 for a mismatch, −1 for a gap open and −1 for a gap extension is done. Any contig with a score >800 is considered a match. We then count the reaction containers in which a match was observed. For reaction containers in which the Spike-In sequence is detected, the T cell is then identified as a CD4 T cell (FIG. 14A). Multiple antibodies coupled with different Spike-In sequences can be used, with the end result being different cells with different cell surface antigens can be identified in the same experimental run.

W. Example 23

Barcoding RNA from Non-Cell Sources to Identify Antigen-Specific B Cells

This example describes an embodiment of the invention based on predicted results rather than results actually achieved. In this example, exogenously introduced RNA is barcoded and used to identify antigen-specific B cells. Spike-In DNA is generated as in Example 21, except that SPIKEIN-FW has a 5' NH2 modification. It is conjugated to an influenza hemagglutinin antigen using All-in-One Antibody-Oligonucleotide Conjugation Kit (Solulink). RNA generated from Spike-In DNA using in vitro transcription may also be conjugated instead to hemagglutinin.

B cells from influenza-vaccine immunized mice are prepared as in Example 8 and sequenced, with an additional step being the B cells are incubated with the Spike-In conjugated antigen before barcoding them. Reads obtained are binned based on index-ID and barcodes added by barcode adapters. Therefore, reads can be binned back to the original reaction container. Smith-Waterman alignment of the contig with the Spike-In sequence using a scoring matrix of 2 for a match, −1 for a mismatch, −1 for a gap open and −1 for a gap extension is done. Any contig with a score >800 is considered a match. We then count the reaction containers in which a match was observed. For reaction containers in which the Spike-In sequence is detected, the B cell is then identified as being hemagglutinin-specific (FIG. 14B). Multiple antigens coupled with different Spike-In sequences can be used, with the end result being different B cells specific for different antigens can be identified in the same experimental run.

X. Example 24

Barcoding RNA from Non-Cell Sources to Identify Antigen-Specific T Cells

This example describes an embodiment of the invention based on predicted results rather than results actually achieved. In this example, exogenously introduced RNA is barcoded and used to identify antigen-specific B cells. Spike-In DNA is generated as in Example 21, except that SPIKEIN-FW has a 5' NH2 modification. It is conjugated to a particular peptide-MHC antigen using All-in-One Antibody-Oligonucleotide Conjugation Kit (Solulink). RNA generated from Spike-In DNA using in vitro transcription may also be conjugated instead to peptide-MHC complex.

T cells are prepared and sequenced as in Example 15, with an additional step being the T cells are incubated with the Spike-In conjugated anti-CD4 antibody before running the T cells on a droplet generator and subsequently barcoding the RNA. Reads obtained are binned based on index-ID and barcodes added by barcode adapters. Therefore, reads can be binned back to the original reaction container. Smith-Waterman alignment of the contig with the Spike-In sequence using a scoring matrix of 2 for a match, −1 for a mismatch, −1 for a gap open and −1 for a gap extension is done. Any contig with a score >800 is considered a match. We then count the reaction containers in which a match was observed. For reaction containers in which the Spike-In sequence is detected, the T cell is then identified as antigen-specific (FIG. 14C). Multiple different peptide-MHCs coupled with different Spike-In sequences can be used, with the end result being different T cells recognizing different peptide-MHCs can be identified in the same experimental run.

TABLE 33

| Most frequently observed genes. | | |
|---|---|---|
| geneID | Description | cells |
| ENSG00000062716 | vacuole membrane protein 1 | 101 |
| ENSG00000137265 | interferon regulatory factor 4 | 59 |
| ENSG00000075624 | actin, beta | 47 |
| ENSG00000092820 | ezrin | 32 |
| ENSG00000026508 | CD44 molecule (Indian blood group) | 30 |
| ENSG00000111537 | interferon, gamma | 30 |
| ENSG00000177954 | ribosomal protein S27 | 30 |
| ENSG00000070756 | poly(A) binding protein, cytoplasmic 1 | 25 |
| ENSG00000132510 | lysine (K)-specific demethylase 6B | 25 |
| ENSG00000164924 | tyrosine 3-monooxygenase/tryptophan 5-monooxygenase activation protein, zeta | 25 |

It is understood that the examples and embodiments described herein are for illustrative purposes only and that various modifications or changes in light thereof will be suggested to persons skilled in the art and are to be included within the spirit and purview of this application and scope of the appended claims. All publications, sequence accession numbers, patents, and patent applications cited herein are hereby incorporated by reference in their entirety for all purposes.

---

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US09580736B2). An electronic copy of the "Sequence Listing" will also be available from the USPTO upon request and payment of the fee set forth in 37 CFR 1.19(b)(3).

What is claimed is:

1. A method for producing one or more polynucleotides of interest, the method comprising:
   obtaining a plurality of RNAs associated with one or more samples, wherein
   the samples are obtained from one or more subjects, and
   the RNAs associated with a sample are present in a separate reaction volume;
   adding an adapter molecule to the RNAs associated with the sample, wherein the adapter molecule is generated using an enzymatic reaction and comprises a universal priming sequence, a barcode sequence, and a binding site,
   wherein the adapter molecule is generated by contacting a template molecule with one or more enzymes and the template molecule is a DNA molecule comprising an RNA polymerase (RNAP) promoter, and the one or more enzymes include an RNA polymerase; and
   incorporating the barcode sequence into one or more polynucleotides associated with the sample,
   thereby producing the one or more polynucleotides of interest.

2. The method of claim 1, further comprising generating the adapter molecule using the enzymatic reaction.

3. The method of claim 1, wherein the RNAP promoter is selected from the group consisting of T7, T3, and SP6.

4. The method of claim 1, wherein:
   the template molecule is bound to a solid support,
   the solid support is contacted with an aqueous solution, and
   the adapter molecule is released into the aqueous solution as it is generated.

5. The method of claim 4, wherein:
   the template molecule comprises an endonuclease restriction site,
   the one or more enzymes comprise a restriction endonuclease, and
   the adapter molecule comprises a portion of the template molecule, said portion being generated and released into the aqueous solution upon contacting the template molecule with the restriction endonuclease.

6. The method of claim 1, wherein the adapter molecule is generated in a compartment, and adding the adapter molecule to the RNAs associated with one sample comprises combining the compartment with the reaction volume in which the RNAs are present.

7. The method of claim 1, wherein the adapter molecule further comprises a unique molecular identifier (UMI) sequence.

8. The method of claim 1, wherein the adapter molecule is an RNA molecule.

9. The method of claim 1, further comprising reverse-transcribing the RNAs associated with the sample to obtain a plurality of cDNAs, wherein reverse-transcribing an RNA comprises synthesizing a first strand of cDNA using a reverse-transcriptase and a first-strand primer.

10. The method of claim 9, wherein:
    the reverse transcriptase has template switching activity,
    at least some first strands of cDNA associated with the sample comprise a 3' overhang,
    the binding site of the adapter molecule comprises a 3' portion complementary to the 3' overhang, and
    the adapter molecule serves as a template for the reverse transcriptase, such that the barcode sequence is incorporated into first strands of cDNAs associated with the sample.

11. The method of claim 10, wherein the 3' overhang comprises one or more C nucleotides and the 3' portion of the binding site comprises one or more G nucleotides.

12. The method of claim 9, wherein producing polynucleotides of interest comprises amplifying the first strands of cDNA for the sample using a first primer and a second primer, the second primer having the same sequence as at least a portion of the first-strand primer, wherein the first primer or the second primer is the adapter molecule.

13. The method of claim 1, wherein the sample comprises a cell.

14. The method of claim 13, wherein the cell is a blood cell, an immune cell, a tissue cell, or a tumor cell.

15. The method of claim 14, wherein the cell is a B cell or a T cell.

16. An adapter construct comprising an RNAP promoter sequence, a universal priming sequence, a barcode sequence, and a binding site.

17. The adapter construct of claim 16, further comprising a unique molecular identifier (UMI) sequence.

18. A solid support comprising the adapter construct of claim 16.

19. The solid support of claim 18, wherein the adapter construct is bound to the solid support via a covalent bond.

20. The solid support of claim 18, wherein multiple copies of the adapter construct are bound to the solid support.

21. The solid support of claim 20, wherein at least 10, 30, 100, 300, 1,000, 3,000, 10,000, 30,000, 100,000, 300,000, or 1,000,000 copies of the adapter construct are bound to the solid support.

22. The solid support of claim 20, wherein each copy of the adapter construct comprises the same barcode sequence.

23. An adapter template library comprising a plurality of the solid supports of claim 18.

24. The adapter template library of claim 23, wherein the plurality comprises at least 10, 30, 100, 300, 1,000, 3,000, 10,000, 30,000, 100,000, 300,000, or 1,000,000 solid supports.

* * * * *